US009957295B2

(12) United States Patent
Wang

(10) Patent No.: US 9,957,295 B2
(45) Date of Patent: May 1, 2018

(54) PEPTIDES INHIBITING COLD-INDUCIBLE RNA BINDING PROTEIN ACTIVITY

(71) Applicant: The Feinstein Institute for Medical Research, Manhasset, NY (US)

(72) Inventor: Ping Wang, Roslyn, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days. days.

(21) Appl. No.: 15/023,555

(22) PCT Filed: Sep. 24, 2014

(86) PCT No.: PCT/US2014/057141
§ 371 (c)(1),
(2) Date: Mar. 21, 2016

(87) PCT Pub. No.: WO2015/048083
PCT Pub. Date: Apr. 2, 2015

(65) Prior Publication Data
US 2016/0207960 A1 Jul. 21, 2016

Related U.S. Application Data

(60) Provisional application No. 61/881,798, filed on Sep. 24, 2013.

(51) Int. Cl.
| | | |
|---|---|---|
| *C07K 7/08* | (2006.01) | |
| *C07K 7/06* | (2006.01) | |
| *C07K 16/18* | (2006.01) | |
| *C07K 14/47* | (2006.01) | |
| *A61K 39/00* | (2006.01) | |
| *A61K 38/00* | (2006.01) | |

(52) U.S. Cl.
CPC ............... *C07K 7/06* (2013.01); *C07K 7/08* (2013.01); *C07K 14/47* (2013.01); *C07K 16/18* (2013.01); *A61K 38/00* (2013.01); *A61K 2039/505* (2013.01)

(58) Field of Classification Search
None
See application file for complete search history.

(56) References Cited

U.S. PATENT DOCUMENTS

| 5,919,661 | A | 7/1999 | Hillman et al. |
| 8,703,138 | B2 | 4/2014 | Wang |
| 9,109,023 | B2 | 8/2015 | Wang |
| 2012/0027761 | A1 | 2/2012 | Wang |
| 2014/0186353 | A1 | 7/2014 | Wang |
| 2014/0193412 | A1 | 7/2014 | Wang |

FOREIGN PATENT DOCUMENTS

| CN | 1589279 A | 3/2005 |
| CN | 1980649 A | 6/2007 |
| JP | H11-199507 | 7/1999 |
| WO | WO 01/09387 A1 | 2/2001 |
| WO | WO 2008087562 | * 10/2008 |
| WO | WO 2009/090287 A1 | 7/2009 |
| WO | WO 2010036919 | * 4/2010 |
| WO | WO 2010/120726 A1 | 10/2010 |
| WO | WO 2015/048083 A1 | 4/2015 |

OTHER PUBLICATIONS

Artero-Castro, A., et al., "Cold-Inducible RNA-Binding Protein Bypasses Replicative Senescence in Primary Cells Through Extracellular Signal-Regulated Kinase 1 and 2 Activation," *Molecular and Cellular Biology*, Apr. 2009 LNKD-PUBMED:19158277, vol. 29, No. 7, Jan. 21, 2009 (Jan. 21, 2009), pp. 1855-1868, XP002594596 ISSN: 1098-5549. DOI: http://dx.doi.org/10.1128/MCB.01386-08.
Blom, et al., Comment on "The Influence of the Proinflammatory Cytokine, Osteopontin, on Autoimmune Demyelinating Disease," Science Mag, 299:1845a (2003).
De Leeuw, F., et al., "The Cold-Inducible RNA-Binding Protein Migrates from the Nucleus to Cytoplasmic Stress Granules by a Methylation-Dependent Mechanism and Acts as a Translational Repressor," *Experimental Cell Research*, 313:4130-4144 (2007).
Farr, C., et al., "Supplement to the Art of Getting Well Hydrogen Peroxide Therapy," pp. 1-7, Retrieved from the internet: URL: http://www.arthritistrust.org/wp-content/uploads/2012/10/Hydrogen-Peroxode-Therapy.pdf [retrieved on Dec. 22, 2015] (Mar. 2005).
Fujita, J., "Cold Shock Response in Mammalian Cells," *Journal of Molecular Microbiology and Biotechnology*, Horizon Scientific Press, Wymondham, GB, vol. 1, No. 2, Jan. 1, 1999 (Jan. 1, 1999), pp. 243-255, XP007912820 ISSN: 1464-1801.
Hunt, K. K. and Vorburger, S. A., "Hurdles and Hopes for Cancer Treatment," *Science*, 297:415-416 (2002).
Idrovo, et al., "Deficiency in Cold-Inducible RNA-Binding Protein (CIRP) Improves Cutaneous Wound Healing," Journal of Surgical Research, 179(2):Abstract No. ASC20131010 (Feb. 2013).
Idrovo, J.P., et al., "A Deficiency in Cold-Inducible RNA-Binding Protein Accelerates the Inflammation Phase and Improves Wound Healing," International Journal of Molecular Medicine, 37:423-428 (2016).
Leung, R. K. M. and Whittaker, P. A., "RNA Interference: from Gene Silencing to Gene-Specific Therapeutics," *Pharmacology and Therapeutics*, 107:222-239 (2005).
Lleonart, M.E., "A New Generation of Proto-Oncogenes: Cold-Inducible RNA Binding Proteins," *Biochemica et Biophysica Acta*, 1805:43-52 (2010).

(Continued)

*Primary Examiner* — Maury A Audet
(74) *Attorney, Agent, or Firm* — Hamilton, Brook, Smith & Reynolds, P.C.

(57) ABSTRACT

Disclosed are pharmaceutical compositions comprising a CIRP inhibitor. Methods of treating a subject suffering from an inflammatory condition comprising administering to said subject a CIRP inhibitor are also described herein.

4 Claims, 25 Drawing Sheets

(56) References Cited

OTHER PUBLICATIONS

Masuda, et al., "Cold-inducible RNA-binding protein (Cirp) interacts with Dyrk 1b/Mirk and Promotes Proliferation of Immature Male Germ Cells in Mice," PNAS, 109(27):10885-10890 (Jul. 2012).
Nishiyama, H., et al., "A Glycine-Rich RNA-Binding Protein Mediating Cold-Inducible Suppression of Mammalian Cell Growth," *The Journal of Cell Biology*, 137(4):899-908 (1997).
Park, B.M., et al., "Expression of Cold-Inducible RNA-Binding Protein in Normal Skin, Actinic Keratosis and Squamous Cell Carcinoma," *Ann Dermatol*, 26(2): 256-258 (2014).
Peng, Y., et al., "Cold-Inducible RNA Binding Protein is Required for the Expression of Adhesion Molecules and Embryonic Cell Movement in *Xenopus laevis*," *Biochemical and Biophysical Research Communications*, 344:416-424 (2006).
Qiang, X., et al., "Cold-inducible RNA-binding protein (CIRP) triggers inflammatory responses in hemorrhagic shock and sepsis", *Nature Med.*, 19(11):1489-1497 (Nov. 2013).
Romano, G., "Gene Transfer in Experimental Medicine," *Drug News Prospect*, 16(5):267-276 (2003).
Shi, et al., "Effects of Senescence and Manifestations of Aging in the Lung," p. A5284 Carbon Monoxide Inhibits Lung Fibrosis by Inducing Cellular Quiescence via E2F4. American Thoracic Society International Conference, ATS 2012. San Francisco, CA (May 2012.).
Van Venrooy, S., et al., "Cold-Inducible RNA Binding Protein (CIRP), a Novel XTcf-3 Specific Target Gene Regulates Neural Development in Xenopus," *BMC Developmental Biology*, 2008 LNKD- PUBMED:18687117, vol. 8:77, 2008, XP002594597 ISSN: 1471-213X. DOI: http://dx.doi.org/10.1186/1471-213X-8-77.
Xia, Z. et al., "Cold-inducible RNA-binding protein (CIRP) regulates target mRNA stabilization in the mouse testis", *FEBS Letters*, 586(19):3299-3308 (2012).
Xue, J-H, et al., "Effects of Ischemia and H2O2 on the Cold Stress Protein CIRP Expression in Rat Neuronal Cells," Free Radical Biology & Medicine, 27(11/12):1238-1244 (1999).
Yang, C. , et al., "The UV-Inducible RNA-Binding Protein A18 (A18 hnRNP) Plays a Protective Role in the Genotoxic Stress Response," *the Journal of Biological Chemistry*, Dec. 14, 2001 LNKD- PUBMED:11574538, vol. 276, No. 50, Dec. 14, 2001 (Dec. 14, 2001), pp. 47277-47284, XP002594598 ISSN: 0021-9258. DOI: http://dx.doi.org/10.1074/jbc.M105396200.
Zeng, Y., et al., "Down-Regulating Cold Shock Protein Genes Impairs Cancer Cell Survival and Enhances Chemosensitivity." *Journal of Cellular Biochemistry*, May 1, 2009 LNKD-PUBMED:19277990, vol. 107, No. 1, Mar. 10, 2009 (Mar. 10, 2009), pp. 179-188, XP002594595 ISSN: 1097-4644.
Notification of Transmittal of the International Search Report and the Written Opinion of the International Searching Authority, or the Declaration, International Search Report and Written Opinion in International Application No. PCT/US2010/030824, entitled "Treatment of Inflammatory Diseases by Inhibiting Cold-Inducible RNA-Binding Protein (CIRP)," 18 pages, dated Sep. 20, 2010.
Notification Concerning Transmittal of International Preliminary Report on Patentability and International Preliminary Report on Patentability in International Application No. PCT/US2010/030824, entitled "Treatment of Inflammatory Diseases by Inhibiting Cold-Inducible RNA-Binding Protein (CIRP)," 10 pages, dated Oct. 27, 2011.
Notification of Transmittal of the International Search Report and the Written Opinion of the International Searching Authority, or the Declaration, International Application No. PCT/US2014/057141, entitled "Peptides Inhibiting Cold-Inducible RNA Binding Protein Activity", dated Jan. 27, 2015.
Notification Concerning Transmittal of International Preliminary Report on Patentability, International Application No. PCT/US2014/057141, entitled "Peptides Inhibiting Cold-Inducible RNA Binding Protein Activity", dated Apr. 7, 2016.
Office Action, U.S. Appl. No. 13/264,205, entitled "Treatment of Inflammatory Diseases by Inhibiting Cold-Inducible RNA-Binding Protein (CIRP)," dated Jul. 23, 2012.
Office Action, U.S. Appl. No. 13/264,205, entitled "Treatment of Inflammatory Diseases by Inhibiting Cold-Inducible RNA-Binding Protein (CIRP)," dated May 29, 2013.
Notice of Allowance and Fees Due, U.S. Appl. No. 13/264,205, entitled "Treatment of Inflammatory Diseases by Inhibiting Cold-Inducible RNA-Binding Protein (CIRP)," dated Dec. 4. 2013.
Notice of Allowance and Fees Due, U.S. Appl. No. 14/196,354, entitled "Treatment of Inflammatory Diseases by Inhibiting Cold-Inducible RNA-Binding Protein (CIRP)", dated May 6, 2015.
Office Action, U.S. Appl. No. 14/152,091, entitled "Treatment of Cutaneous Wounds by Inhibiting Cold Shock Proteins," dated Oct. 28, 2015.
Office Action, U.S. Appl. No. 14/152,091, entitled "Treatment of Cutaneous Wounds by Inhibiting Cold Shock Proteins," dated May 9, 2016.

* cited by examiner

```
         10         20         30         40         50         60
MASDEGKLFV GGLSFDTNEQ SLEQVFSKYG QISEVVVVKD RETQRSRGFG FVTFENIDDA
         70         80         90        100        110        120
KDAMMAMNGK SVDGRQIRVD QAGKSSDNRS RGYRGGSAGG RGFFRGGRGR GRGFSRGGGD
        130        140        150        160        170
RGYGGNRFES RSGGYGGSRD YYSSRSQSGG YSDRSSGGSY RDSYDSYATH NE
```

(SEQ ID NO: 1)

FIG. 1

SEQUENCE LISTING

```
<160> NUMBER OF SEQ ID NOS: 44

<210> SEQ ID NO 1
<211> LENGTH: 172
<212> TYPE: PRT
<213> ORGANISM: Homo sapiens

<400> SEQUENCE: 1

Met Ala Ser Asp Glu Gly Lys Leu Phe Val Gly Gly Leu Ser Phe Asp
1               5                   10                  15

Thr Asn Glu Gln Ser Leu Glu Gln Val Phe Ser Lys Tyr Gly Gln Ile
            20                  25                  30

Ser Glu Val Val Val Val Lys Asp Arg Glu Thr Gln Arg Ser Arg Gly
        35                  40                  45

Phe Gly Phe Val Thr Phe Glu Asn Ile Asp Asp Ala Lys Asp Ala Met
    50                  55                  60

Met Ala Met Asn Gly Lys Ser Val Asp Gly Arg Gln Ile Arg Val Asp
65                  70                  75                  80

Gln Ala Gly Lys Ser Ser Asp Asn Arg Ser Arg Gly Tyr Arg Gly Gly
                85                  90                  95

Ser Ala Gly Gly Arg Gly Phe Phe Arg Gly Gly Arg Gly Arg Gly Arg
            100                 105                 110

Gly Phe Ser Arg Gly Gly Gly Asp Arg Gly Tyr Gly Gly Asn Arg Phe
        115                 120                 125

Glu Ser Arg Ser Gly Gly Tyr Gly Gly Ser Arg Asp Tyr Tyr Ser Ser
    130                 135                 140

Arg Ser Gln Ser Gly Gly Tyr Ser Asp Arg Ser Ser Gly Gly Ser Tyr
145                 150                 155                 160

Arg Asp Ser Tyr Asp Ser Tyr Ala Thr His Asn Glu
                165                 170

<210> SEQ ID NO 2
<211> LENGTH: 21
<212> TYPE: DNA
<213> ORGANISM: Artificial Sequence
<220> FEATURE:
<223> OTHER INFORMATION: PCR primers forward

<400> SEQUENCE: 2
caccatggca tcagatgaag g                                          21

<210> SEQ ID NO 3
<211> LENGTH: 20
<212> TYPE: DNA
<213> ORGANISM: Artificial Sequence
```

```
<220> FEATURE:
<223> OTHER INFORMATION: PCR primers reverse

<400> SEQUENCE: 3
ctcgttgtgt gtagcatagc                                              20

<210> SEQ ID NO 4
<211> LENGTH: 23
<212> TYPE: DNA
<213> ORGANISM: Artificial Sequence
<220> FEATURE:
<223> OTHER INFORMATION: PCR primers forward

<400> SEQUENCE: 4
gggtcctaca gagacagcta cga                                          23

<210> SEQ ID NO 5
<211> LENGTH: 20
<212> TYPE: DNA
<213> ORGANISM: Artificial Sequence
<220> FEATURE:
<223> OTHER INFORMATION: PCR primers reverse

<400> SEQUENCE: 5
ctggacgcag agggctttta                                              20

<210> SEQ ID NO 6
<211> LENGTH: 20
<212> TYPE: DNA
<213> ORGANISM: Artificial Sequence
<220> FEATURE:
<223> OTHER INFORMATION: PCR primers forward

<400> SEQUENCE: 6
atgactctac ccacggcaag                                              20

<210> SEQ ID NO 7
<211> LENGTH: 20
<212> TYPE: DNA
<213> ORGANISM: Artificial Sequence
<220> FEATURE:
<223> OTHER INFORMATION: PCR primers reverse

<400> SEQUENCE: 7
ctggaagatg gtgatgggtt                                              20

<210> SEQ ID NO 8
<211> LENGTH: 20
<212> TYPE: DNA
<213> ORGANISM: Artificial Sequence
<220> FEATURE:
<223> OTHER INFORMATION: PCR primers forward

<400> SEQUENCE: 8
cccagaccct cacactcaga                                              20

<210> SEQ ID NO 9
<211> LENGTH: 20
<212> TYPE: DNA
<213> ORGANISM: Artificial Sequence
<220> FEATURE:
<223> OTHER INFORMATION: PCR primers reverse

<400> SEQUENCE: 9
gccactactt cagcatctcg                                              20
```

```
<210> SEQ ID NO 10
<211> LENGTH: 26
<212> TYPE: DNA
<213> ORGANISM: Artificial Sequence
<220> FEATURE:
<223> OTHER INFORMATION: PCR primers

<400> SEQUENCE: 10
tgaaggtcgg tgtcaacgga tttggc                                          26

<210> SEQ ID NO 11
<211> LENGTH: 24
<212> TYPE: DNA
<213> ORGANISM: Artificial Sequence
<220> FEATURE:
<223> OTHER INFORMATION: PCR primers

<400> SEQUENCE: 11
catgtaggcc atgaggtcca ccac                                            24

<210> SEQ ID NO 12
<211> LENGTH: 10
<212> TYPE: PRT
<213> ORGANISM: Artificial Sequence
<220> FEATURE:
<223> OTHER INFORMATION: fragment of CIRP

<400> SEQUENCE: 12

Gly Arg Gly Phe Ser Arg Gly Gly Gly Asp
 1               5                  10

<210> SEQ ID NO 13
<211> LENGTH: 15
<212> TYPE: PRT
<213> ORGANISM: Artificial Sequence
<220> FEATURE:
<223> OTHER INFORMATION: fragment of CIRP

<400> SEQUENCE: 13

Gly Gly Arg Gly Arg Gly Arg Gly Phe Ser Arg Gly Gly Gly Asp
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: fragment of CIRP

<400> SEQUENCE: 14

Gly Arg Gly Phe Ser Arg Gly Gly Gly Asp Arg Gly Tyr Gly Gly
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: fragment of CIRP

<400> SEQUENCE: 15

Met Ala Ser Asp Glu Gly Lys Leu Phe Val Gly Gly Leu Ser Phe
 1               5                  10                  15

<210> SEQ ID NO 16
<211> LENGTH: 15
```

```
<212> TYPE: PRT
<213> ORGANISM: Artificial Sequence
<220> FEATURE:
<223> OTHER INFORMATION: fragment of CIRP

<400> SEQUENCE: 16

Gly Lys Leu Phe Val Gly Gly Leu Ser Phe Asp Thr Asn Glu Gln
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: fragment of CIRP

<400> SEQUENCE: 17

Gly Gly Leu Ser Phe Asp Thr Asn Glu Gln Ser Leu Glu Gln Val
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: fragment of CIRP

<400> SEQUENCE: 18

Asp Thr Asn Glu Gln Ser Leu Glu Gln Val Phe Ser Lys Tyr Gly
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: fragment of CIRP

<400> SEQUENCE: 19

Ser Leu Glu Gln Val Phe Ser Lys Tyr Gly Gln Ile Ser Glu Val
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: fragment of CIRP

<400> SEQUENCE: 20

Phe Ser Lys Tyr Gly Gln Ile Ser Glu Val Val Val Val Lys Asp
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: fragment of CIRP

<400> SEQUENCE: 21

Gln Ile Ser Glu Val Val Val Val Lys Asp Arg Glu Thr Gln Arg
 1               5                  10                  15

<210> SEQ ID NO 22
<211> LENGTH: 16
<212> TYPE: PRT
```

```
<213> ORGANISM: Artificial Sequence
<220> FEATURE:
<223> OTHER INFORMATION: fragment of CIRP

<400> SEQUENCE: 22

Val Val Val Lys Asp Arg Glu Thr Gln Arg Ser Arg Gly Phe Gly Phe
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: fragment of CIRP

<400> SEQUENCE: 23

Arg Glu Thr Gln Arg Ser Arg Gly Phe Gly Phe Val Thr Phe Glu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: fragment of CIRP

<400> SEQUENCE: 24

Ser Arg Gly Phe Gly Phe Val Thr Phe Glu Asn Ile Asp Asp Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: fragment of CIRP

<400> SEQUENCE: 25

Phe Val Thr Phe Glu Asn Ile Asp Asp Ala Lys Asp Ala Met Met
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: fragment of CIRP

<400> SEQUENCE: 26

Asn Ile Asp Asp Ala Lys Asp Ala Met Met Ala Met Asn Gly Lys
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: fragment of CIRP

<400> SEQUENCE: 27

Lys Asp Ala Met Met Ala Met Asn Gly Lys Ser Val Asp Gly Arg
1               5                   10                  15

<210> SEQ ID NO 28
<211> LENGTH: 15
<212> TYPE: PRT
<213> ORGANISM: Artificial Sequence
```

```
<220> FEATURE:
<223> OTHER INFORMATION: fragment of CIRP

<400> SEQUENCE: 28

Ala Met Asn Gly Lys Ser Val Asp Gly Arg Gln Ile Arg Val Asp
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: fragment of CIRP

<400> SEQUENCE: 29

Ser Val Asp Gly Arg Gln Ile Arg Val Asp Gln Ala Gly Lys Ser
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: fragment of CIRP

<400> SEQUENCE: 30

Gln Ile Arg Val Asp Gln Ala Gly Lys Ser Ser Asp Asn Arg Ser
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: fragment of CIRP

<400> SEQUENCE: 31

Gln Ala Gly Lys Ser Ser Asp Asn Arg Ser Arg Gly Tyr Arg Gly
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: fragment of CIRP

<400> SEQUENCE: 32

Ser Asp Asn Arg Ser Arg Gly Tyr Arg Gly Gly Ser Ala Gly Gly
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: fragment of CIRP

<400> SEQUENCE: 33

Arg Gly Tyr Arg Gly Gly Ser Ala Gly Gly Arg Gly Phe Phe Arg
 1               5                  10                  15

<210> SEQ ID NO 34
<211> LENGTH: 15
<212> TYPE: PRT
<213> ORGANISM: Artificial Sequence
<220> FEATURE:
```

```
<223> OTHER INFORMATION: fragment of CIRP

<400> SEQUENCE: 34

Gly Ser Ala Gly Gly Arg Gly Phe Phe Arg Gly Gly Arg Gly Arg
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: fragment of CIRP

<400> SEQUENCE: 35

Arg Gly Phe Phe Arg Gly Gly Arg Gly Arg Gly Arg Gly Phe Ser
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: fragment of CIRP

<400> SEQUENCE: 36

Arg Gly Gly Gly Asp Arg Gly Tyr Gly Gly Asn Arg Phe Glu Ser
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: fragment of CIRP

<400> SEQUENCE: 37

Arg Gly Tyr Gly Gly Asn Arg Phe Glu Ser Arg Ser Gly Gly Tyr
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: fragment of CIRP

<400> SEQUENCE: 38

Asn Arg Phe Glu Ser Arg Ser Gly Gly Tyr Gly Gly Ser Arg Asp
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: fragment of CIRP

<400> SEQUENCE: 39

Arg Ser Gly Gly Tyr Gly Gly Ser Arg Asp Tyr Tyr Ser Ser Arg
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: fragment of CIRP
```

```
<400> SEQUENCE: 40

Gly Gly Ser Arg Asp Tyr Tyr Ser Ser Arg Ser Gln Ser Gly Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: fragment of CIRP

<400> SEQUENCE: 41

Tyr Tyr Ser Ser Arg Ser Gln Ser Gly Gly Tyr Ser Asp Arg Ser
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: fragment of CIRP

<400> SEQUENCE: 42

Ser Gln Ser Gly Gly Tyr Ser Asp Arg Ser Ser Gly Gly Ser Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: fragment of CIRP

<400> SEQUENCE: 43

Tyr Ser Asp Arg Ser Ser Gly Gly Ser Tyr Arg Asp Ser Tyr Asp
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: fragment of CIRP

<400> SEQUENCE: 44

Ser Gly Gly Ser Tyr Arg Asp Ser Tyr Asp Ser Tyr Ala Thr His
1               5                   10                  15
```

PEPTIDES INHIBITING COLD-INDUCIBLE RNA BINDING PROTEIN ACTIVITY

This application is the U.S. National Stage of International Application No. PCT/US2014/057141, filed Sep. 24, 2014, which designates the U.S., published in English, and claims the benefit of U.S. Provisional Application No. 61/881,798, filed on Sep. 24, 2013. The entire teachings of the above application are incorporated herein by reference.

GOVERNMENT SUPPORT

This invention was made with government support under grants RO1 HL 076179 and GM053008 awarded by the National Institutes of Health. The Government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

File name: 32681023002SEQLIST.txt; created Mar. 18, 2016; 11 KB in size.

BACKGROUND OF THE INVENTION

Inflammation is the complex biological response of vascular tissues to harmful stimuli, such as pathogens, damaged cells, or irritants. It is a protective attempt by the organism to remove the injurious stimuli as well as initiate the healing process for the tissue. In the absence of inflammation, wounds and infections would heal at best more slowly and progressive destruction of the tissue would compromise the survival of the organism. However, inflammation which runs unchecked can also lead to a host of diseases.

Inflammation can be classified as either acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Hemorrhagic shock from loss of blood volume and multiple organ failure continue to be among leading causes of death in medical and surgical intensive care units with unacceptably high mortality rates. Even though numerous modalities and substances have been studied to prevent circulatory collapse and to reduce mortality, none have been entirely successful.

Similarly, wound healing is a dynamic and complex process involving hemostasis, inflammation, repair, and remodeling, Numerous cell types, enzymes, proteins and signaling molecules are required to work in a coordinated manner during the healing process. Many treatment options exist for wound care, including silver treatment, negative pressure wound devices, hyperbaric oxygen, skin substitutes, advanced dressings, and growth factor and biological wound products. Despite the multitude of available clinical tools, chronic wounds still cannot be effectively treated and managed. Non-healing wounds still remain a significant clinical problem and often lead to amputations. Cutaneous wounds in particular continue to cause significant morbidity and mortality despite advancements in wound care management. Acute cutaneous wounds caused by trauma can become chronic (non-healing) wounds if a patient also suffers from disorders such as diabetes or a cardiovascular disease. Patients may die from complications of chronic wounds such as wound infection, sepsis and septic shock, as well as thromboembolic events from prolonged immobilization.

SUMMARY OF THE INVENTION

In one aspect, the present invention is based on the discovery that the inhibition of Cold-Inducible RNA-Binding Protein (CIRP) attenuates inflammatory responses. More specifically, Applicant has discovered that inhibition of CIRP decreases levels of aspartate aminotransferase (AST), liver myeloperoxidase (MPO), lactate, TNF, serum TNF and serum, lung and liver IL-6 in animal models of hemorrhagic shock compared with untreated control (FIGS. 7-8). In addition, inhibition of CIRP decreases hemorrhage-induced mortality (FIG. 6). Based on this discovery, pharmaceutical compositions and methods for treatment of inflammatory conditions are disclosed.

In one embodiment, the present invention is an isolated peptide comprising an amino acid residue sequence of Gly-Arg-Gly-Phe-Ser-Arg-Gly-Gly-Gly-Asp (SEQ ID NO: 12) or a pharmaceutically acceptable salt thereof; or an amino acid residue sequence having at least 80% homology to SEQ ID NO: 12 or a pharmaceutically acceptable salt thereof, wherein the length of the peptide is 10 to 30 amino acid residues.

In another embodiment, the present invention is a pharmaceutical composition comprising a pharmaceutically acceptable carrier or diluent and an isolated peptide comprising an amino acid residue sequence of SEQ ID NO: 12, or an amino acid residue sequence having at least 80% homology to SEQ ID NO: 12.

In another embodiment, the present invention is a method of treating a subject with an inflammatory condition, comprising administering to the subject an effective amount of an isolated peptide comprising an amino acid residue sequence of SEQ ID NO: 12 or a pharmaceutically acceptable salt thereof, or an amino acid residue sequence having at least 80% homology to SEQ ID NO: 12, or a pharmaceutically acceptable salt thereof.

In another embodiment, the present invention relates to methods of inhibiting one or more biological activities of CIRP, comprising contacting CIRP with an isolated peptide comprising an amino acid residue sequence of SEQ ID NO: 12 or a pharmaceutically acceptable salt thereof, or with an isolated peptide comprising an amino acid residue sequence having at least 80% homology to SEQ ID NO: 12, or a pharmaceutically acceptable salt thereof. In particular, Applicant has discovered that the peptides of the present invention, specifically an isolated peptide comprising a sequence of SEQ ID NO: 12 or a residue sequence having at least 80% homology to SEQ ID NO: 12, effectively inhibit the CIRP-mediated release of proinflammatory cytokines, whereas other peptides have no such inhibitory effect on the biological activities of CIRP.

In another aspect, the present invention is based on the discovery that expression of CIRP hinders the healing process. Modulating CIRP expression and/or biological activity provides a novel target for wound therapeutics.

Accordingly, in one embodiment, the present invention is a method of treating a subject suffering from a cutaneous wound, comprising administering to the subject an effective amount of an isolated peptide comprising an amino acid residue sequence of SEQ ID NO: 12 or a pharmaceutically acceptable salt thereof, or comprising an amino acid residue sequence having at least 80% homology to SEQ ID NO: 12, or a pharmaceutically acceptable salt thereof.

BRIEF DESCRIPTION OF THE DRAWINGS

FIG. 1 is depiction of the amino acid sequence of the human CIRP (SEQ ID NO: 1).

FIGS. 2A and 2B are bar plot showing fold increase in CIRP expression in the liver and heart tissues, respectively, in animal hemorrhage model. FIGS. 2C and 2D are photographs of the chromatographically separated CIRP detected by Western blotting.

In FIG. 8G, liver myeloperoxidase (MPO) activity is increased by experimental hemorrhage, and this increase is reversed by administration of anti-CIRP antibodies, but not by control antibodies.

FIG. 9D shows a photograph of the Western blot of nuclear and cytoplasmic components of cell extracts from normoxic and hypoxic RAW 264.7 cells. FIG. 9E shows fluorescence microscopy photograph of RAW 264.7 cells transfected with a GFP-CIRP expression plasmid. FIG. 9F is a photograph of a Western blot detecting CIRP in the conditioned medium in which RAW 264.7 cells were gown 0, 7, and 24 hours post hypoxic shock. FIG. 9G is a Western blot detecting CIRP in the cell lysate from RAW 264.7 cells 0, 7, and 24 hours post hypoxic shock. FIG. 9H shows a Western blot of the cell extract from RAW 264.7 cells cultured under either normoxic or hypoxic conditions. The lysate was fractionated to the nuclear (N) and lysosomal (L) components. In FIGS. 9A, 9B and 9F, "PS red" is Ponceau S red staining for Western blot membrane to show protein loading.

FIGS. 10A, 10B, and 10D—RAW 264.7 cells; FIG. 10E—human THP-1 cells; FIG. 10F—human PBMC line.

FIGS. 16A through 16 D demonstrate an additive effect of CIRP and HMGB1 on the stimulation of TNF-α release.

DETAILED DESCRIPTION OF THE INVENTION

Figure 2:
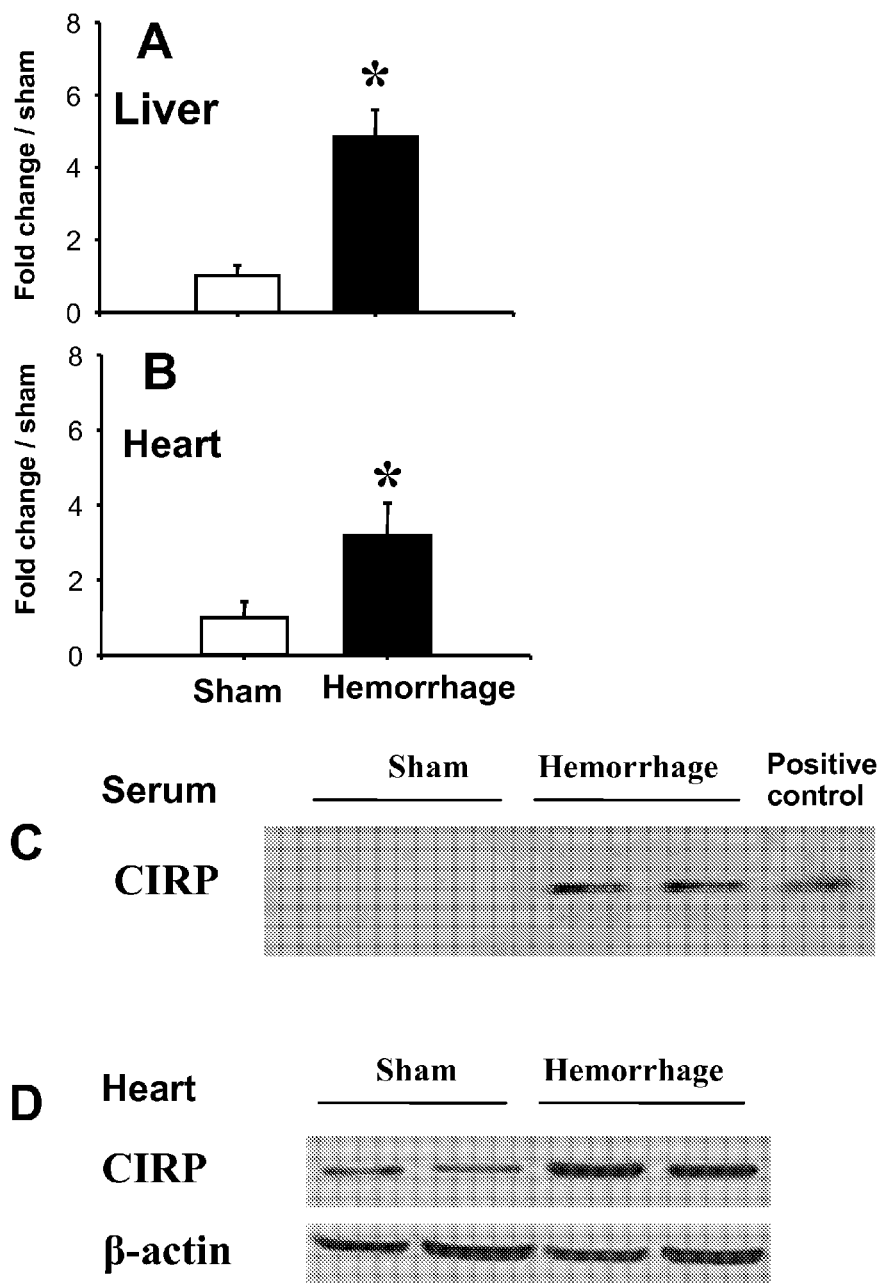
FIGS. 2A through 2D illustrate the over-expression of CIRP gene in the liver, heart and blood in animal models of hemorrhage compared with sham (not bled) control.

Applicant surprisingly discovered that during an inflammatory response, CIRP expression is upregulated and is released into the circulation. Applicant has also discovered that once CIRP enters the blood stream, it acts as a potent proinflammatory mediator or cytokine and causes tissue injury and even death.

Accordingly, the present invention is based on the discovery of CIRP as a new inflammatory mediator. This discovery enabled the elucidation of an alternative mechanism for inducing inflammation, and further enabled the Applicant to develop therapeutic strategies targeting CIRP for the treatment of inflammation.

CIRP is a mammalian protein induced in cultured cells by mild cold stress (32° C.). Murine and human CIRP is a 172-aa (95% identical) nuclear protein, comprising an N-terminal RNA-binding domain and a C-terminal Glycine-rich domain, and functions as an RNA chaperone to facilitate translation. The amino acid sequence of human CIRP is provided in FIG. 1, SEQ ID NO:1 (see Nishiyama et al. The Journal of Cell Biology, Volume 137, 1997). "Mammalian CIRP" includes proteins having an amino acid sequence which is the same as that of a naturally occurring or endogenous corresponding mammalian CIRP (e.g., recombinant proteins, synthetic proteins (i.e., produced using the methods of synthetic organic chemistry)). The term also includes polymorphic or allelic variants, and other isoforms of a CIRP (e.g., produced by alternative splicing or other cellular processes), and modified or unmodified forms of the foregoing (e.g., lipidated, glycosylated, and unglycosylated. Such proteins can be recovered or isolated from a source which naturally produces mammalian CIRP. CIRP plays an essential role in cold-induced suppression of cell proliferation. The present invention is based on the surprising discovery that extracellular CIRP is an endogenous proinflammatory mediator causing deleterious effects during hemorrhagic and septic shock. Thus, the present invention is directed to CIRP antagonism as a previously unappreciated therapeutic target.

Intracellular CIRP has known biological functions of stabilizing specific mRNAs and facilitating translation for survival advantage when cells are under stress conditions (Yang, C. & Carrier, F. The UV-inducible RNA-binding protein A18 (A18 hnRNP) plays a protective role in the genotoxic stress response. *J. Biol. Chem.* 276, 47277-47284 (2001); Cammas, A., Lewis, S. M., Vagner, S. & Holcik, M. Post-transcriptional control of gene expression through subcellular relocalization of mRNA binding proteins. *Biochem. Pharmacol.* 76, 1395-1403 (2008)). Applicant has discovered that extracellular CIRP is a new damage-associated molecular pattern (DAMP) molecule, and substantiates this finding with experimental evidence (Example 1). First, Applicants detected CIRP in the serum of surgical ICU patients as well as hemorrhaged and septic animals. Second, under the hypoxic stress or exposure to lipopolysaccride (LPS), CIRP in macrophages translocates from the nucleus to the cytoplasm and is actively released into the extracellular matrix. Third, recombinant CIRP proteins induce TNF-α and HMGB1 release from macrophages in vitro, stimulate inflammatory responses and cause tissue injury in healthy animals. Fourth, the inhibition of extracellular CIRP activity by neutralizing anti-CIRP antibodies significantly improves the survival of hemorrhaged and septic animals through the attenuation of shock-induced inflammation, tissue injury, and lethality. Finally, CIRP interacts with TLR4, which is one of the pattern-recognition receptors (PRRs) that is commonly utilized by DAMPs to trigger inflammatory responses. Thus, extracellular CIRP is a bona fide proinflammatory mediator.

CIRP translocates from the nucleus to the cytoplasm in RAW 264.7 cells after exposure to hypoxia. Such CIRP translocation has also been observed in other cell types, including fibroblasts and epithelial cells, when under UV exposure, osmotic shock, heat shock and endoplasmic reticulum stresses (De Leeuw, F., et al. The cold-inducible RNA-binding protein migrates from the nucleus to cytoplasmic stress granules by a methylation-dependent mechanism and acts as a translational repressor. *Exp. Cell Res.* 313, 4130-4144 (2007); Yang, R., et al. Functional significance for a heterogenous ribonucleoprotein A18 signature RNA motif in the 3'-untranslated region of ataxia telangiectasia mutated and Rad3-related (ATR) transcript. *J. Biol. Chem.* 285, 8887-8893 (2010)). Methylation of arginine residues in the RGG domain under environmental stresses (De Leeuw, F., et al. *Exp. Cell Res.* 313, 4130-4144 (2007)) and phosphorylation at the C-terminal region in response to UV radiation (Yang, R., et al. *J. Biol. Chem.* 285, 8887-8893 (2010)) have been postulated for regulating CIRP exit from the nucleus. CIRP is released into CM in response to hypoxia or LPS. A number of non-canonical pathways have been proposed for release of "leaderless" proteins, including microvesicle shedding, exocytosis of secretory lysosomes, and active transport (Qu, Y. & Dubyak, G. R. P2X7 receptors regulate multiple types of membrane trafficking responses and non-classical secretion pathways. *Purinergic Signal.* 5, 163-173 (2009)). In addition, an alternative model of leaderless IL-1β secretion can be completed by formation of multivesicular bodies containing exosomes with entrapped IL-1β and later fusion of these multivesicular bodies with the plasma membrane to release exosomes (see Qu, Y., Franchi, L., Nunez, G. & Dubyak, G. R. Nonclassical IL-1 beta secretion stimulated by P2X7 receptors is dependent on inflammasome activation and correlated with exosome release in murine macrophages. *J. Immunol.* 179, 1913-1925 (2007)). Without being bound to theory, one method for CIRP release is through lysosomal secretion.

Extracellular CIRP's activity is mediated through the TLR4/MD2 complex (Example 9). Surface Plasmon resonance analysis indicated that CIRP bound to the TLR4/MD2 complex as well as to individual TLR4 and MD2. Through this discovery, the Applicant has developed new inhibitors of CIRP activity, including, as described herein, a human CIRP-derived peptide, typically 10-30 amino acid residues in length, having a sequence of at least 80% homology to a portion of the hCIRP protein that lies between amino acid residues 106-125. The peptide binds with high affinity to MD2.

Identification of CIRP's TLR4-mediated proinflammatory activity is consistent with previous studies showing that TLR4 plays a significant role in mediating inflammation and organ injury in hemorrhaged animals (Benhamou, Y., et al. Toll-like receptors 4 contribute to endothelial injury and inflammation in hemorrhagic shock in mice. *Crit. Care Med.* 37, 1724-1728 (2009)) as well as septic animals (Wittebole, X., Castanares-Zapatero, D. & Laterre, P. F. Toll-like receptor 4 modulation as a strategy to treat sepsis. *Mediators*

*Inflamm.* 2010, 568396 (2010)). TLR4 can also recognize several endogenous molecules, including HMGB1, heat shock proteins, hyaluronic acid, and fibronectin when they are released from stressed, damaged or dying cells, or from degradation of the extracellular matrix (see (a) Park, J. S., et al. Involvement of toll-like receptors 2 and 4 in cellular activation by high mobility group box 1 protein. *J. Biol. Chem.* 279, 7370-7377 (2004); (b) Ohashi, K., Burkart, V., Flohé, S. & Kolb, H. Cutting edge: heat shock protein 60 is a putative endogenous ligand of the toll-like receptor-4 complex. *J. Immunol.* 164, 558-561 (2000); (c) Termeer, C., et al. Oligosaccharides of Hyaluronan activate dendritic cells via toll-like receptor 4. *J. Exp. Med.* 195, 99-111 (2002); (d) Okamura, Y., et al. The extra domain A of fibronectin activates Toll-like receptor 4. *J. Biol. Chem.* 276, 10229-10233 (2001)). Although many DAMPs serve as ligands of the TLR4/MD2 complex, some molecules may bind to the different sites of the TLR4/MD2 complex and work additively in stimulating proinflammatory cytokine production in macrophages, as demonstrated herein via the relationship between CIRP and HMGB1. As indicated by SPR analysis, HMGB1 bound to the TLR4/MD2 complex with a $K_D$ of $1.5 \times 10^{-6}$ M (Yang, H., et al. A critical cysteine is required for HMGB1 binding to Toll-like receptor 4 and activation of macrophage cytokine release. *Proc. Natl. Acad. Sci. USA* 107, 11942-11947 (2010)), which is comparable to CIRP's ($K_D = 2.39 \times 10^{-7}$ M). Further analysis indicated that HMGB1 bound to MD2 with a $K_D$ of $8 \times 10^{-9}$ M, but did not bind to TLR4 (Yang, H., Antoine, D. J., Andersson, U. & Tracey, K. J. The many faces of HMGB1: molecular structure-functional activity in inflammation, apoptosis, and chemotaxis. *J. Leukoc. Biol.* 93, 865-873 (2013)), whereas CIRP can bind to individual MD2 and TLR4. Mapping the subdomains of CIRP that interact with TLR4, MD2 and the TLR4/MD2 complex is being investigated to obtain more information on the overall molecular structure of CIRP as it concerns in binding to these receptors. Of note, the $K_D$ of LPS to TLR4 and MD2 is $1.41 \times 10^{-5}$ and $2.33 \times 10^{-6}$ M, respectively (Shin, H. J., et al. Kinetics of binding of LPS to recombinant CD14, TLR4, and MD-2 proteins. *Mol. Cell* 24, 119-124 (2007)).

CIRP can be actively released, despite the fact that "leaderless" proteins could be leaked out by passive modes, such as necrosis (Scaffidi, P., Misteli, T. & Bianchi, M. E. Release of chromatin protein HMGB1 by necrotic cells triggers inflammation. *Nature* 418, 191-195 (2002)). A recent study reports the involvement of CIRP in activating the NF-κB pathway for regulating IL-1β expression in cultured fibroblasts, in which neutralizing anti-CIRP antibodies are utilized as treatment in improving the survival of hemorrhaged and septic animals (see Brochu, C., et al. NF-kappaB-Dependent Role for Cold-Inducible RNA Binding Protein in Regulating Interleukin 1beta. *PLoS One* 8, e57426 (2013)). Thus, targeting CIRP may provide therapeutic potential to ameliorate morbidity and mortality for victims of hemorrhage and sepsis.

Inhibition of CIRP leads to reduction in levels of inflammatory mediators and markers including but not limited to, aspartate aminotransferase (AST), liver myeloperoxidase (MPO), lactate, TNF, serum TNF and serum, lung and liver IL-6 in animal models of sepsis compared with untreated control (Examples 7 and 8). These decreases reflect and in some cases account for the beneficial effects of targeting CIRP in the treatment of inflammatory disease and conditions. Moreover, these decreases illustrate the therapeutic benefit of CIRP inhibitors and antagonist in the treatment of such diseases and conditions.

As defined herein, a "CIRP inhibitor" is an agent (e.g., molecule, a natural or synthetic nucleic acid or nucleic acid analog, antisense molecule, small interfering RNA (siRNA), protein, peptide, antibody, antigenic fragment, chemical compound or the like), which binds CIRP and inhibits (e.g., reduces, prevents, decreases, neutralizes) one or more biological activities of CIRP; or an agent that inhibits the expression of CIRP gene and/or protein or the release of bioactive CIRP. The term "biological activity of CIRP" refers to CIRP receptor binding, CIRP signaling, CIRP-mediated release of proinflammatory cytokines, CIRP-mediated inflammation and/or other CIRP-mediated activities. The term "antagonist" can be used interchangeably with the term "inhibitor".

The CIRP inhibitor can be an antibody, which binds and inhibits (e.g., reduces, prevents or neutralizes) one or more biological activities or functions of CIRP.

The antibody can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies, including fragments of chimeric, humanized, primatized, veneered or single chain antibodies. Functional fragments include antigen-binding fragments which bind to a mammalian CIRP. Such fragments can be produced by enzymatic cleavage or by recombinant techniques. For example, papain, pepsin or other protease with the requisite substrate specificity can also be used to generate fragments. Antibodies can also be produced in a variety of truncated forms using antibody genes in which one or more stop codons has been introduced upstream of the natural stop site.

Single chain antibodies, and chimeric, humanized or primatized (CDR-grafted), or veneered antibodies, as well as chimeric, CDR-grafted or veneered single chain antibodies, comprising fragments derived from different species, and the like are also encompassed by the present invention and the term "antibody". The various fragments of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Antibodies which are specific for a mammalian (e.g., human) CIRP can be raised against an appropriate immunogen, such as isolated and/or recombinant human protein of SEQ ID NO:1 or fragments thereof (including synthetic molecules, such as synthetic peptides). Antibodies can also be raised by immunizing a suitable host (e.g., mouse) with cells that express CIRP. In addition, cells expressing a CIRP can be used as immunogens or in a screen for antibody which binds CIRP.

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M, et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody producing cells. Antibody producing cells can be obtained from the peripheral blood, the spleen, or lymph nodes of humans or other suitable animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library), or which rely upon immunization of transgenic animals (e.g., mice) capable of producing a repertoire of human antibodies (see e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807; Lonberg et al., WO97/13852). Such immunization and isolation procedures are well known to one of ordinary skill in the art.

An antigenic fragment is a substance which when introduced into the body stimulates the production of an antibody. Antigens could include toxins, bacteria, foreign blood cells, and/or cells of transplanted organs.

A CIRP inhibitor can be a peptide (e.g., synthetic, recombinant, fusion or derivatized) which specifically binds to and inhibits (reduces, prevents, decreases, neutralizes) the activity of the CIRP. The peptide can be linear, branched or cyclic, e.g., a peptide having a heteroatom ring structure that includes several amide bonds. In a particular embodiment, the peptide is a cyclic peptide. The peptide refers to a compound consisting of from about 2 to about 100 amino acid residues wherein the amino group of one amino acid is linked to the carboxyl group of another amino acid by a peptide bond. Such peptides are typically less than about 100 amino acid residues in length and in some embodiments are about 10, about 20, about 30, about 40 or about 50 residues.

Peptides that are selective for binding to a particular domain (e.g., unique domain) of a CIRP can be produced. A peptide can be, for example, derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis*," John Wiley & Sons, Second Edition, 1976). Peptides that are CIRP inhibitors can also be produced, for example, using recombinant DNA methodologies or other suitable methods (see, e.g., Sambrook J. and Russell D. W., *Molecular Cloning: A Laboratory Manual*, 3$^{rd}$ Edition, Cold Spring Harbor Laboratory Press, Cold Spring Harbor, N.Y., 2001).

CIRP inhibitors can also be fusion peptides fused, for example to a carrier protein (e.g., myc, his, glutathione sulfhydryl transferase) and/or tagged (e.g., radiolabeled, fluorescently labeled).

A peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide inhibitors can then be isolated using suitable methods.

The polypeptide can comprise modifications (e.g., amino acid linkers, acylation, acetylation, amidation, methylation, terminal modifiers (e.g., cyclizing modifications)), if desired. The polypeptide can also contain chemical modifications (e.g., N-methyl-α-amino group substitution). In addition, the peptide inhibitor can be an analog of a known and/or naturally-occurring peptide, for example, a peptide analog having conservative amino acid residue substitution(s). These modifications can improve various properties of the peptide (e.g., solubility, binding), including its CIRP inhibiting activity. The peptide inhibitors described herein also include pharmaceutically acceptable salts thereof, as described in the Modes of Administration section, below.

In certain aspects of the invention, the CIRP inhibitor is an isolated peptide, comprising an amino acid residue sequence of Gly-Arg-Gly-Phe-Ser-Arg-Gly-Gly-Gly-Asp (SEQ ID NO: 12), and having a length of about 10 to about 30 amino acid residues. In certain other aspects of the invention, the CIRP inhibitor is an isolated peptide comprising an amino acid residue sequence of Gly-Gly-Arg-Gly-Arg-Gly-Arg-Gly-Phe-Ser-Arg-Gly-Gly-Gly-Asp (SEQ ID NO: 13) or Gly-Arg-Gly-Phe-Ser-Arg-Gly-Gly-Gly-Asp-Arg-Gly-Tyr-Gly-Gly (SEQ ID NO: 14). In other aspects of the invention, the CIRP inhibitor is an isolated peptide comprising an amino acid residue sequence having at least 80%, or alternately 85%, 90%, 95%, 98% or 99% homology to any of SEQ ID NO: 12, SEQ ID NO: 13, or SEQ ID NO: 14.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, PILEUP/PRETTYBOX, ALIGN, ADVANCE, ADAM or FASTA programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used. A probability score indicates the probability that the homology of a closely related sequence is due only to random chance. In certain embodiments, a low probability score is between $1\times10^{-3}$ and $1\times10^{-100}$.

The percent homology of two amino acid sequences can be determined by aligning the sequences for optimal comparison purposes (e.g., gaps can be introduced in the sequence of a first sequence). The amino acid sequences at corresponding positions are then compared, and the percent identity between the two sequences is a function of the number of identical positions shared by the sequences (i.e., % identity=# of identical positions/total # of positions ×100). The percent identity between two amino acid sequences can also be accomplished using the GAP program in the GCG software package (Accelrys, San Diego, Calif.) using either a Blossom 63 matrix or a PAM250 matrix, and a gap weight of 12, 10, 8, 6, or 4 and a length weight of 2, 3, or 4. The length of the protein encoding can be aligned for comparison purposes is at least 80%, or alternately 85%, 90%, 95%, 98%, 99% or 100%, of the length of the reference sequence, for example, the CIRP-inhibitor comprising an amino acid residue sequence of any of SEQ ID NOs: 12, 13 or 14.

A peptidomimetic refers to molecules which are not polypeptides, but which mimic aspects of their structures. Peptidomimetic antagonists can be prepared by conventional chemical methods (see e.g., Damewood J. R. "Peptide Mimetic Design with the Aid of Computational Chemistry" in *Reviews in Computational Biology,* 2007, Vol. 9, pp. 1-80, John Wiley and Sons, Inc., New York, 1996; Kazmierski W. K., "*Methods of Molecular Medicine: Peptidomimetic Protocols,*" Humana Press, New Jersey, 1999). For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with the amino acid(s) at or near the ligand binding site. For example, the binding moieties in a peptidomimetic can be the same as those in a peptide or protein inhibitor. The binding moieties can be an atom or chemical group which reacts with the receptor in the same or similar manner as the binding moiety in the peptide inhibitor. For example, computational chemistry can be used to design peptidemimetics of the CIRP binding to inhibit the activity of CIRP. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more-CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic inhibitors can then be isolated by suitable methods.

Other CIRP inhibitors like, for example, non-peptidic compounds or small molecules, can be found in nature (e.g., identified, isolated, purified) and/or produced (e.g., synthesized). Agents can be tested for CIRP binding specificity in a screen for example, a high-throughput screen of chemical compounds and/or libraries (e.g., chemical, peptide, nucleic acid libraries). Compounds or small molecules can be identified from numerous available libraries of chemical compounds from, for example, the Chemical Repository of the National Cancer Institute, the Molecular Libraries Small Molecules Repository (PubChem) and other libraries that are commercially available. Such libraries or collections of molecules can also be prepared using well-known chemical methods, such as well-known methods of combinatorial chemistry. The libraries can be screed to identify compounds that bind and inhibit CIRP. Identified compounds can serve as lead compounds for further diversification using well-known methods of medicinal chemistry. For example, a collection of compounds that are structural variants of the lead can be prepared and screened for CIRP binding and/or inhibiting activity. This can result in the development of a structure activity relationship that links the structure of the compounds to biological activity. Compounds that have suitable binding and inhibitory activity can be further developed for in vivo use. In one example, small molecule, $NaN_3$, inhibits CIRP transcription, as disclosed in "Oxygen-regulated expression of the RNA-binding proteins RBM3 and CIRP by HIF-1-independent mechanism", by S. Wellmann et al., Journal of Cell Science, 117, 1785-1794, 2004.

In some embodiments of the invention, the CIRP inhibitor has molecular weight less than 1000 Daltons.

CIRP inhibitors are also agents that inhibit (reduce, decrease, neutralize, prevent) the expression of a CIRP. Agents (molecules, compounds, nucleic acids, oligonucleotides) which inhibit CIRP gene expression (e.g., transcription, mRNA processing, translation) are effective CIRP inhibitors. Antisense oligonucleotides (e.g., DNA, riboprobes) can also be used as CIRP inhibitors to inhibit CIRP subunit expression. Antisense oligonucleotides are generally short (~13 to ~25 nucleotides) single-stranded nucleic acids which specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002). There are a number of different types of antisense oligonucleotides that can be used as CIRP inhibitors including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate).

Antisense oligonucleotides can be designed to be specific for a CIRP using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells via the process of adsorptive endocytosis. Thus, in the treatment of a subject (e.g., mammalian), antisense CIRP can be delivered to target cells by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, E5CA peptide).

Methods of identifying an antagonist agent (e.g., an antibody) against CIRP will be described below.

A composition comprising a CIRP can be used in a binding assay to detect and/or identify agents that can bind to the CIRP including antibodies of the invention.

Compositions suitable for use in a binding assay include, for example, cells which naturally express a mammalian CIRP or functional variant thereof and recombinant cells expressing a mammalian CIRP or functional variant thereof. Compositions suitable for use in a binding assay also include, membrane preparations which comprise a mammalian CIRP or functional variant thereof. Such membrane preparations can contain natural (e.g., plasma membrane) or synthetic membranes. In some embodiments, the membrane preparation is a membrane fraction of a cell that contains a mammalian CIRP or a functional variant thereof.

In one embodiment, the method of detecting or identifying agent (e.g., an antibody) that binds to a mammalian CIRP is a competitive binding assay in which the ability of a test agent (e.g. an antibody) to inhibit the binding of a reference agent (e.g., a ligand or another antibody of known specificity) is assessed. For example, the reference agent can be labeled with a suitable label as described below, and the amount of labeled reference agent required to saturate the CIRP present in the assay can be determined. A saturating amount of labeled reference agent and various amounts of a test agent can be contacted with a composition comprising a mammalian CIRP or functional variant thereof under conditions suitable for binding and complex formation determined. The specificity of the formation of the complex between the CIRP and the test agent can be determined using a suitable control (e.g., unlabeled agent, label alone).

The formation of a complex between either the reference or a test agent and the CIRP or fragments thereof including immunogenic peptides as described above can be detected or measured directly or indirectly using suitable methods. For example, the agent can be labeled with a suitable label and the formation of a complex can be determined by detection of the label. The specificity of the complex can be determined using a suitable control such as unlabeled agent or label alone. Labels suitable for use in detection of a complex between an agent and a mammalian CIRP or functional variant thereof include, for example, a radioisotope, an epitope, an affinity label (e.g., biotin, avidin), a spin label, an enzyme, a fluorescent group or a chemiluminescent group.

With respect to a competitive binding assays used to determine the ability of a test agent such as an antibody to bind an CIRP, such ability can be reported as the concentration of test agent required for 50% inhibition ($IC_{50}$ values) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents which are suitable for use in the method include molecules and compounds which specifically bind to a mammalian CIRP or a functional variant thereof, for example, a ligand of CIRP or an antibody. Preferred reference agents are antibodies having a known specificity against the fragments of the human CIRP (SEQ ID NO:1).

In further aspects, the present invention also relates to methods for inhibiting one or more biological activities of CIRP. In some embodiments, a CIRP inhibitor inhibits CIRP-mediated signal transduction. As used herein "CIRP-mediated signal transduction" means activation of a cell surface receptor by extracellular signaling molecule CIRP. Activation of the cell surface receptor generates a physiological response from the cell. Activation occurs, for example, through CIRP binding to the cell surface receptor. In some embodiments of the invention, a CIRP inhibitor inhibits CIRP binding to a cell surface receptor, for example, MD2. In other embodiments of the invention, a CIRP inhibitor inhibits CIRP binding to a cell surface receptor complex, for example, MD2/TLR4. In other aspects of the invention, a CIRP inhibitor inhibits CIRP-mediated inflammation. In yet other aspects of the invention, a CIRP inhibitor inhibits CIRP-mediated release of a proinflammatory cytokine, for example, TNF-alpha.

The ability of an agent which binds CIRP to inhibit (e.g., reduce, prevent, neutralize) one or more "biological activities of CIRP" may be examined. As defined previously term "biological activity of CIRP" refers to CIRP receptor binding, CIRP signaling, CIRP-mediated release of proinflammatory cytokines, CIRP-mediated inflammation and/or other CIRP-mediated activities. Thus, assays detecting these CIRP-mediated functions can be used to evaluate the inhibition activity of a test agent (e.g., the ability of a test agent to inhibit one or more functions of CIRP).

Assessment of whether an agent (e.g., an antibody) inhibits a biological activity of a CIRP can be performed, for example, by determining whether an antibody inhibits release of a proinflammatory cytokine from a mammalian cell. Examples of suitable cytokines include TNF, IL-6 or HMGB1.

For these methods, the cell can be any cell that can be induced to produce a proinflammatory cytokine. The cell is an immune cell, for example macrophages, monocytes, or neutrophils.

Figure 4:
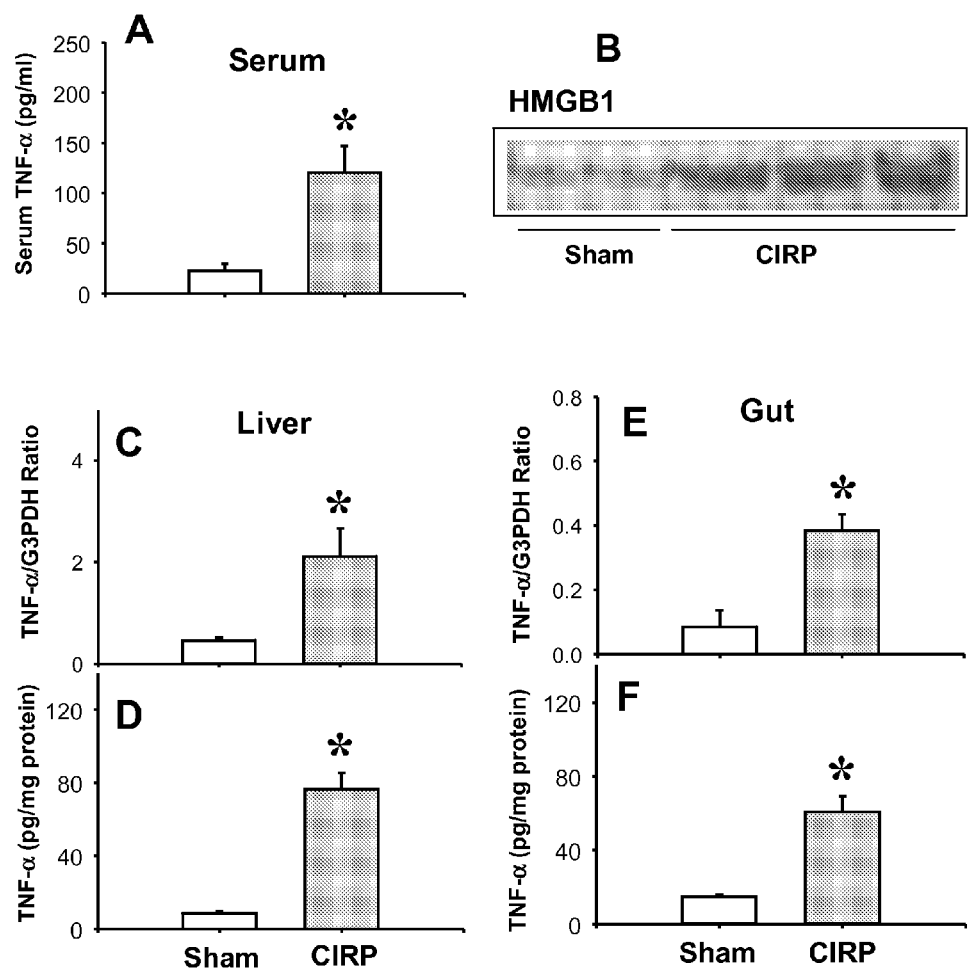
FIGS. 4A through 4F illustrate the increase in inflammatory cytokines TNF and HMGB1 in blood, liver and gut tissues after administration of rCIRP to healthy rats.
Figure 8:
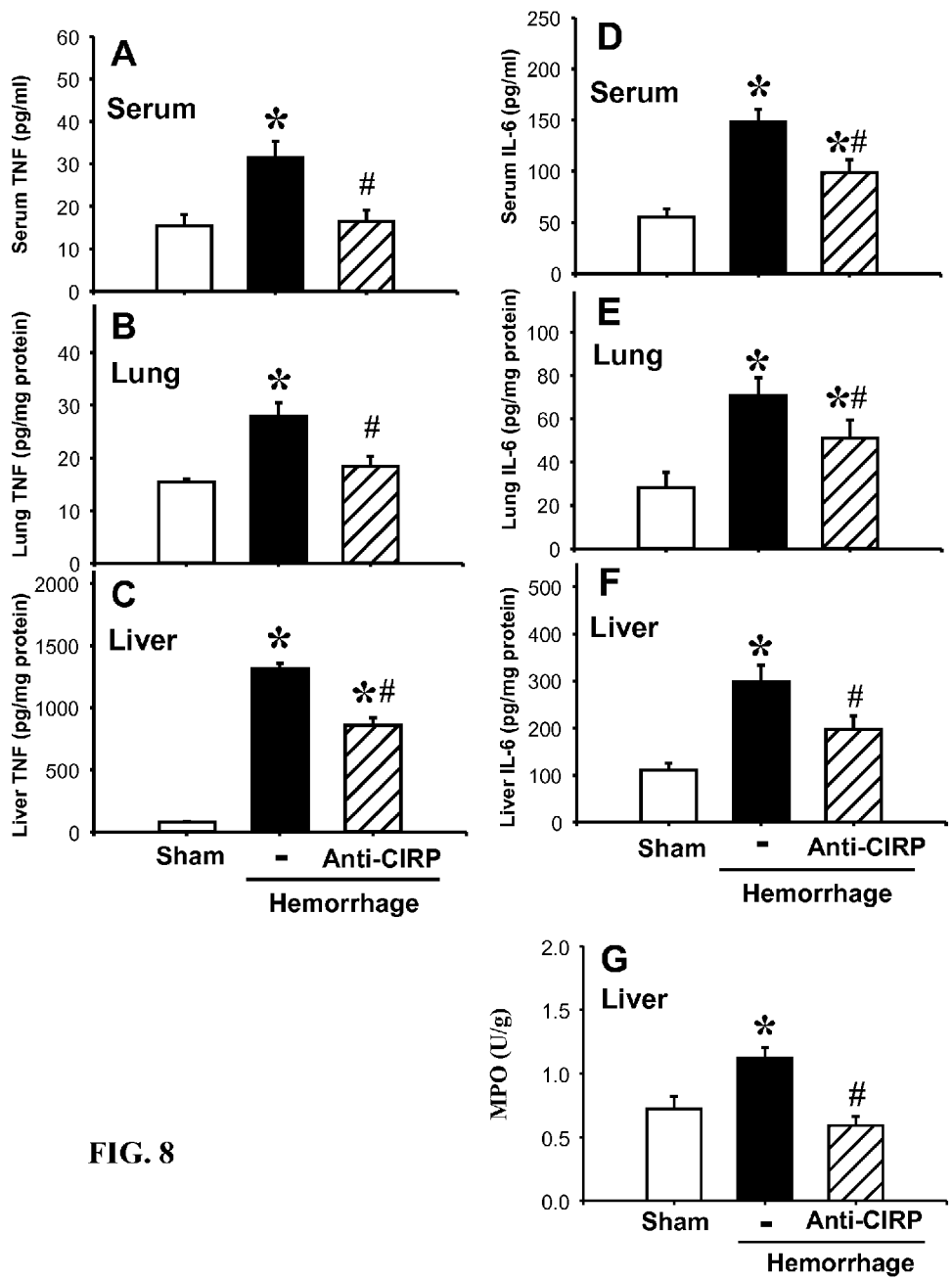
FIGS. 8A through G are graphs illustrating the reduction of serum, lung and liver IL-6 by anti-CIRP antibodies in animal models of hemorrhage after administration of anti-CIRP antibody, compared with untreated control.

Evaluation of the inhibition of cytokine production can be by any means known, including quantitation of the cytokine (e.g., with ELISA), or by bioassay, (e.g. determining whether proinflammatory cytokine activity is reduced), or by measurement of the proinflammatory cytokine mRNA. The skilled artisan could utilize any of these assays without undue experimentation. For non-limiting Examples on inhibition of the release of proinflammatory cytokine by the CIRP inhibiting agents see FIGS. 4 and 8. FIG. 8A shows reduction of serum TNF by treatment with anti-CIRP antibodies in an animal model of hemorrhage compared with untreated controls. Reduction of tissue TNF by treatment with anti-CIRP antibodies in an animal model of hemorrhage compared with untreated controls is shown in FIG. 8B-C. FIG. 8D-F shows reduction in IL-6 (e.g., serum, lung and liver IL-6) by treatment with anti-CIRP antibodies in an animal model of hemorrhage compared with untreated controls.

Another way of measuring proinflammatory cytokine release involves treating the mammalian cell with an antibody along with an agent that stimulates a proinflammatory cytokine cascade. In some embodiments, one agent is bacterial lipopolysaccharide (LPS). The compound can be administered to the mammalian cell either before the agent, at the same time as the agent, or after the agent. In certain embodiments, the compound is administered before the agent. See, e.g., U.S. Pat. No. 6,610,713, the relevant teachings of which are incorporated herein by reference.

Figure 7:
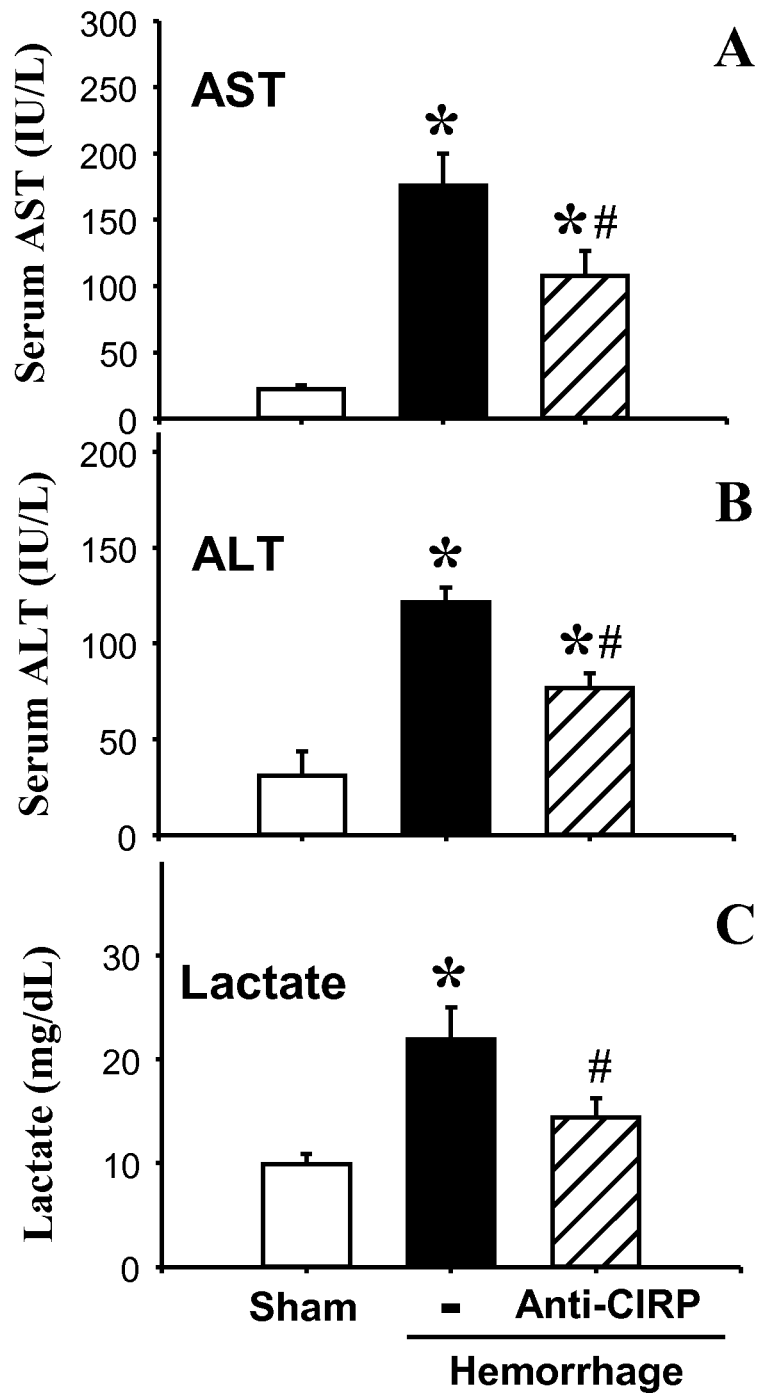
FIGS. 7A through 7C are graphs illustrating the reduction of serum AST, ALT, and lactate after administration of an anti-CIRP antibody composition in animals models of hemorrhage compared with untreated control.

Other biological activities of CIRP that can be measured to assess CIRP inhibition include AST levels in animal models, liver MPO levels in animal models and lactate levels in animal models. The levels of those markers are commonly elevated during an inflammatory response. Inhibitors of biological activities of CIRP can reduce the levels of one or more of these markers in animal models undergoing inflammatory response relative to untreated controls. Methods for assessing inhibition of the release of these markers by the CIRP inhibiting agent are given in FIG. 7A-C in Exemplification section. The inhibitory effects of anti-CIRP antibodies on AST levels, in an animal model of hemorrhage compared with untreated controls, is described in FIG. 7A. FIG. 8G depicts reduction of liver MPO levels by treatment with anti-CIRP antibodies in an animal model of hemorrhage compared with untreated controls. In FIG. 7B-C, the reduction of serum ALT and lactate by the anti-CIRP antibodies is given.

These methods can be performed in vivo, where an animal, e.g., a rat, is treated with the compound along with an agent that stimulates a proinflammatory cytokine cascade, and the effect of the agent on induction of the proinflammatory cytokine cascade is measured, e.g., by measuring serum TNF levels. However, due to the relative ease of doing these types of assays with cell cultures rather than with whole animals, in certain aspects the methods are performed in vitro, for example using macrophage cultures.

The present invention also relates to methods of treating a subject suffering from a cutaneous wound, comprising administering to the subject a CIRP inhibitor. In certain aspects of the invention, the CIRP inhibitor is an isolated peptide comprising an amino acid residue sequence of SEQ ID NO: 12 or a pharmaceutically acceptable salt thereof, or an amino acid residue sequence having at least 80%, or alternately 85%, 90%, 95%, 98%, 99% or 100% homology to SEQ ID NO: 12. In certain aspects of the invention, the CIRP inhibitor is a peptide comprising an amino acid residue sequence of SEQ ID NO. 13 or 14.

Methods of Therapy

As used herein, an "inflammatory disease or condition" refers to a disease or condition typified by increased inflammation in an individual. An inflammatory disease or condition also refers to an infectious disease or condition typified by increased inflammation in an individual. The inflammatory disease or condition can be a "chronic inflammatory disease or condition". A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. Alternatively, an inflammatory condition can be a consequence of an acute inflammatory episode. An "acute inflammatory episode," as used herein, refers to an increased innate immune response. Symptoms of acute inflammation include redness, heat, swelling, pain, and loss of function, e.g., loss of joint movement. For example, an acute inflammatory episode of a chronic inflammatory disease or condition differs from the typical symptoms of a chronic inflammatory disease or condition in the following ways. Frequently, during an acute inflammatory response the liver synthesizes acute phase proteins or acute phase reactants that are detectable in the blood stream. Acute phase reactants include C-reactive protein (CRP); alpha 1-antitrypsin; alpha 1-antichymotrypsin; alpha 2-macroglobulin; coagulation factors such as fibrinogen, fibrin, prothrombin, thrombin, factor VIII, and plasminogen; complement proteins, and serum amyloid protein. In addition, during an acute inflammatory episode, local inflammatory cells, e.g., neutrophils and macrophages, secrete a number of cytokines into the bloodstream, most notably IL-1, IL-6, IL-11, HMGB1 and TNF-alpha ("the cytokine cascade"). CIRP inhibitors may be administered to inhibit, reduce or otherwise ameliorate some or all of these agents and markers of inflammatory conditions.

Nonlimiting examples of inflammatory conditions which can be usefully treated using the present invention are selected from the group consisting of appendicitis, peptic, gastric and duodenal ulcers, peritonitis, pancreatitis, Crohn's disease, ulcerative colitis, ileus, epiglottitis, achalasia, cholangitis, cholecystitis, hepatitis, Whipple's disease, asthma, allergy, anaphylactic shock, immune complex disease, organ ischemia-reperfusion injury, organ necrosis, hay fever, sepsis, sepsis-septic scock, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, pneumonitis, pneumoultramicroscopic silicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, vasulitis, angiitis, endocarditis, arteritis, atherosclerosis, thrombophlebitis, pericarditis, myocarditis, ischemia, periarteritis nodosa, rheumatic fever, coeliac disease, adult respiratory distress syndrome, chronic obstructive pulmonary disease, meningitis, encephalitis, neuritis, neuralgia, spinal cord injury, paralysis, uveitis, arthritides, arthralgias, osteomyelitis, fasciitis, Paget's disease, gout, periodontal disease, arthritis, synovitis, myasthenia gravis, thryoiditis, systemic lupus erythematosus, allograft rejection, graft-versus-host disease, Goodpasture's syndrome, Behcets's syndrome, ankylosing spondylitis, Berger's disease, Retier's syndrome, Hodgkins disease, psoriasis, myocardial infraction, stroke, inflammatory bowel disease, necrotizing enterocolitis and trauma-hemorrhage.

In another embodiment, the inflammatory condition is selected from the group consisting of appendicitis, peptic, gastric and duodenal ulcers, peritonitis, pancreatitis, hepatitis, asthma, allergy, anaphylactic shock, organ necrosis, hay fever, sepsis, sepsis-septic shock, septicemia, endotoxic shock, Crohn's disease, ulcerative colitis, ileus, cachexia, septic abortion, disseminated bacteremia, coeliac disease, adult respiratory distress syndrome, chronic obstructive pulmonary disease, arthritis, systemic lupus erythematosus, allograft rejection, graft-versus-host disease, spinal cord injury, paralysis, psoriasis, ischemia-reperfusion of gut, liver, kidneys, heart, brain and limbs, myocardial infraction, stroke, inflammatory bowel disease, necrotizing enterocolitis and trauma-hemorrhage.

In another embodiment, the inflammatory condition is selected from the group consisting of peritonitis, pancreatitis, sepsis, sepsis-septic shock, endotoxic shock, Crohn's disease, ulcerative colitis, ileus, adult respiratory distress syndrome, chronic obstructive pulmonary disease, rheumatoid arthritis, systemic lupus erythematosis, ischemia-reperfusion of gut, liver, kidneys, heart, brain and limbs, myocardial infraction, stroke, inflammatory bowel disease, necrotizing enterocolitis, asthma and trauma-hemorrhage.

Alternatively, the inflammatory condition is selected from the group consisting of trauma-hemorrhage, sepsis-septic shock, ischemia-reperfusion of gut, liver, kidneys, heart, brain and limbs, myocardial infarction, stroke, inflammatory bowel disease and necrotizing enterocolitis.

In another embodiment, the present invention relates to a method of treating a subject suffering from a cutaneous wound, comprising administering to the subject an effective amount of a CIRP inhibitor. As used herein, a "cutaneous wound" is an injury at least to skin dermis, in which a portion of skin is torn, cut, punctured, or otherwise destroyed by any agent, including a blunt force, a chemical agent, or a bacterial infection. Examples of cutaneous wounds include chronic cutaneous wounds (skin ulcers), including chronic (non-healing) wounds in association with diabetes, bed sores, and bacterial or viral infection.

Modes of Administration

The route of administration of the CIRP inhibitor depends on the condition to be treated. For example, intravenous injection may be preferred for treatment of a systemic disorder such as septic shock, and oral administration may be preferred to treat a gastrointestinal disorder such as a gastric ulcer.

According to the method, one or more CIRP inhibitors of the present invention can be administered to the subject by an appropriate route, either alone or in combination with another drug. An effective amount of an agent (i.e. a CIRP inhibitor) is administered. An "effective amount" is an amount sufficient to achieve the desired therapeutic or prophylactic effect, under the conditions of administration, such as an amount sufficient for inhibition of an inflammatory response and alleviating or curing an inflammatory condition. The agents can be administered in a single dose or multiple doses. The dosage can be determined by methods known in the art and is dependent, for example, upon the particular agent chosen, the subject's age, sensitivity and tolerance to drugs, and overall well-being. Suitable dosages for antibodies can be from about 0.01 mg/kg to about 100 mg/kg body weight per treatment.

A variety of routes of administration are possible including, for example, oral, dietary, topical, transdermal, rectal, parenteral (e.g., intravenous, intraarterial, intramuscular, subcutaneous injection, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent (CIRP inhibitor) chosen, and the particular condition (e.g., disease) being treated. Intravenous, oral or parenteral administration are preferred.

The agent can be administered as a neutral compound or as a pharmaceutically acceptable salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

As used herein, a "pharmaceutically acceptable salt" of a disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates (e.g. (+)- tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The agent can be administered to the individual as part of a pharmaceutical composition comprising an inhibitor of CIRP and a pharmaceutically acceptable carrier.

As used herein, a "pharmaceutical composition" is a formulation comprising the disclosed CIRP antagonist (such as an anti-CIRP antibody) and a pharmaceutically acceptable diluent or carrier, in a form suitable for administration to a subject. Suitable pharmaceutically acceptable carriers include inert solid fillers or diluents and sterile aqueous or organic solutions. Formulation will vary according to the route of administration selected (e.g., solution, emulsion, capsule). Suitable pharmaceutical carriers can contain inert ingredients which do not interact with the promoter (agonist) or inhibitor (antagonist) of CIRP. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration.

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In certain embodiments of the disclosed methods, the subject is human.

In some embodiments of the invention, the CIRP inhibitor is administered during fluid resuscitation of a subject. As used herein, "fluid resuscitation" or "fluid replacement" means replenishment of bodily fluid lost through bleeding, sweating, fluid shifts, or pathologic processes. Fluid resuscitation occurs via intravenous administration, alternately oral or rectal administration, or further alternately via injection of fluid into subcutaneous tissue.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Specific embodiments of the invention are described in the following Examples. Other embodiments within the scope of the claims herein will be apparent to one skilled in the art from consideration of the specification or practice of the invention as disclosed herein. It is intended that the specification, together with the Examples, be considered exemplary only, with the scope and spirit of the invention being indicated by the Claims which follow the Examples.

EXEMPLIFICATION

Example 1: Native CIRP Mediates Inflammatory Response Induced by Hemorrhagic Shock in Animal Model Elevated levels of CIRP were detected in tissues and serum of animals in hemorrhagic shock models.

Materials and Methods

Experimental Animals:

Male Sprague-Dawley rats (275-325 g in body weight) were obtained from Charles River Laboratories (Wilmington, Mass.), and were housed in a temperature-controlled room on a 12-h light/dark cycle and fed on a standard Purina rat chow diet. Prior to the induction of hemorrhage shock, rats were fasted overnight but allowed water ad libitum. All experiments were performed in accordance with the guidelines for the use of experimental animals by the National Institutes of Health (Bethesda, Md.) and were approved by the Institutional Animal Care and Use Committee (IACUC) at the Feinstein Institute for Medical Research.

Animal Model of Hemorrhage Shock:

The model of hemorrhage shock used in this experiment was described in detail previously with minor modification (Wang P, Hauptman J G, Chaudry I H: Hemorrhage produces depression in microvascular blood flow which persists despite fluid resuscitation. *Circ Shock* 32:307-318, 1990; Wu R, Dong W, Zhou M, Cui X, Simms H H, Wang P: A novel approach to maintaining cardiovascular stability after hemorrhagic shock: beneficial effects of adrenomedullin and its binding protein. *Surgery* 137:2005). Briefly, rats were anesthetized with isoflurane inhalation. Catheters (PE-50 tubing) were placed in femoral veins and arteries after carefully separating the femoral nerve and blood vessels. The femoral artery on the opposite side was also catheterized. One arterial catheter was used for monitoring the mean arterial pressure (MAP) and heart rate (HR) via a blood pressure analyzer (Digi-Med, Louisville, Ky.), the other was for blood withdrawal and the venous catheter was used for fluid resuscitation. The rat was bled to an MAP of 25-30 mm Hg within 10 min. This pressure was maintained for 90 min by further withdrawal of small volumes of blood or provision of small volumes of lactated Ringer's solution. At the end of this hypotensive period, the rats were then resuscitated with lactated Ringer's solution (equivalent 2 times) the maximum bleed-out volume, which was approximately 60% of calculated blood volume) over a 60-min period. The shed blood was not used for resuscitation and the animals were not heparinized prior to, during, or following hemorrhage. After 4 h, blood samples were collected and placed on ice to allow clotting. The samples then were centrifuged at 1200 g for 10 min at 4° C., and the serum samples were stored at −80° C. until assayed. Tissues samples were also collected and saved to liquid nitrogen immediately, then stored at −80° C. until assayed. Sham-operated animals underwent the same surgical procedure but were neither bled nor resuscitated.

Determination of CIRP Gene Expression:

To examine whether the expression of the CIRP gene was altered in hemorrhage, hemorrhagic tissues were determined and quantified by real-time reverse transcription-polymerase chain reaction (RT-PCR). Q-PCR was carried out on cDNA samples reverse transcribed from 4 µg RNA using murine leukemia virus reverse transcriptase (Applied Biosystems). Using the QuantiTect SYBR Green PCR kit (Qiagen, Valencia, Calif.), reactions was carried out in 24 µl final volumes containing 2 pmol of forward and reverse primers, 12 µl QuantiTect Master Mix, and 1 µl cDNA. Amplification was performed according to Qiagen's recommendations with an Applied Biosystems 7300 real-time PCR. Expression amount of rat G3PDH mRNA was used for normalization of each sample, and analysis of each specific mRNA was conducted in duplicate. Relative expression of mRNA was calculated by the ΔΔCt-method, and results expressed as fold change with respect to the corresponding experimental control. The following rat primers were used: CIRP (NM_031147): 5'-GGG TCC TAC AGA GAC AGC TAC GA-3' (forward), (SEQ ID NO: 4), 5'-CTG GAC GCA GAG GGC TTT TA-3' (reverse), (SEQ ID NO: 5); G3PDH (XM_579386): 5'-ATG ACT CTA CCC ACG GCA AG-3' (forward), (SEQ ID NO: 6), 5'-CTG GAA GAT GGT GAT GGG TT-3' (reverse), (SEQ ID NO: 7). Gene expression of TNF-α was assessed using RT-PCR. The primers for TNF-α and housekeeping genes were as follows: rat TNF-α, 5'-CCC AGA CCC TCA CAC TCA GA-3', (SEQ ID NO: 8), 5'-GCC ACT ACT TCA GCA TCT CG-3'(SEQ ID NO: 9) and G3PDH, 5'-TGA AGG TCG GTG TCA ACG GAT TTG GC-3' (SEQ ID NO: 10), 5'-CAT GTA GGC CAT GAG GTC CAC CAC-3' (SEQ ID NO: 11) as previously described (Wu R, Zhou M, Wang P: Adrenomedullin and adrenomedullin binding protein-1 downregulate TNF-alpha in macrophage cell line and rat Kupffer cells. *Regul Pept* 112:19-26, 2003).

RT-PCR Assay:

Total RNAs were extracted by Trizol (Invitrogen). The cDNA was synthesized using MLV reverse transcriptase (Applied Biosystems, Grand Island, N.Y.). PCR reaction was performed in QuantiTect SYBR Green PCR mixture (Qiagen, Valencia, Calif.), and analyzed by the Applied Biosystems 7300 PCR System. GAPDH was used as an internal control for normalization and the relative expression level of the analyzed gene was calculated by the ΔΔCt-method. Each sample was measured in duplicates. The primers used for RT-PCR were synthesized from Operon (Huntsville, Ala.). The primers are listed as following: rat CIRP (NM_031147), 5'-GGG TCC TAC AGA GAC AGC TAC GA-3' (forward), (SEQ ID NO: 4) and 5'-CTG GAC GCA GAG GGC TTT TA-3' (reverse), (SEQ ID NO: 5); TNF-α (NM_012675), 5'-CCC AGA CCC TCA CAC TCA GA-3' (forward), (SEQ ID NO: 8), 5'-GCC ACT ACT TCA GCA TCT CG-3'(reverse), (SEQ ID NO: 9); and GAPDH (NM_017008), 5'-ATG ACT CTA CCC ACG GCA AG-3' (forward), (SEQ ID NO: 6), 5'-CTG GAA GAT GGT GAT GGG TT-3' (reverse), (SEQ ID NO: 7).

Western Blot Analysis:

Expression of CIRP protein in the serum and tissue were determined using rabbit polyclonal antibody against CIRP (ProteinTech Group, Chicago, Ill.) by western blot analysis. Briefly, equal amounts of serum (volume) and tissue homogenates (protein mg/lane) were fractionated on 4-12% NuPAGE Bis-Tris gels (Invitrogen, Carlsbad, Calif.) and transferred to nitrocellulose membrane, then were blocked by incubation in TBST buffer (10 mM Tris-HCl [pH 7.5], 150 mM NaCl, 0.1% Tween 20) containing 5% nonfat dry milk for 1 h room temperature. The membrane was incubated with rabbit polyclonal antibodies overnight at 4° C. Following several times washed in TBST buffer and incubated with horseradish peroxidase-linked anti-rabbit IgG (Cell Signaling Technology, Danvers, Mass.), a chemiluminescent peroxidase substrate (ECL; GE Healthcare Bio-Sciences, Piscataway, N.J.) was applied according to the manufacturer's instructions, and the membranes were exposed to X-ray film. Western blots results were scanned and the relative band intensity was quantified by using the GS800 Calibrated Densitometer, Bio-Rad Image Analysis Systems (Hercules, Calif.). Anti-β-actin antibody (for cytoplasmic protein, Santa Cruz Biotechnology) was used to ensure equal loading. The levels of HMGB1 in rat serum were measured using rabbit polyclonal anti-HMGB1 antibody as previously described (Wang H, Bloom O, Zhang M, Vishnubhakat J M, Ombrellino M, Che J, Frazier A, Yang H, Ivanova S, Borovikova L, Manogue K R, Faist E, Abraham E, Andersson J, Andersson U, Molina P E, Abumrad N N, Sama A, Tracey K J: HMG-1 as a late mediator of endotoxin lethality in mice. *Science* 285:248-251, 1999).

Alternately, tissue samples were homogenized in RIPA buffer (10 mM Tris-HCl pH 7.5, 120 mM NaCl, 1% NP-40, 1% sodium deoxycholate, and 0.1% SDS) containing a protease inhibitor cocktail (Roche, Indianapolis, Ind.). Protein concentration was determined by DC protein assay (Bio-Rad, Hercules, Calif.). Equal amounts of serum or tissue homogenates were fractionated on SDS-PAGE and transferred to nitrocellulose membrane. The membrane was incubated with antibodies to CIRP (#10209-2-AP; Protein-Tech, Chicago, Ill.), GAPDH (#sc-25778; Santa Cruz, Santa Cruz, Calif.), histone (#9715; Cell Signaling, Danvers, Mass.), Bax (#sc-526; Santa Cruz), actin (#A5441; Sigma-Aldrich, St. Louis, Mo.), cathepsin D (#sc-10725; Santa Cruz), or HMGB1 (#ab18256; Abcam, Cambridge, Mass.), followed by secondary antibody-horseradish peroxidase conjugate (SouthernBiotech, Birmingham, Ala.) and developed with a chemiluminescence detection kit (GE Healthcare).

Statistical Analysis:

All data are expressed as mean±s.e.m. and compared by one-way analysis of variance (ANOVA) and Student-Newman-Keuls' method. Student's t-test was used for two-group analysis. Majority of data sets passed the normality test. Some data sets had a statistical difference in the variation between the groups. The survival rate was estimated by Kaplan-Meier method and compared the log-rank test. Differences in values were considered significant if $P<0.05$.

Results

Figure 9:
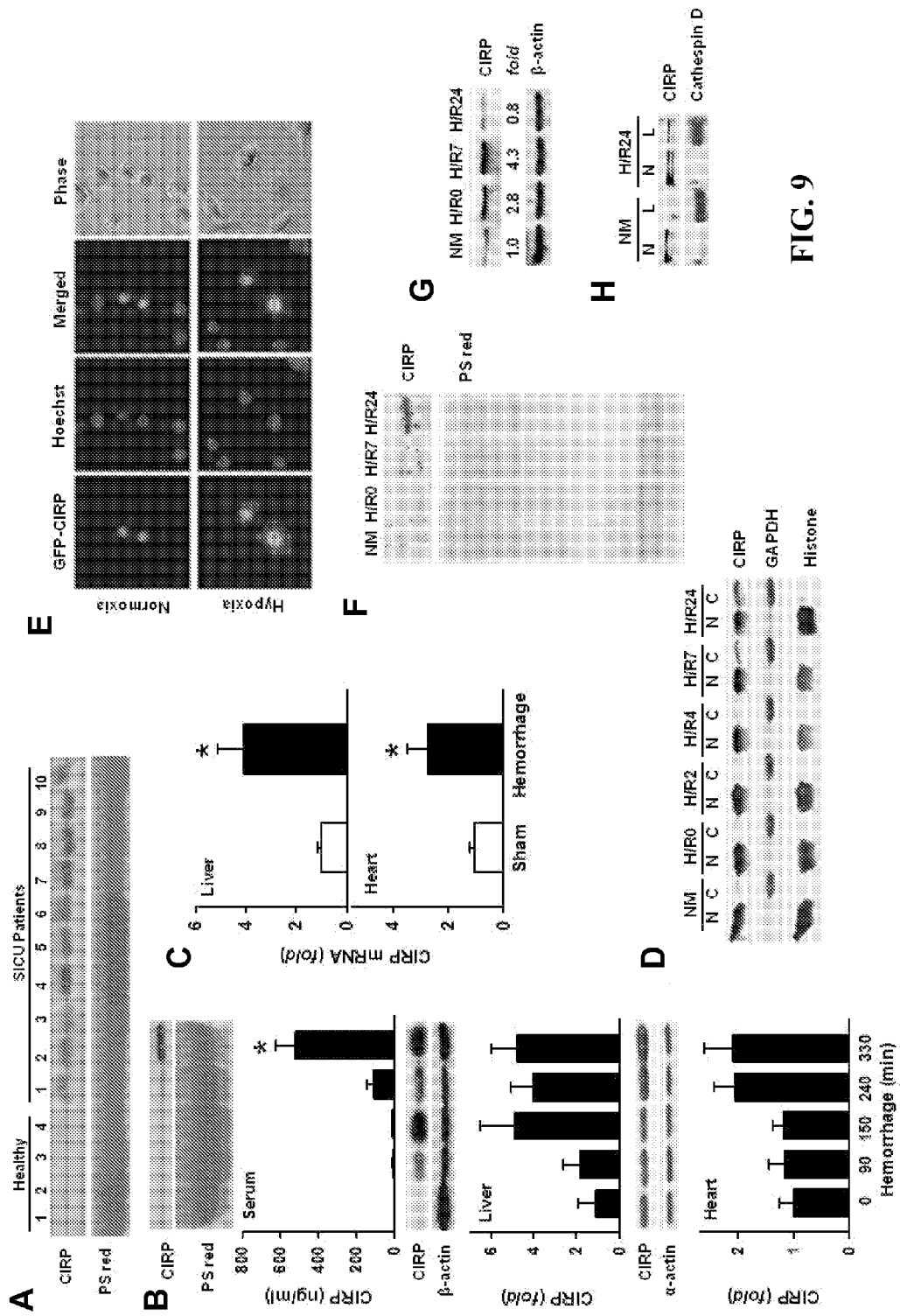
FIG. 9A is a photograph of a Western blot detecting the level of CIRP in blood serum samples taken from either healthy volunteers or surgical intense care unit (SICU) patients suffering from shock.
FIG. 9B is a photograph of a Western blot detecting CIRP level in serum and tissue samples taken from rats post-hemorrhage.
FIG. 9C shows bar plots indicating upregulation of CIRP transcription in tissues of hemorrhaged animals at 240 min post-hemorrhage.
FIG. 9D through 9H illustrate the effect of hypoxia on cell lines.

Upregulation and Release of CIRP in Tissues and in Circulation in Hemorrhaged Animals:

Rats that underwent an experimental blood loss (hemorrhage) showed significantly increased expression of CIRP mRNA in various tissues. CIRP expression increased by about 5 fold in the liver (FIG. 2A) and about 3 fold in the heart (FIG. 2B) as compared to sham-operated controls. High circulating levels of CIRP protein were detected by Western blot analysis in the hemorrhagic rats. The hemorrhage group showed a clear immunoreactive CIRP band, which was not found in sham group (FIG. 2C). The expression of CIRP protein also increased in the heart of the hemorrhaged animals (FIG. 2D), compared with sham-operated rats (β-actin was to ensure equal loading). A rat model of hemorrhagic shock was used by bleeding the animals to a mean arterial pressure (MAP) of 25-30 mmHg and maintaining that MAP for 90 min, followed by fluid resuscitation. Serum CIRP was detectable at 240 min and was found to be significantly elevated at 330 min post-shock in hemorrhaged rats. CIRP protein levels started to increase at 150 and 240 min in the liver and heart, respectively. Serum CIRP concentration was estimated using serial dilutions of purified CIRP as standard. Data are mean±s.e.m., n=4-6/time-point, *P<0.05 vs. time 0. (FIG. 9B and FIG. 2C). Correspondingly, CIRP mRNA levels were significantly induced in the liver and heart at 240 min post-shock by 4.1 and 2.8-fold, respectively. These levels were analyzed by real time RT-PCR. Data are mean±s.e.m., n=6/group, *P<0.05 vs, sham (FIG. 9C and FIGS. 2A and B).

Example 2: Native CIRP Mediates Inflammatory Response Induced by Hemorrhagic Shock in Humans Elevated serum levels of CIRP were detected in humans suffering from hemorrhagic shock.
Materials and Methods
  Human Blood Specimens:
  Blood samples were obtained from patients admitted to the surgical intense care unit (ICU) with hemorrhagic shock. Serum was separated and stored in aliquots at −80° C. Informed consent and human subject protocols were approved by the Institutional Review Board (IRB) of the North Shore-Long Island Jewish Health System.
Results
  Detection of Serum CIRP in Surgical ICU Patients with Shock:
  To explore the role of CIRP in clinical conditions, the serum CIRP levels from 10 surgical ICU patients (Table 1) was examined. There were five females and five males and the average age was 71 years old. The Acute Physiology and Chronic Health Evaluation II (APACHE II) ranged from 13 to 25 and averaged 19. The average blood sample collection time was 43 h after the onset of shock, which was defined by a clinically documented systolic blood pressure <90 mmHg either during active hemorrhage or following a traumatic insult. Serum CIRP was well detected in all 10 patients regardless of differences in clinical parameters, while being hardly observed in healthy volunteers (FIG. 9A).

TABLE 1

Clinical Parameters of Patients Admitted to the Surgical Intensive Care Unit

| Gel Lane | Age | Sex | APACHE II | Hour* | Initiating Clinical Events |
|---|---|---|---|---|---|
| 1 | 81 | F | 18 | 52 | Intra-operative hemorrhage during vascular bypass surgery |
| 2 | 76 | M | 23 | 64 | Ruptured hepatic hemangioma |
| 3 | 88 | F | 21 | 24 | Massive lower gastro-intestinal bleeding |
| 4 | 75 | F | 19 | 61 | Post-operative hemorrhage following total abdominal hysterectomy and bilateral salpingo-oophorectomy |
| 5 | 57 | M | 15 | 41 | Pelvic fracture, splenic laceration and scalp laceration after pedestrian struck by car |
| 6 | 89 | M | 25 | 60 | Gross hematuria from bladder tumor |
| 7 | 27 | M | 17 | 23 | Pelvic fracture and splenic laceration from motorcycle accident |
| 8 | 67 | M | 23 | 66 | Ruptured abdominal aortic aneurysm |
| 9 | 85 | F | 13 | 27 | Retroperitoneal hemorrhage following diagnostic angiogram |
| 10 | 65 | F | 16 | 12 | Hemorrhage from tracheostomy site |
| Avg | 71.0 | 5F/5M | 19.0 | 43.0 | |

*hour after the onset of shock

Example 3: CIRP is Secreted from Cell Lines Exposed to Hypoxia

CIRP was secreted from cells subjected to hypoxic conditions. After reoxygenation, CIRP translocated from the nucleus to the cytoplasm, then from the cytoplasm to the extracellular matrix.
Materials and Methods
  Cell Culture:
  Murine macrophage-like RAW 264.7 cells were obtained from ATCC (American Type Culture Collection, Manassas, Va.), and were grown in Dulbecco's Modified Eagle's Medium (DMEM, Life Technologies, Grand Island, N.Y.) containing 10% (vol/vol) FBS (heat-inactivated at 56° C. for 30 min), 100 U/ml penicillin, 100 µg/ml streptomycin and 2 mM glutamine. Cells were re-suspended in medium and incubated in 6 or 48-well tissue-culture plates overnight in a humidified incubator (37° C., 5% $CO_2$). In the experiments, cell monolayers were stimulated with or without recombinant CIRP at various indicated concentrations and for various indicated times. The cell-free supernatants were assayed for TNF-α by ELISA or for HMGB1 by western blot analysis.
  In Vitro Hypoxia:
  Hypoxia was produced using a sealed chamber containing 1% $O_2$, 5% $CO_2$, and 94% $N_2$ placed in an incubator at 37° C. Culture medium was changed to Opti-MEM I medium (Invitrogen) before subjecting to hypoxia. After 20 h incubation in the hypoxic chamber, cells were recovered at normal culture condition for different time periods and collected for further analyses.
  Cell Fractionation:
  For isolation of cytoplasmic and nuclear fractions, RAW 264.7 cell pellets were resuspended in buffer containing 10 mM HEPES/KOH pH 7.9, 1.5 mM $MgCl_2$, 10 mM KCl, 0.5 mM dithiothreitol, and a protease inhibitor cocktail on ice for 15 mM. After centrifugation, the supernatant was collected as cytoplasmic fraction and the pellet was resuspended in buffer containing 20 mM HEPES/KOH pH 7.9, 25% glycerol, 420 mM NaCl, 1.5 mM $MgCl_2$, 2 mM EDTA, 0.5 mM dithiothreitol, and a protease inhibitor cocktail on ice for 20 min. After centrifugation, the supernatant was collected as nuclear fraction. The isolation of lysosome was performed with a kit as instructed by Thermo Scientific (Waltham, Mass.).

Expression of GFP-CIRP Fusion Protein:

The construction of GFP-CIRP expression plasmid is described in Nishiyama et al. (Nishiyama, H., et al. A glycine-rich RNA-binding protein mediating cold-inducible suppression of mammalian cell growth. *J. Cell Biol.* 137, 899-908 (1997)). RAW 264.7 cells were transfected with the plasmid using LipofectAMINE reagent (Invitrogen). Cells were also transfected with a GFP expression plasmid alone as control for the comparison. The release of CIRP in cultured cells was investigated. The conditioned medium from normoxic or hypoxic/reoxygenated RAW 264.7 cells was incubated with 0.02% deoxycholic acid and 10% trichloroacetic acid at 4° C. overnight for protein precipitation, and it was then subjected to Western blotting. LDH activity was determined by an assay kit from Pointe Scientific.

Results

Figure 15:
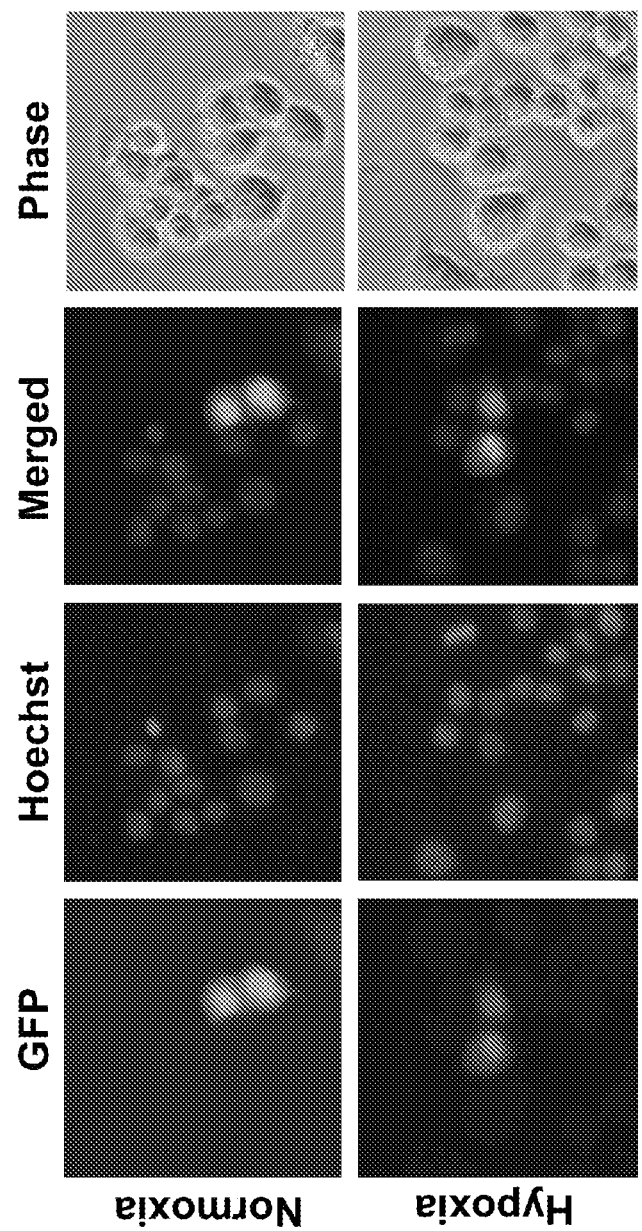
FIG. 15 shows fluorescence microscopy photograph of RAW 264.7 cells demonstrating a hypoxia/reoxygenation-induced CIRP translocation from the nucleus to the cytoplasm.

Translocation and Release of CIRP from Macrophages Exposed to Hypoxia:

Since CIRP was detectable in the serum of both humans and rats after shock, the mode of CIRP release was investigated. Macrophages are the major cell population responsible for the release of various inflammatory mediators. Murine macrophage-like RAW 264.7 cells were cultured in normoxia (NM) or subjected to hypoxia (1% $O_2$) for 20 h in the similar manner in which it occurs during hemorrhagic shock, and the cellular location of CIRP was examined. The cells exposed to hypoxia were reoxygenated for 0, 2, 4, 7, or 24 h (H/R0, H/R2, H/R4, H/R7, or H/R24). Cell extract was fractionated to the nuclear (N) and cytoplasmic (C) components, and then subjected to Western blotting. The integrity of each fraction was verified using anti-GAPDH and anti-histone antibodies. CIRP was primarily located in the nucleus during normoxic conditions, whereas cytoplasmic CIRP was detected at 7 h and markedly increased at 24 hours after reoxygenation from 20-hour hypoxia determined by biochemical fractionation (FIG. 9D). A genetic approach was also used to confirm the translocation of CIRP. In a control experiment in which RAW 264.7 cells were transfected with a green fluorescence protein (GFP) expression plasmid, green fluorescence was observed all over the cell in both normoxic and hypoxic conditions (FIG. 15). In contrast, when RAW 264.7 cells were transfected with a GFP-CIRP expression plasmid, green fluorescence was only observed in the center of the cell, while being overlapped by blue fluorescence from Hoechst nuclei staining under normoxia (FIG. 9E). However, at 4 hours after reoxygenation from hypoxia, green fluorescence was distributed throughout both the nucleus and cytoplasm (FIG. 9E). Taken together, hypoxia/reoxygenation induced CIRP translocation from the nucleus to the cytoplasm in macrophages.

To examine whether cytoplasmic CIRP could be released into the extracellular space, in a conditioned medium (CM) of RAW 264.7 cells precipitated by trichloroacetic acid, CIRP was well detected at 24 h reoxygenation after hypoxia, while it was undetectable in normoxia by Western blotting (FIG. 9F). Furthermore, the intracellular CIRP protein level increased by 2.8-fold immediately after hypoxia and 4.3-fold after 7 h of reoxygenation, while its level was reduced at 24 h of reoxygenation in cell cysate due to its release into the extracellular space (FIGS. 9F and 9G). In FIG. 9G, the fold change in the middle of the images indicates the relative intensity. CIRP release was not attributed to necrosis since there was no change in lactate dehydrogenase activity and no detectable intracellular Bax protein in CM after hypoxia.

The CIRP protein sequence does not contain a secretion leader signal; therefore, its secretion should not be through the classical (endoplasmic reticulum-Golgi-dependent) pathway (Qu, Y. & Dubyak, G. R. P2X7 receptors regulate multiple types of membrane trafficking responses and non-classical secretion pathways. *Purinergic Signal.* 5, 163-173 (2009)). A potential mechanism of active CIRP release was identified by conducting a biochemical fractionation to isolate the lysosomal compartment of RAW 264.7 cells undergoing hypoxia/reoxygenation. As shown in the Western blot of cell extract from RAW 264.7 cells, CIRP protein was not detected in lysosomes of cells cultured in normoxia (NM), while it was co-localized with cathespin D, a protein maker of lysosomes, at 24 h reoxygenation from hypoxia (H/R24) (FIG. 9H; N=nuclear; L=lysosomal fractionated components of cell extract). This result indicated that CIRP could be released by the lysosomal secretion. Images represent three independent experiments in FIGS. 9D through 9H.

Example 4: Treatment of Cell Lines and Animals with Exogenous Recombinant CIRP Induces Inflammatory Response As measured by release of inflammatory cytokines and organ injury markers, an increased inflammatory response was observed in murine and human cell lines, as well as in healthy animals, after administration of rCIRP.

Materials and Methods

Recombinant Protein (rCIRP):

A serial method for expression and purification of recombinant proteins with a hexahistidine tag (His-tag) from bacterial expression systems was used. The cDNA was prepared by reverse transcribing 4 μg of total tissue RNA of rat heart using a modified oligo d ($T_{16}$) primer with 50 U MuLV reverse transcriptase as described previously (Dwivedi A J, Wu R, Nguyen E, Higuchi S, Wang H, Krishnasastry K, Marini C P, Ravikumar T S, Wang P: Adrenomedullin and adrenomedullin binding protein-1 prevent acute lung injury after gut ischemia-reperfusion. *J Am Coll Surg* 205:284-293, 2007). To obtain CIRP protein, the CIRP coding sequence was amplified by PCR from CIRP cDNA with a primer set: sense 5'-CAC CAT GGC ATC AGA TGA AGG-3' (SEQ ID NO: 2) and antisense 5'-CTC GTT GTG TGT AGC ATA GC-3' (SEQ ID NO: 3) were synthesized (design according to GenBank: NM_031147, NCBI) and used to isolate the rat CIRP clone. The PCR product was then digested with EcoRV and NotI and cloned into pENTR vector, the C-terminal hexahistidine tag (His-tag) system (as described by Invitrogen), and then transformed to *E. coli* BL21 (DE3), as a resulting expression plasmid. Induced expression of CIRP performed in several liters of BL21 (DE3) cell cultures and then CIRP was isolated and purified as described by the manufacturer (Novagen, Madison, Wis.). To avoid any inadvertent lipopolysaccharide (LPS) contamination, Triton X-114 extraction was used to remove possible endotoxin contamination, and final LPS content was determined using the Limulus amebocyte lysate (LAL) assay (BioWhittaker Inc, Walkersville, Md.) as described previously (Ertel W, Morrison M H, Wang P, Ba Z F, Ayala A, Chaudry I H: The complex pattern of cytokines in sepsis.

Association between prostaglandins, cachectin, and interleukins. *Ann Surg* 214:141-148, 1991).

Construction of CIRP Expression Plasmid:

Rat CIRP cDNA (NM_031147) was synthesized from total RNA isolated from rat heart by using MLV reverse transcriptase with oligo d($T_{16}$) primers. The cDNA was amplified with oligonucleotide primers, sense 5'-CAC CAT GGC ATC AGA TGA AGG-3' and antisense 5'-CTC GTT GTG TGT AGC ATA GC-3'. The resulting PCR product was digested with EcoRV and NotI and cloned into pENTR vector (Invitrogen) at the C-terminus of hexahistidine tag (His-tag) and then transformed to *E. coli* BL21 (DE3). Individual clones were selected by kanamycin resistance.

Purification of rmCIRP:

Transformed *E. coli* carrying rat His-CIRP expression plasmid were inoculated in Luria-Bertani medium containing kanamycin overnight and induced with 1.0 mM IPTG for another 6 h. The bacteria were harvested by centrifugation and the pellet was washed once with 20 mM Tris-HCl pH 7.9. Bacterial pallet was resuspended in buffer containing 20 mM Tris-HCl pH 7.9, 500 mM NaCl, and 5 mM imidazole, and lysed by sonication at 4° C. The soluble extract was clarified by centrifugation at 20,000 g at 4° C. for 1 h. The clear lysate was loaded onto a $Ni^{2+}$-NTA column (Novagen, Madison, Wis.). The bound protein was washed with 20 mM Tris-HCl pH 7.9, 500 mM NaCl, and 100 mM imidazole, and was eluted in the same buffer supplemented with 1.0 M imidazole. All proteins were dialyzed with PBS and stored at −80° C. for further analysis.

Removal of LPS from the Purified rmCIRP Preparation:

Triton X-114 (Sigma-Aldrich, St. Louis, Mo.) was added to the purified protein solution to a final concentration of 5%. The mixture was rotated at room temperature for 15 min to ensure a homogenous solution. Then, the mixture was centrifuged at 14,000 g for 12 min. The upper aqueous phase containing rmCIRP (LPS free) was carefully removed. The level of LPS in the removed solution was measured by Limulus amebocyte lysate (LAL) assay (Cambrex, East Rutherford, N.J.).

Figure 16:
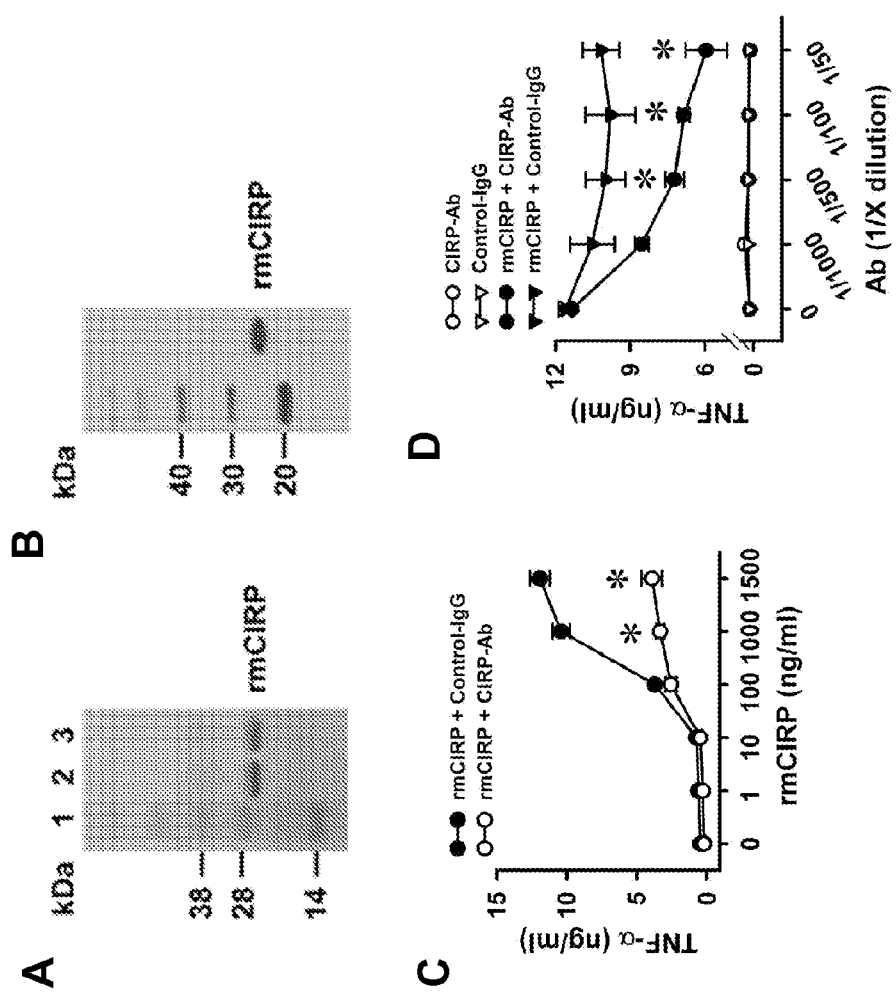

Validation of the Purified rmCIRP:

After expression and purification, 1 µg of protein preparation was subjected to SDS-PAGE and the gel was stained with Coomassie blue. Lane 1, protein marker; Lane 2, batch A; Lane 3, batch B. The purity of rmCIRP preparation was examined by SDS-PAGE, showing a major band at 24 kDa and very minor bands at other positions (FIG. 16A). The identity of rmCIRP was further confirmed by Western blotting against anti-CIRP antibodies from two different sources, one generated from in the laboratory and the other from ProteinTech (FIG. 16B). The purified rmCIRP was further validated by amino acid sequence analysis using LC-MS/MS at the Proteomics Resource Center of the Rockefeller University, New York. The recombinant protein was identified as CIRP with >95% confidence using the MASCOT database search algorithm.

Cell Culture:

RAW 264.7 cells were cultured as described in Example 3.

Inflammatory Cytokine Assay:

As an index of the inflammatory cytokine cascade and the acute inflammatory response, supernatants from cells incubated with recombinant CIRP were measured for TNF-α and IL-6 levels in serum, tissue homogenates, and culture medium grown with macrophages using a commercially available enzyme-linked immunosorbent assay (ELISA) kits (BioSource International, Camarillo, Calif.) according to the manufacturer's instruction. To quantify TNF-α and IL-6 protein levels in serum and tissue, serum samples were harvested 4 h after hemorrhage, or 4 h after treatment with recombinant CIRP from animals by cardiac puncture at the time that the rats were sacrificed, and collected tissue samples, and carried out by the same method as above. HMGB1 levels were determined by Western blotting.

Determination of Serum Levels of Transaminases and Lactate:

Serum concentrations of aspartate aminotransferase (AST), alanine aminotransferase (ALT), and lactate were determined by using assay kits according to the manufacturer's instructions (Pointe Scientific, Lincoln Park, Mich.).

Isolation of Human PBMC:

Human PBMCs were isolated from blood obtained from healthy donors at the New York Blood Bank by centrifugation over a Ficoll-Paque Plus (GE Healthcare, Port Washington, N.Y.) density gradient according to standard protocols. Isolated cells were washed with RPMI1640 complete medium and cultured on a plate. After 2 h, the non-adherent cells were removed and attached cells were cultured overnight before use.

Results

Recombinant CIRP (rCIRP) Induced Inflammatory Responses in Murine Cell Line:

To address whether the extracellular CIRP could function as an inflammatory mediator, recombinant murine CIRP (rmCIRP) was expressed and purified using a bacterial expression system with more than 97% purity and confirmation by Western blotting (FIGS. 16A and B). A Triton X-114 extraction procedure was applied to remove lipopolysaccharide (LPS)(see Aida, Y. & Pabst, M. J. Removal of endotoxin from protein solutions by phase separation using Triton X-114. *J. Immunol. Methods* 132, 191-195 (1990)) from purified rmCIRP with residual about 10 pg LPS/µg CIRP measured by the Limulus amebocyte lysate assay, which is comparable to that described in other identified endogenous DAMPs (see Wang, Y., et al. Identification of stimulating and inhibitory epitopes within the heat shock protein 70 molecule that modulate cytokine production and maturation of dendritic cells. J. Immunol. 174, 3306-3316 (2005); Henderson, B., et al. The extracellular signaling actions of molecular chaperones are not due to microbial contaminants. *Cell Stress Chaperones* 15, 123-141 (2010)). Addition of rmCIRP to RAW 264.7 cells increased TNF-α release in a dose- and time-dependent manner (See FIGS. 10A and 10B). RAW 264.7 cells were incubated with indicated concentrations of rmCIRP for 4 h (FIG. 10A) or 100 ng/ml rmCIRP for the indicated times (FIG. 10B), wherein *P<0.05 vs. no rmCIRP or time 0.

Figure 10:
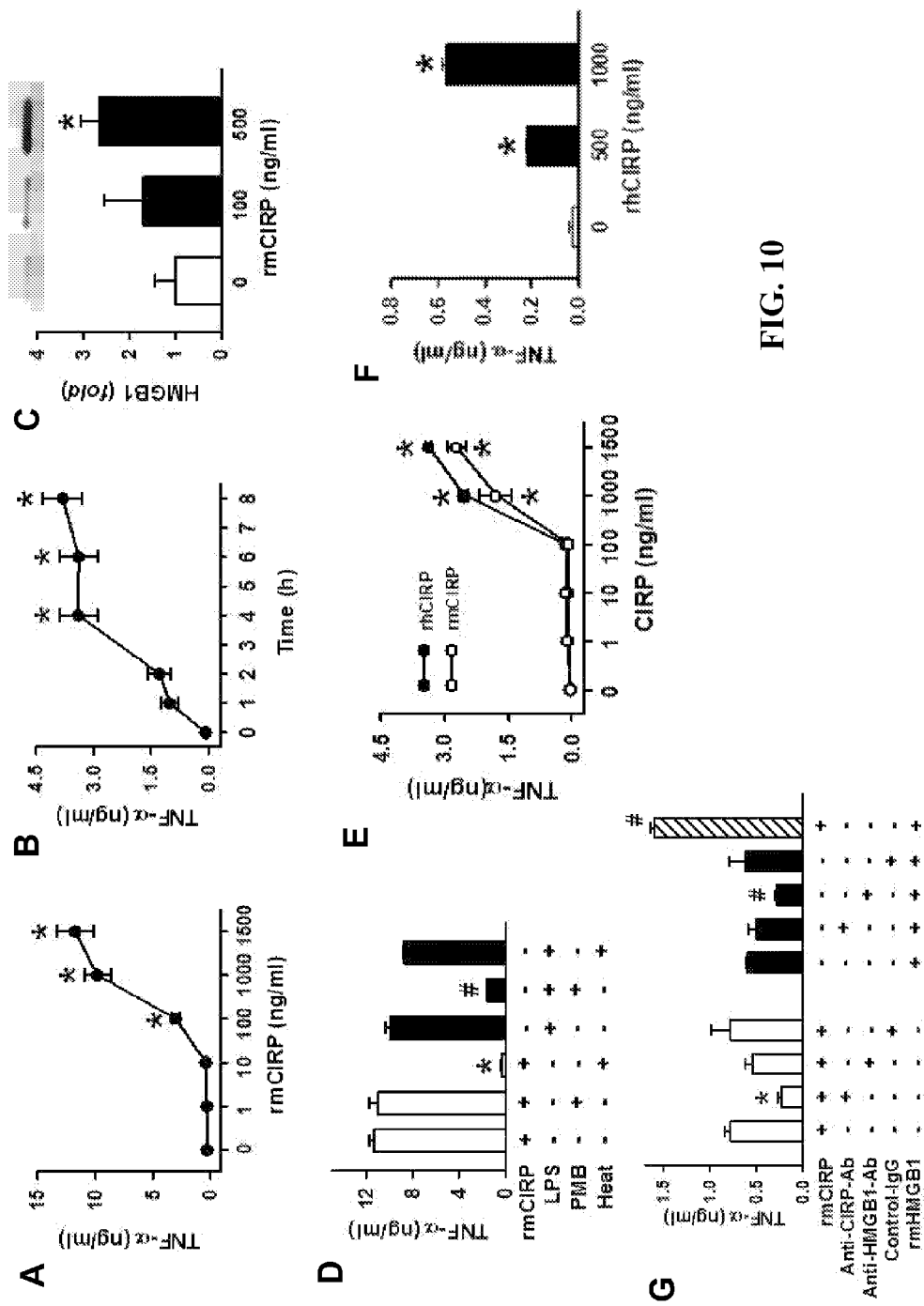
FIGS. 10A, 10B, and 10D through 10F are graphs illustrating the effect of rCIRP on cytokine release in various cell lines.
FIG. 10C is a bar plot illustrating the induction of serum level of HMGB1 following administration of rmCIRP to rats.
FIG. 10G is a bar plot demonstrating the effect of pre-incubation of human THP-1 cells with anti-CIRP antibody prior to the exposure to CIRP on the release of TNF alpha.
Figure 17:
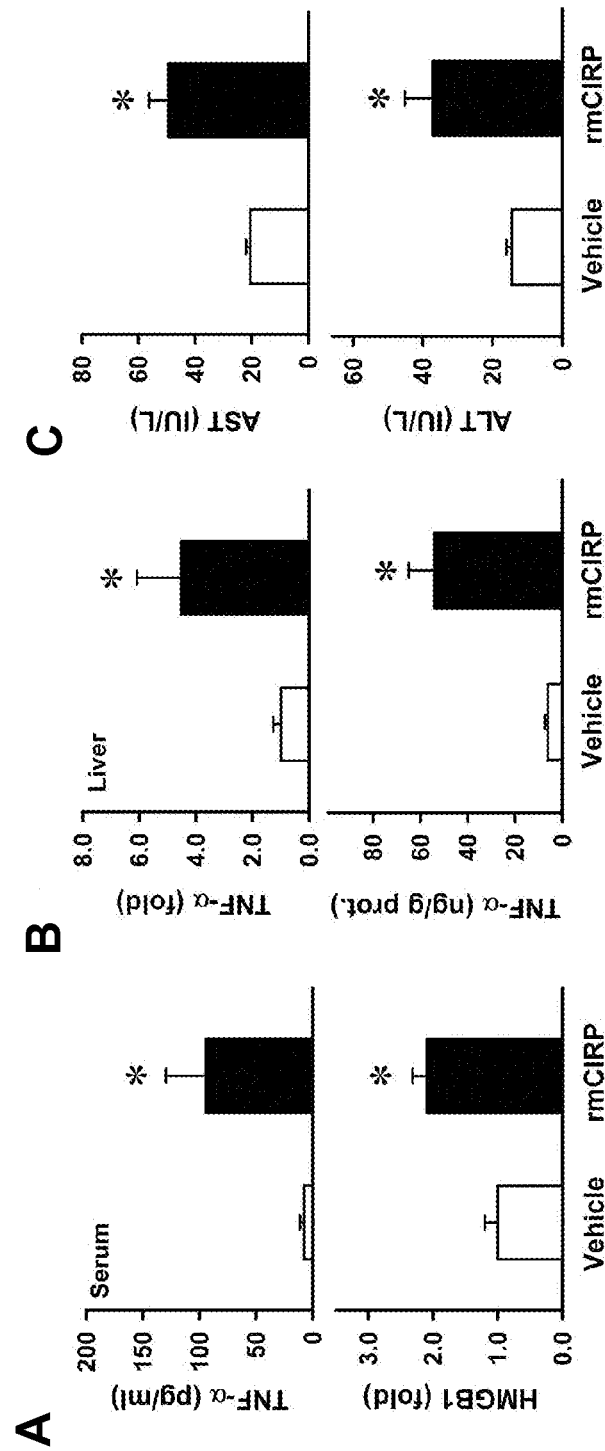
FIGS. 17A through 17C demonstrate that the recombinant CIRP (rCIRP) induced inflammatory responses in healthy rats.

Recombinant CIRP (rCIRP) Induced Inflammatory Responses in Healthy Rats:

Healthy rats were intravenously administered rmCIRP (1 mg/kg BW) or normal saline (vehicle). After the injection of rCIRP (1 mg/kg BW) or buffer solution (same volume), as control, serum levels of TNF-α increased markedly in the rCIRP group, about 5 fold higher than buffer (sham) group (FIG. 4A). Both TNF-α gene and protein expression increased in the liver (FIGS. 4C and D) and gut (FIGS. 4E and F) after rCIRP administration. rmCIRP also dose-dependently induced the release of another proinflammatory cytokine, HMGB1 (FIG. 10C). RAW 264.7 cells were incubated with indicated concentrations of rmCIRP for 20 h. HMGB1 levels were determined in conditioned medium (CM) were determined by Western blotting. Band intensities were quantified with densitometry. FIG. 4B shows an increase in the circulating level of HMGB1, a proinflammatory cytokine, after administration of rCIRP (1 mg/kg BW). rCIRP-treated rats showed intense immunoreactive HMGB1 bands (in triplicate), as compared to weak bands in sham group (in duplicate). In addition to the in vitro effect, intravenous administration of rmCIRP (1 mg/kg BW) to healthy rats significantly increased serum TNF-α, IL-6, and HMGB1 levels as well as the organ injury markers AST and ALT (FIGS. 17A-C) as compared to those administered with normal saline (vehicle). After 4 hours, blood and tissues were collected for analysis. FIG. 17A shows serum TNF-α, levels, measured by ELISA, and HMGB1 levels, measured by Western blotting. FIG. 17B shows TNF-α, mRNA and protein levels in liver, measured by real time RT-PCR and ELISA, respectively. Serum AST and ALT were measured 4 hours after rmCIRP administration, and levels are shown in FIG. 17C. Data are mean±s.e.m., n=6-9/group, *P<0.05 vs. vehicle.

Polymyxin B, an LPS-binding antibiotic, did not interfere with rmCIRP-induced TNF-α, production, demonstrating that LPS residue in rmCIRP was not responsible for cytokine release, while heat treatment inactivated rmCIRP's activity. In contrast, polymyxin B inhibited LPS-induced TNF-α, release by 84%, while heat treatment only slightly lowered LPS's activation (FIG. 10D). To conduct this experiment, rmCIRP (1.5 µg/ml or LPS (10 ng/ml) was treated with polymyxin B (PMB, 120 U/ml) or heated at 80° C. for 30 min before being added to RAW 264.7 cells for 8 hours. *P<0.05 vs. rmCIRP; #P<0.05 vs. LPS.

Recombinant CIRP (rCIRP) Induced Inflammatory Responses in Human Cell Lines:

As with the murine model, the stimulation of TNF-α, release by rCIRP in a human model was studied. To avoid the LPS contamination in the preparation of recombinant proteins, recombinant human CIRP (rhCIRP) was utilized, which was expressed and purified from human HEK293 cells. rhCIRP had comparable activity to rmCIRP in stimulating TNF-α, release from differentiated human THP-1 cells (FIG. 10E) as well as primary human peripheral blood mononuclear cell (PBMC) in a dose-dependent manner (FIG. 10F). These experiments were conducted by incubating differentiated human THP-1 cells with rhCIRP or rmCIRP at the indicated concentrations for 4 h. *P<0.05 vs. no CIRP. Similarly, human PBMC were incubated with the indicated concentrations of rhCIRP for 8 h. *P<0.05 vs. no rhCIRP. Thus, stimulation of cytokine release by CIRP was not attributable to LPS contamination. Furthermore, CIRP-induced cytokine activation was conserved between rodents and humans.

Figure 5:
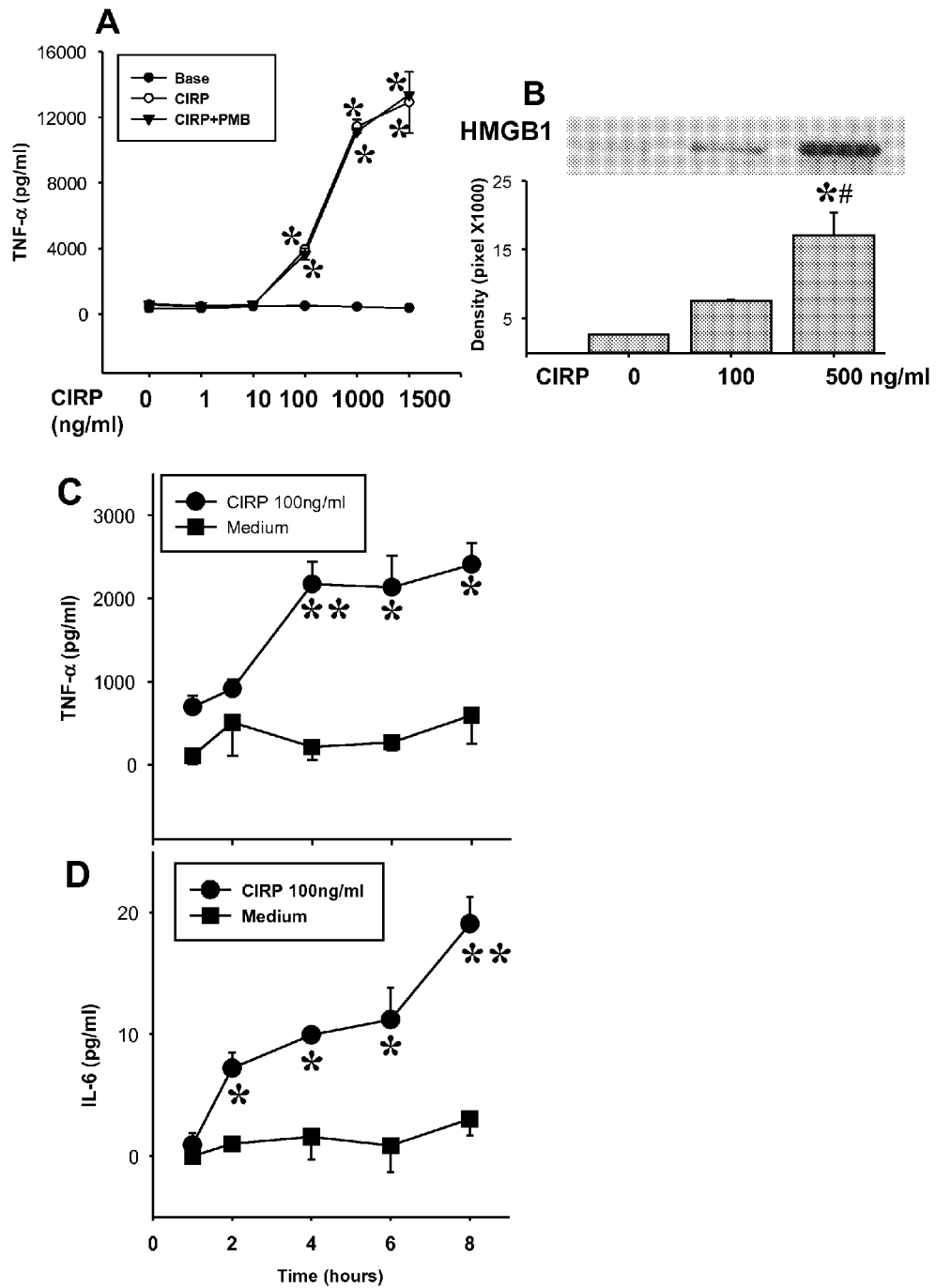
FIG. 5A through 5D illustrate the time course and effect of rCIRP on stimulation cytokine release (TNF, IL-6, HMGB1) from cultured macrophages.

Increased Release of Inflammatory Cytokines after Stimulation of Macrophages with rCIRP:

In parallel experiments, cytokines in the supernatant of cultured RAW cells incubated with rCIRP were measured. The elevated TNF-α and IL-6 levels in the supernatants of cultured RAW cell incubated with recombinant CIRP were dose- and time-dependent. As indicated in FIG. 5A, rCIRP at the dose of 100 ng/ml (4-h incubation) significantly increased TNF-α release. With regard to the time course, rCIRP at the dose of 100 ng/ml markedly increased TNF-α and IL-6 production as early as 4 and 2 h after incubation, respectively (FIGS. 5C-D). Supernatant HMGB1 level increased following rCIRP stimulation in a dose-dependent fashion. Quantifying of Western blots showed that HMGB1 release from culture RAW cell increased by about 6 fold after 20 h incubation with rCIRP at the dose of 500 ng/ml (FIG. 5B).

Example 5: Administration of Exogenous Recombinant CIRP to CIRP-Deficient Mice Induces Inflammatory Response Materials and Methods Experimental Animals:

Cirp$^{-/-}$ mice with C57BL/6 background were provided by Kumamoto University, Japan (Sakurai, T., et al. Cirp protects against tumor necrosis factor-alpha-induced apoptosis via activation of extracellular signal-regulated kinase. *Biochim. Biophys. Acta.* 1763, 290-295 (2006)). Rage$^{-/-}$, Tlr2$^{-/-}$, and Tlr4$^{-/-}$ mice were obtained from Dr. Helena Erlandsson-Harris and maintained at the Feinstein Institute for Medical Research (Yang, H., et al. A critical cysteine is required for HMGB1 binding to Toll-like receptor 4 and activation of macrophage cytokine release. *Proc. Natl. Acad. Sci. USA* 107, 11942-11947 (2010)). C57BL/6 wild-type mice were purchased from Jackson Laboratory (Bar Harbor, Me.). Male and age-matched (10 to 12 weeks) mice were used in the experiments. Animals were randomly assigned to the sham, vehicle control, or treatment groups. The number of animals used in each group was based on previous publications on animal models of hemorrhage and sepsis. All animal studies were not conducted in a completely blinded fashion. Animals were excluded from the analysis if they died during the surgical operation.

Administration of rCIRP:

In additional groups of normal healthy animals, rCIRP, for example rmCIRP (1 mg/kg BW) or buffer (same volume, 1 ml) were administered. At 4 h after the completion of treatment, blood samples were collected and placed on ice to allow clotting, and then were centrifuged at 1200 g for 10 min at 4° C., and the serum samples were stored at −80° C. until assayed. And also, tissue samples were collected and saved to liquid nitrogen immediately, then were stored at −80° C. until assayed. In another groups of hemorrhagic animals, anti-CIRP antibodies (3 mg/kg BW), rabbit IgG, or vehicles or buffer (same volume, 1 ml) were administered to hemorrhaged rats at 15 min after the initiation of fluid resuscitation via the femoral venous catheter over a period of 45 min. At 1.5 h after the completion of treatment, tissues or blood samples were collected same above.

Results

Figure 3:
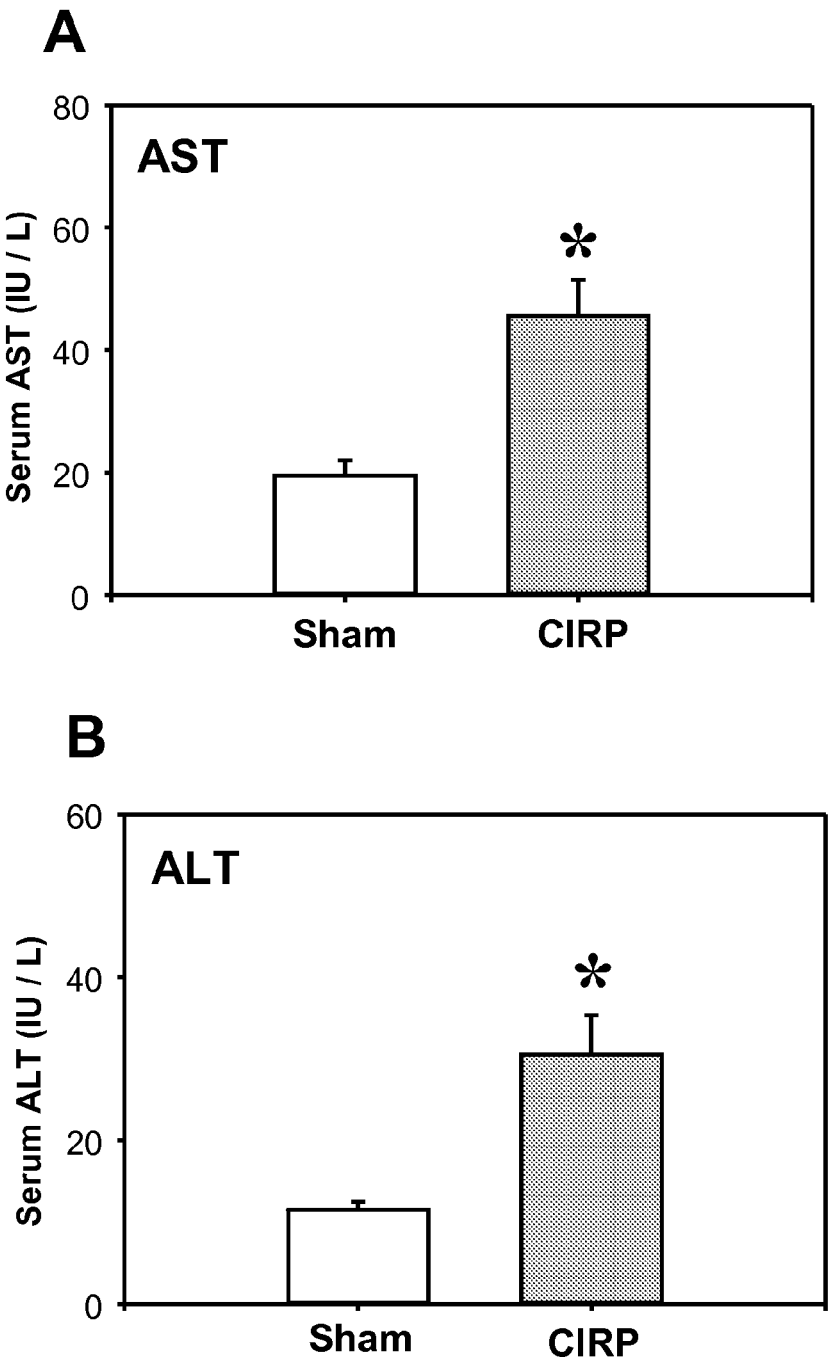
FIGS. 3A and 3B are bar graphs illustrating the elevation of blood levels of aspartate aminotransferase (AST, FIG. 3A) and alanine aminotransferase (ALT, FIG. 3B) after administration of recombinant CIRP (rCIRP) to injured animals.

Recombinant CIRP (rCIRP) Induced Tissue Injury in Healthy Rats:

To investigate the effect of rCIRP in normal animals, rCIRP (1 mg/kg BW), a recombinant protein purified from bacterial expression systems, was administered to normal healthy rats, and measured serum levels of AST and ALT (indicators of liver injury). The rats treated with rCIRP showed significantly elevated levels of AST (FIG. 3A) and ALT (FIG. 3B). These results show that rCIRP directly causes inflammatory tissues injury.

Example 6: Recombinant CIRP Works in Concert with Pro-Inflammatory Cytokine HMGB1 to Stimulate Release of TNF-α

Materials and Methods

Recombinant Proteins:

rmHMGB1 was produced as described previously (Yang, H., et al. Reversing established sepsis with antagonists of endogenous high-mobility group box 1. *Proc. Natl. Acad. Sci. USA* 101, 296-301 (2004)). Recombinant rat TNF-α was obtained from Biosource. Recombinant human (rh) CIRP (Accession #NP_001271; full length) with C-terminal DDK tag was transfected and expressed from human HEK293 cells and obtained from Origene (Rockville, Md.). rhTLR2 (Accession #NP_003255; Glu21-Leu590) and rhTLR4 (Accession #O00206; Glu24-Lys631) were transfected and expressed from mouse myeloma NS0 cell line. rhMD2 (Accession #BAA78717; Glu17-Asn160) was transformed and expressed from E. coli. The rhTLR4/MD2 complex was purified from NS0 cells co-expressed rhTLR4 (Accession #O00206; Glu24-Lys631) and rhMD2 (Accession #Q9Y6Y9; Glu17-Asn160) with His tag at each protein. All rhTLR2, rhTLR4, and rhMD2 were fused with a 10-His tag at their C-terminus and were obtained from R&D Systems (Minneapolis, Minn.). rhRAGE (Accession #Q15109; Ala23-Ala344) with C-terminal 6-His tag was transfected and expressed from human HEK293 cells and obtained from Biovision (Milpitas, Calif.).

Results

An Additive Effect of CIRP and HMGB1 on the Stimulation of TNF-α Release:

rmCIRP induced TNF-α and HMGB1 release in macrophages (FIGS. 10a, b and c). It was reported that HMGB1 can also stimulate TNF-α release (Andersson, U., et al. High mobility group 1 protein (HMG-1) stimulates proinflammatory cytokine synthesis in human monocytes. J. Exp. Med. 192, 565-570 (2000)). The relationship between CIRP and HMGB1 on stimulating TNF-α release was analyzed by applying respective neutralizing antibodies. Anti-CIRP polyclonal antibodies that effectively inhibited TNF-α production by rmCIRP in RAW 264.7 cells in a dose-dependent manner were generated. As shown in FIG. 16C, RAW 264.7 cells were pre-incubated with 20 μg/ml of anti-CIRP antibodies or rabbit control (non-immunized) IgG for 20 min before adding rmCIRP at indicated concentrations. After 4 h, TNF-α levels in conditioned medium (CM) were assayed by ELISA. Data are mean±s.e.m. from three independent experiments. *P<0.05 vs. rmCIRP+ control IgG. In FIG. 16D, RAW 264.7 cells were pre-incubated with rabbit control IgG or anti-CIRP antibodies at indicated dilutions of 1 mg/ml for 20 min before adding 1.0 μg/ml rmCIRP. After 4 h, TNF-α levels in CM were assayed by ELISA. Data are mean±s.e.m. from three independent experiments. *P<0.05 vs. rmCIRP+ control IgG. THP-1 cells were incubated with 4 μg/ml of anti-CIRP antibodies, anti-HMGB1 antibodies, or non-immunized control IgG for 1 h prior to adding rmCIRP (0.3 μg/ml), rmHMGB1 (0.3 μg/ml), or rmCIRP/rmHMGB1 (0.3 μg/ml, 0.3 μg/ml) for 8 h. *P<0.05 vs. rmCIRP; #P<0.05 vs. rmHMGB1. Pre-incubation with anti-HMGB1 antibodies (see Yang, H., et al. Reversing established sepsis with antagonists of endogenous high-mobility group box 1. Proc. Natl. Acad. Sci. USA 101, 296-301 (2004)) resulted in a 31% reduction of the TNF-α release induced by rmCIRP in THP-1 cells (P=0.292), while pre-incubation with anti-CIRP antibodies had a significant 70% reduction (P<0.05, FIG. 10G). Vice versa, pre-incubation with anti-CIRP antibodies only resulted in a 17% reduction of TNF-α release induced by rmHMGB1 (P=0.182, FIG. 10G). Furthermore, rmCIRP, rmHMGB1, and rmCIRP plus rmHMGB1 induced TNF-α levels of 0.8, 0.6, and 1.6 ng/ml, respectively. Taken together, these results indicate that CIRP and HMGB1 worked additively in stimulating TNF-α release from macrophages. TNF-α levels in all collected CM were assayed by ELISA. Data are mean±s.e.m. from three or four independent experiments.

Example 7: Anti-CIRP Antibody is Effective to Inhibit Biological Activity of CIRP in Animal Model Administration of anti-CIRP antibodies attenuated inflammatory response in an animal model, improving the survival rate of hemorrhage.

Materials and Methods

Anti-CIRP Antibody Production:

Polyclonal antiserum against CIRP was produced following standard procedures by injecting rabbits with the purified recombinant CIRP at intervals of three or more weeks (Covance Research Products, Denver, Pa.). The IgG of anti-CIRP antibody was affinity purified from serum by using immobilized immunopure protein-A/G column, according to the supplier's instructions (Pierce, Rockford, Ill.). Antibody titers were determined by a direct ELISA in 96-well format (as described by Covance Research Products, Denver, Pa.). LPS was not detectable in the purified antibody preparations as measured by Limulus amebocyte lysate assay (BioWhittaker).

Production of Anti-CIRP Polyclonal Antibodies:

Antibodies against the purified rmCIRP were raised in New Zealand White rabbits by standard procedures at Covance (Princeton, N.J.). The IgG fraction was isolated from antisera by immobilized immunopure protein-A/G chromatography (Pierce). The specificity of anti-CIRP antibody was examined by Western blotting against its purified protein. LPS was undetectable in the antibody preparations as measured by LAL assay (Cambrex). The same process was performed to purify rabbit serum control IgG.

Survival Study:

The hemorrhaged rats were administered anti-CIRP antibodies, rabbit control IgG, or normal saline (vehicle) for 3 consecutive days and their moralities were monitored for 10 days. Cirp$^{-/-}$ and wild-type mice were subjected to hemorrhage and survival was recorded for 72 h. The septic rats were administered anti-CIRP antibodies or rabbit control IgG at 5 h after CLP. Necrotic cecum was removed 20 h after CLP and their moralities were monitored for 10 days.

Granulocyte Myeloperoxidase Assessment:

Neutrophil accumulation within the pulmonary and hepatic tissues was estimated using the myeloperoxidase (MPO) activity assay as previously reported (Dwivedi A J, Wu R, Nguyen E, Higuchi S, Wang H, Krishnasastry K, Marini C P, Ravikumar T S, Wang P: Adrenomedullin and adrenomedullin binding protein-1 prevent acute lung injury after gut ischemia-reperfusion. J Am Coll Surg 205:284-293, 2007). To determine MPO activity, liver tissues were homogenized in 50 mM phosphate buffer (pH 6.0) containing 0.5% hexa-decyl-trimethyl-ammonium bromide. After centrifugation, supernatant was added to the reaction solution (0.2 mg/ml O-dianisidine dihydrochloride and 0.2 mM $H_2O_2$ in phosphate buffer) and the time change of OD at 460 nm was recorded to calculate the activity.

Results

Figure 6:
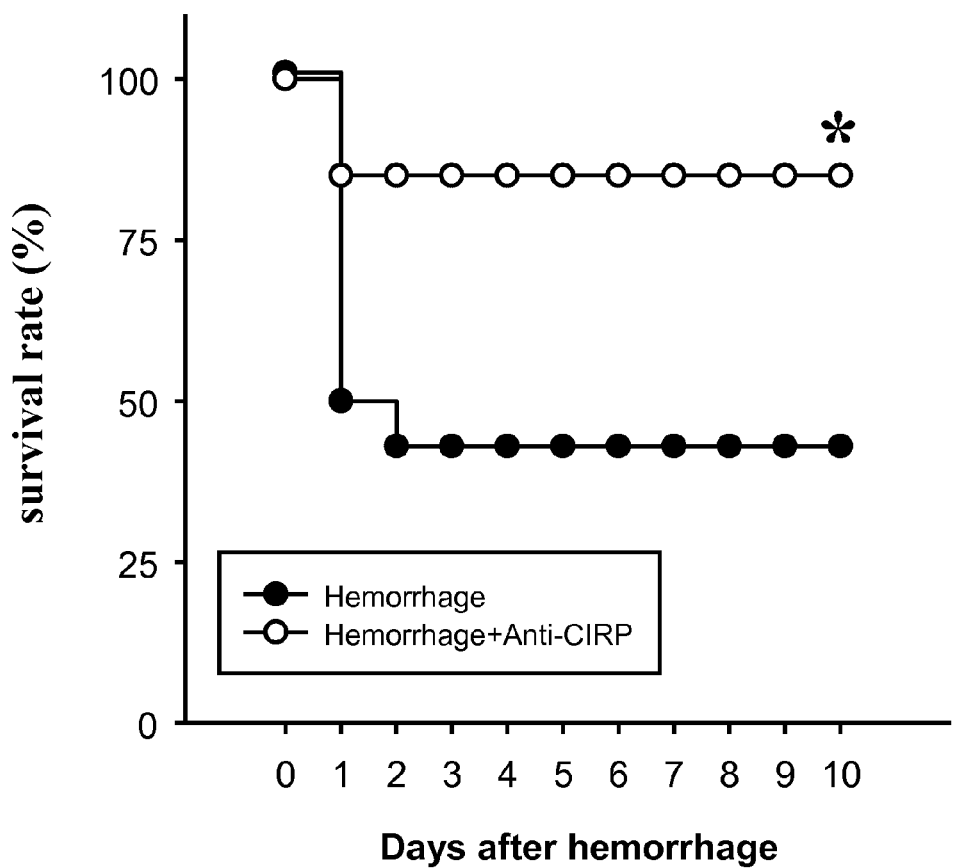
FIG. 6 is a graph illustrating the increase in survival rate by addition of anti-CIRP antibodies in animal models of hemorrhage compared with untreated control.

Anti-CIRP Antibodies Offered Significant Survival Advantage after Hemorrhage:

To further confirm that CIRP is a novel mediator in inflammatory responses to various challenges, such as hemorrhage, specific antibodies against CIRP (3 mg/kg BW) were administered to hemorrhagic rats. The results showed that that CIRP blockade provided a significant survival advantage in the of acute blood loss. As shown in FIG. 6, anti-CIRP antibody treatment increased the survival rate of experimentally hemorrhaged animals from 43% to 85% (P<0.05).

Anti-CIRP Antibodies Attenuated Tissue Injury after Hemorrhage:

To continue to investigate the pathophysiological consequences of rCIRP in the response to hemorrhage, specific antibodies against CIRP (3 mg/kg BW) were administered to hemorrhagic rats. Results indicated that the increased levels of AST, ALT, and lactate after hemorrhage was significantly attenuated by anti-CIRP antibodies (decreased by 30-40%, P<0.05) (FIGS. 7A-C).

Figure 11:
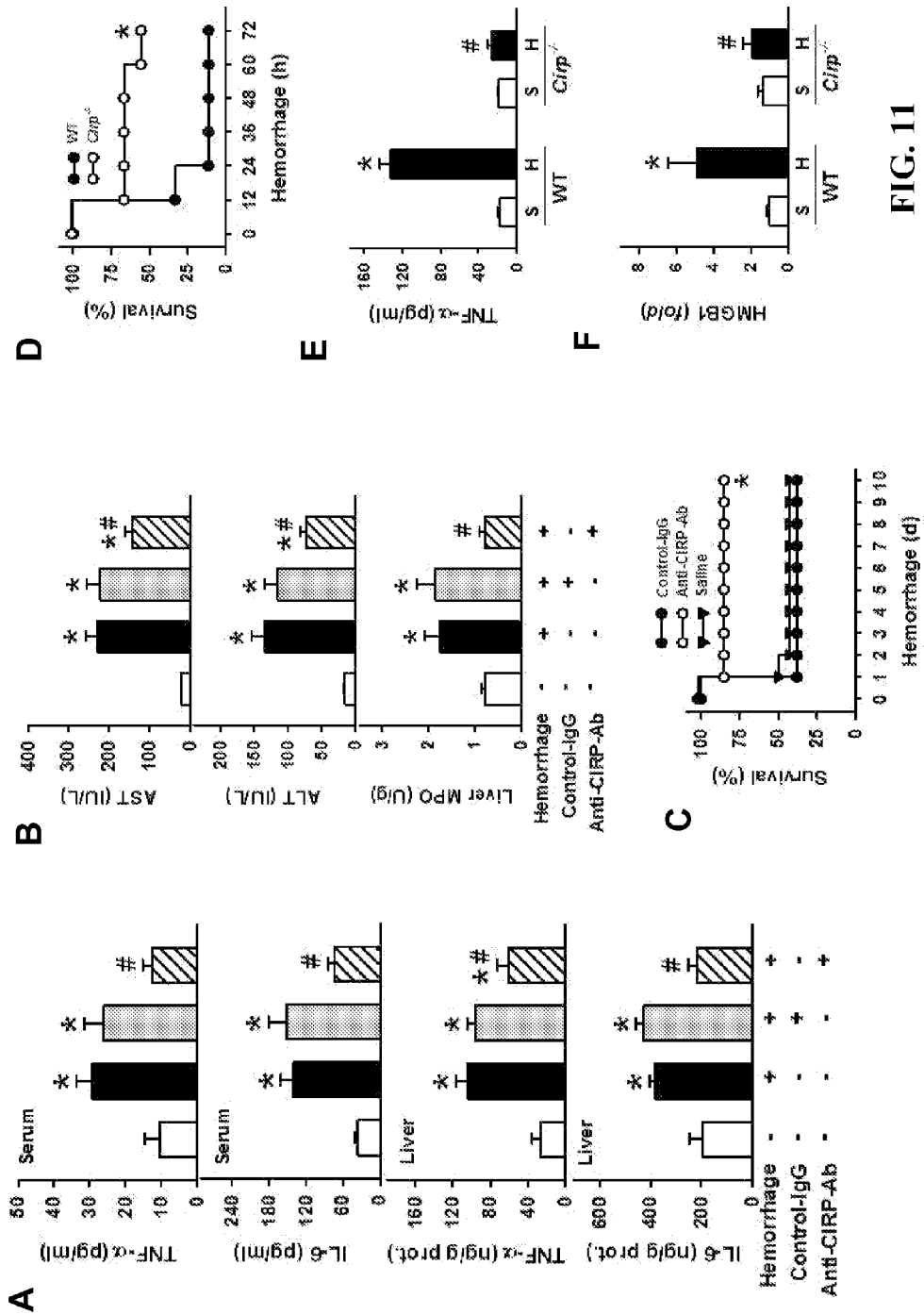
FIGS. 11A through 11F illustrate the attenuation of cytokine production and hepatic injury by anti-CIRP antibodies and prevention of lethality with anti-CIRP antibodies in an animal hemorrhage model.

Anti-CIRP Antibodies Attenuated Hemorrhage-Induced Increase in Proinflammatory Cytokines:

The role that extracellular CIRP played in mediating inflammatory responses during hemorrhage was investigated. Hemorrhaged rats received intravenous administration of rabbit control (non-immunized) IgG or neutralizing anti-CIRP antibodies (10 mg/kg BW) during fluid resuscitation. After 4 h, serum and hepatic samples were collected for measuring TNF-α and IL-6 by ELISA as well as serum AST, ALT and liver MPO activity. Data are mean±s.e.m., n=6/group, *P<0.05 vs. sham; #P<0.05 vs. hemorrhage alone. Neutralizing anti-CIRP antibodies significantly reduced serum and hepatic levels of TNF-α and IL-6, which remained unaltered by non-immunized control IgG (FIG. 11A). Hemorrhage-induced upregulation of TNF-α (FIG. 8A) and IL-6 (FIG. 8D) was significantly decreased in the serum. Very similar results were also observed in tissue levels of TNF-α (FIGS. 8B and C) and IL-6 (FIGS. 8E and F) in the lungs and liver, respectively, of animals following experimental blood depletion (hemorrhage). Serum AST and ALT, as well as liver myeloperoxidase activity—indicative of neutrophil accumulation—were significantly reduced in the anti-CIRP antibody group (FIG. 11B). Hemorrhaged rats were intravenously administered anti-CIRP antibodies (10 mg/kg BW/day, n=13), control IgG (n=13), or normal saline (vehicle; n=14) for 3 consecutive days and mortality was monitored for 10 days. *P<0.05 vs. saline. The survival rate of the anti-CIRP antibody group was significantly higher than that of the control IgG and vehicle groups 10 days after hemorrhage (85% vs. 38% and 43%; FIG. 11C). $Cirp^{-/-}$ mice (n=9) and same genetic background wild-type (WT) mice (n=9) were subjected to hemorrhage and observed for 72 h. *P<0.05 vs. WT. Concordantly, the survival rate of $Cirp^{-/-}$ mice was significantly higher than that of wild-type mice 72 h after hemorrhage (56% vs. 11%; FIG. 11D). WT and $Cirp^{-/-}$ mice were subjected to hemorrhage. After 4 h, serum samples were collected for the measurements of TNF-α levels by ELISA and HMGB1 levels by Western blotting. Data are mean±s.e.m., n=6/group, *P<0.05 vs. WT sham; #P<0.05 vs. WT hemorrhage. A 7.3-fold increase of serum TNF-α in wild-type mice at 4 h after hemorrhage was observed; such TNF-α elevation did not occur in $Cirp^{-/-}$ mice (FIG. 11E). A similar phenomenon was observed in serum HMGB1 levels (FIG. 11F), suggesting that CIRP and HMGB1 both act in contributing to the mortality of animals after shock.

Anti-CIRP Antibodies Reduced the Increased MPO Activity after Hemorrhage:

MPO (myeloperoxidase) is considered a general index of inflammation, and the increased tissue MPO activity reflected neutrophil extravasation. Experimental hemorrhage induced an increase in MPO activity in the liver. The increased MPO was significantly was reduced after the administration of anti-CIRP antibodies (FIG. 8G).

Example 8: Anti-CIRP Antibody is Effective to Increase the Survival Rate in Septic Animals Materials and Methods Animal Model of Polymicrobial Sepsis:

Animals were anesthetized with isoflurane inhalation. Cecal ligation and puncture (CLP) was performed through a midline laparotomy. Briefly, a 2-cm midline abdominal incision was performed. The cecum was exposed, ligated just distal to the ileocecal valve to avoid intestinal obstruction, punctured twice with an 18-gauge needle, squeezed slightly to allow a small amount of fecal matter to flow from the holes, and then returned to the abdominal cavity. The abdomen was closed in layers with suture. Sham-operated animals underwent the same procedure with the exception that the cecum was neither ligated nor punctured. The animals were resuscitated with 3 ml/100 g BW normal saline subcutaneously immediately after surgery.

Cell Culture and Isolation of Peritoneal Macrophages:

Murine macrophage-like RAW 264.7 cells and human monocyte THP-1 cells were obtained from ATCC (Manassas, Va.). Primary peritoneal macrophages were isolated from C57BL/6 wild-type, $Rage^{-/-}$, $Tlr2^{-/-}$, and $Tlr4^{-/-}$ mice at day 3 after intraperitoneal injection with 4% thioglycolate as previously described (Yang, H., et al. A critical cysteine is required for HMGB1 binding to Toll-like receptor 4 and activation of macrophage cytokine release. *Proc. Natl. Acad. Sci, USA* 107, 11942-11947 (2010)). Rat primary peritoneal macrophages were directly isolated from the abdominal cavity of a male Sprague-Dawley rat without pre-induction. RAW 264.7 cells and peritoneal macrophages were cultured in DMEM and RPMI1640 (Invitrogen, Grand Island, N.Y.), respectively. THP-1 cells were cultured in RPMI1640 with 0.05 mM 2-mercaptoethanol and differentiated into macrophage-like cells by incubating with phorbol 12-myristate 13-acetate (20 ng/ml) for 48 h. All cultured media were supplemented with 10% heat-inactivated FBS, 1% penicillin/streptomycin and 2 mM glutamine. Cells were maintained in a 37° C. incubator with 5% $CO_2$.

Results

Figure 12:
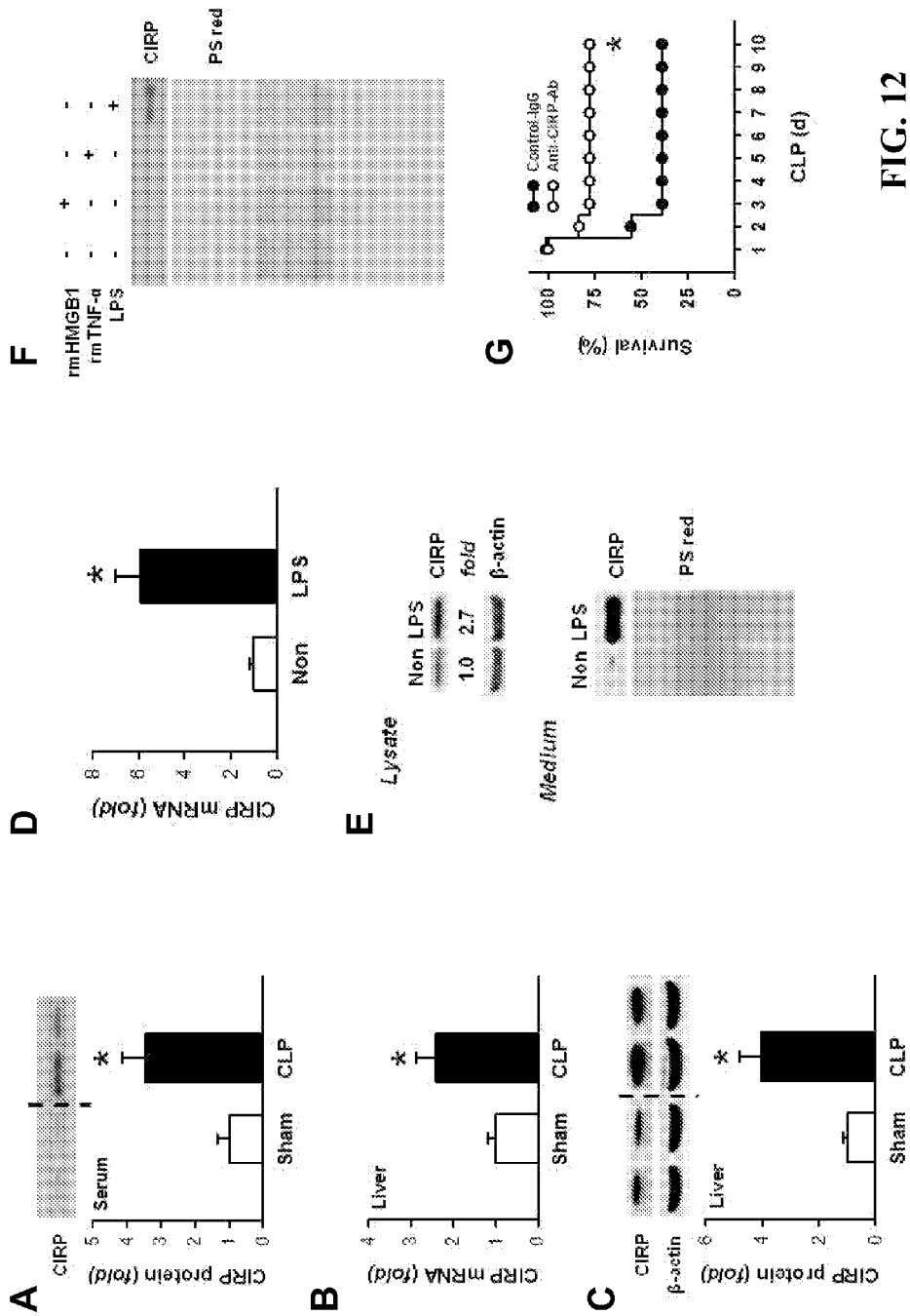
FIGS. 12A through 12G illustrate expression and release of CIRP during sepsis in septic animal model, as well as the effect of anti-CIRP antibodies (FIG. 12G).

Upregulation and Release of CIRP in Septic Animals:

The pro-inflammatory activity of CIRP in sepsis, another clinical condition caused by hyperinflammation, was investigated. CIRP expression in rats subjected to cecal ligation and puncture (CLP), an established animal model of polymicrobial sepsis was investigated (see Yang, S., Zhou, M., Chaudry, I. H. & Wang, P. Novel approach to prevent the transition from the hyperdynamic phase to the hypodynamic phase of sepsis: role of adrenomedullin and adrenomedullin binding protein-1. *Ann. Surg.* 236, 625-633 (2002)). After 20 h, blood and liver tissues were collected for analyses. Serum CIRP levels were determined by Western blotting. Band intensities were quantified through densitometry. At 20 h after CLP, serum levels of CIRP were increased by 3.4-fold, compared to the sham (FIG. 12A). The mRNA and protein levels of CIRP in the liver were assessed by real time RT-PCR and Western blotting, respectively. Data are mean±s.e.m., n=4-6/group, *P<0.05 vs. sham. mRNA and protein levels of CIRP in the liver were also increased by 2.4- and 4.0-fold, respectively (FIGS. 12B and 12C). The effect of LPS on regulating CIRP expression and release in macrophages was assessed. Peritoneal macrophages isolated from rats were plated and exposed to LPS (10 ng/ml) or non-treated (Non). After 6 h, CIRP mRNA levels in macrophages were analyzed by real time RT-PCR. CIRP expression levels were normalized to GAPDH. The value in non-treated cells is designated as 1 for comparison. Data are mean±s.e.m. from three independent experiments. *P<0.05 vs. Non. The mRNA and protein levels of CIRP in rat primary peritoneal macrophages were significantly increased after exposure to LPS for 6 and 24 h, respectively (FIG. 12D). Total cell lysate and cultured medium were collected at 24 h and 6 h, respectively, after exposure to LPS, and subjected to Western blotting. Data represents three independent experiments. CIRP protein was also detected in CM after 6 h exposure to LPS, while it was undetectable from non-treated cells (FIG. 12E). Other inflammatory mediators inducing CIRP release were investigated. Incubation of RAW 264.7 cells with rmHMGB1 (1 µg/ml) or rmTNF-α (30 ng/ml) for 24 h did not cause CIRP release into CM, whereas CIRP protein was detectable from cells exposed to LPS (100 ng/ml). The conditioned medium was subjected to Western blotting and data represents three independent experiments (FIG. 12F). To validate the detrimental activity of extracellular CIRP, neutralizing anti-CIRP antibodies were administered to septic animals. CLP rats were intravenously administered anti-CIRP antibodies (10 mg/kg BW, n=18) or non-immunized control IgG (10 mg/kg BW, n=18) at 5 h after CLP. Mortality was monitored for 10 days. *P<0.05 vs. control IgG. PS red, Ponceau S red staining. The 10-day survival rate of septic rats significantly increased from 39% to 78% after treatment with anti-CIRP antibodies (FIG. 12G). Thus, CIRP was also a detrimental factor in septic shock.

Example 9: CIRP Binds to the TLR4/MD2 Cell Surface Receptor Complex

Materials and Methods
Surface Plasmon Resonance (SPR) Analysis:
Analysis of protein-protein and peptide-protein interactions were conducted using the BIAcore T200 instrument (GE Healthcare). Binding reactions were performed in 1×PBS buffer containing 0.01% Tween-20 (pH 7.4). The CM5 dextran chip (flow cell-2) was first activated by injection with 89 µl of 0.1 M N-ethyl-N'-[3-diethylaminopropyl]-carbodiimide and 0.1 M N-hydroxysuccinimide. An aliquot of 200 µl of 5 µg/ml of the ligand diluted in 10 mM sodium acetate (pH 4.5) was injected into flow cell-2 of the CM5 chip for immobilization. Next, 135 µl of 1 M ethanolamine (pH 8.2) was then injected to block the remaining active sites. The flow cell-1 without coating with the ligand was used as a control to evaluate nonspecific binding. The binding analyses were performed at flow rate of 30 µl/min at 25° C. To evaluate the binding, the analyte (ranging from 62.5 nM to 1.0 µM for kinetics analysis or 0.5 µM for yes/no binding analysis) was injected into flow cell-1 and -2 and the association of analyte and ligand was recorded respectively by surface plasmon resonance. The signal from the blank channel (flow cell-1) was subtracted from the channel (flow-cell 2) coated with the ligand. Data were analyzed by the BIAcore T200 Evaluation Software. For all samples, a blank injection with buffer alone was subtracted from the resulting reaction surface data. Data were globally fitted to the Lagmuir model for a 1:1 binding.

Figure 13:
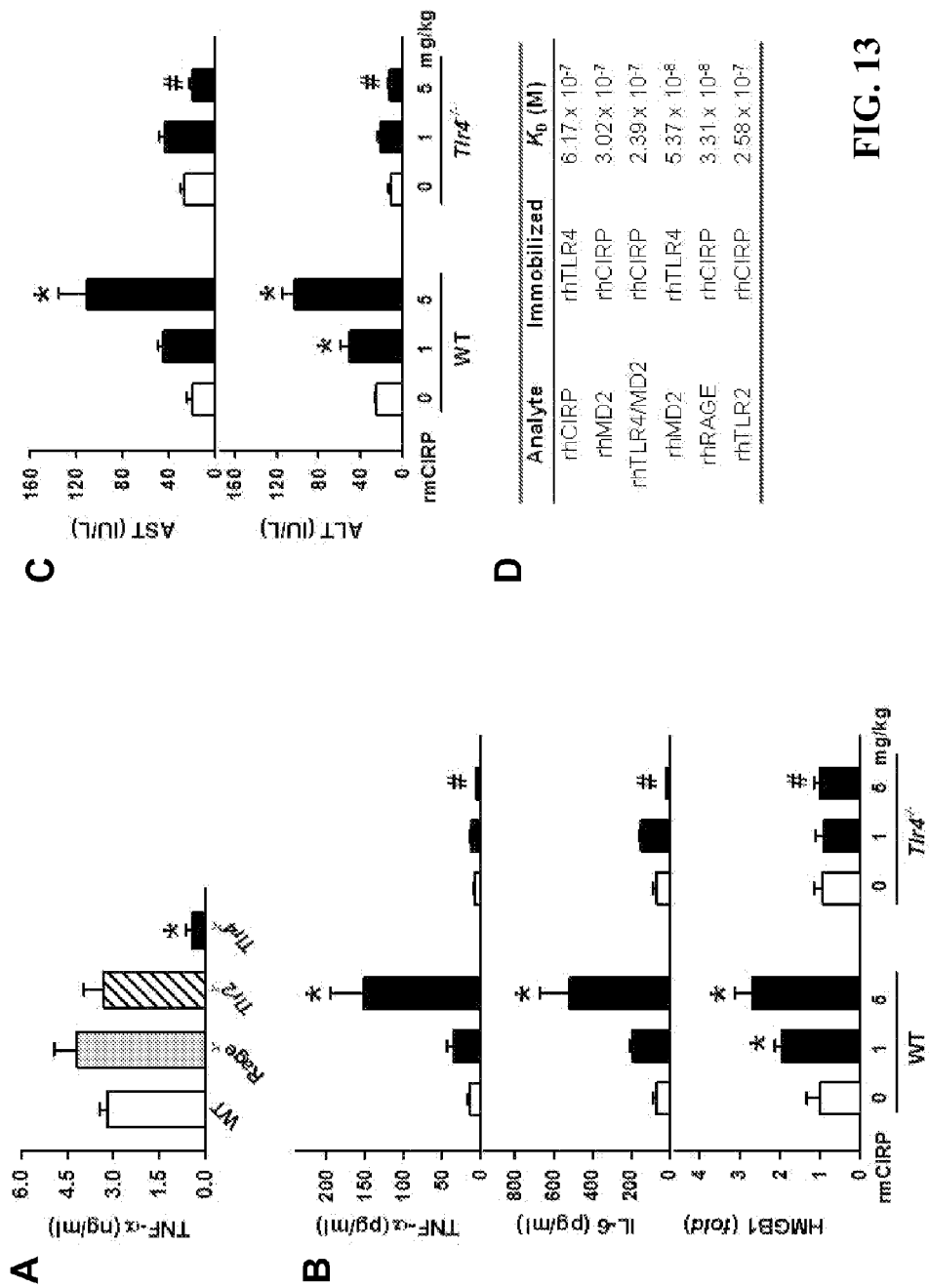
FIGS. 13A through 13D demonstrate that the TLR4/MD2 complex mediates extracellular CIRP activity.

Results
CIRP Induced Inflammatory Responses Through TLR4:
Cell surface receptors responsible for transmitting extracellular CIRP signaling were identified. Three major PRRs known to mediate inflammation were examined: RAGE, TLR2, and TLR4 (see (a) Zhang, X. & Mosser, D. M. Macrophage activation by endogenous danger signals. *J. Pathol.* 214, 161-178 (2008); (b) Beutler, B. A. TLRs and innate immunity. Blood 113, 1399-1407 (2009); (c) Ward, P. A. The sepsis seesaw: seeking a heart salve. Nat. Med. 15, 497-498 (2009)). Peritoneal macrophages isolated from WT, Rage$^{-/-}$, Tlr2$^{-/-}$, or
Tlr4$^{-/-}$ mice were incubated with 1.5 µg/ml rmCIRP for 4 h. TNF-α levels in conditioned medium were assayed by ELISA. Data are mean±s.e.m. from three independent experiments. *P<0.05 vs. WT. In comparing the difference among wild-type and knockout mice targeting each receptor in response to rmCIRP, only TLR4-deficient macrophages lost the response for TNF-α induction, while RAGE- and TLR2-deficient macrophages maintained similar responses to wild-type macrophages (FIG. 13A). To confirm the requirement of TLR4 in mediating CIRP activity, wild-type and TLR4 knockout mice were injected with rmCIRP (1 or 5 mg/kg BW) or normal saline (vehicle). After 4 h, serum samples were collected and assayed for TNF-α and IL-6 by ELISA and HMGB1 by Western blotting as well as serum AST and ALT. Data are mean±s.e.m., n=6-9/group, *P<0.05 vs. WT no rmCIRP; #P<0.05 vs. WT with rmCIRP at 5 mg/kg. Similar to rats, wild-type mice exhibited an increase of serum proinflammatory cytokines (TNF-α, IL-6, and HMGB1) and organ injury markers (AST and ALT) in a dose-dependent manner to rmCIRP injection (FIGS. 13B and 13C). In contrast, these deleterious effects of rmCIRP on the wild-type mice were diminished in Tlr4$^{-/-}$ mice.

Figure 14:
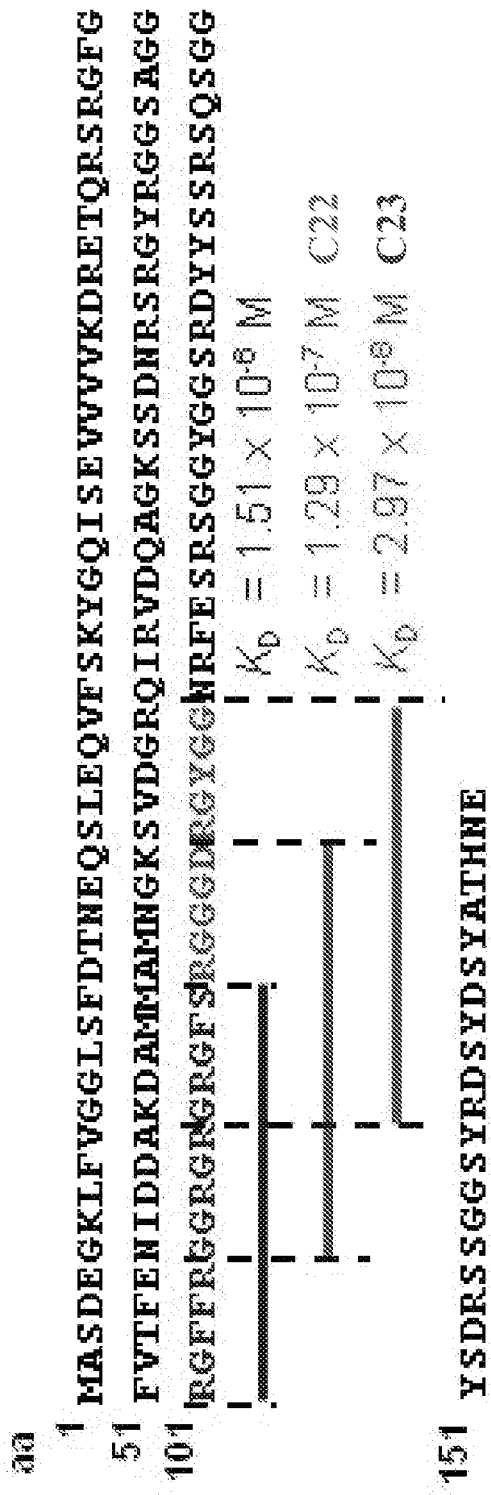
FIG. 14 illustrates the binding region of human CIRP to rhMD2.
Figure 18:
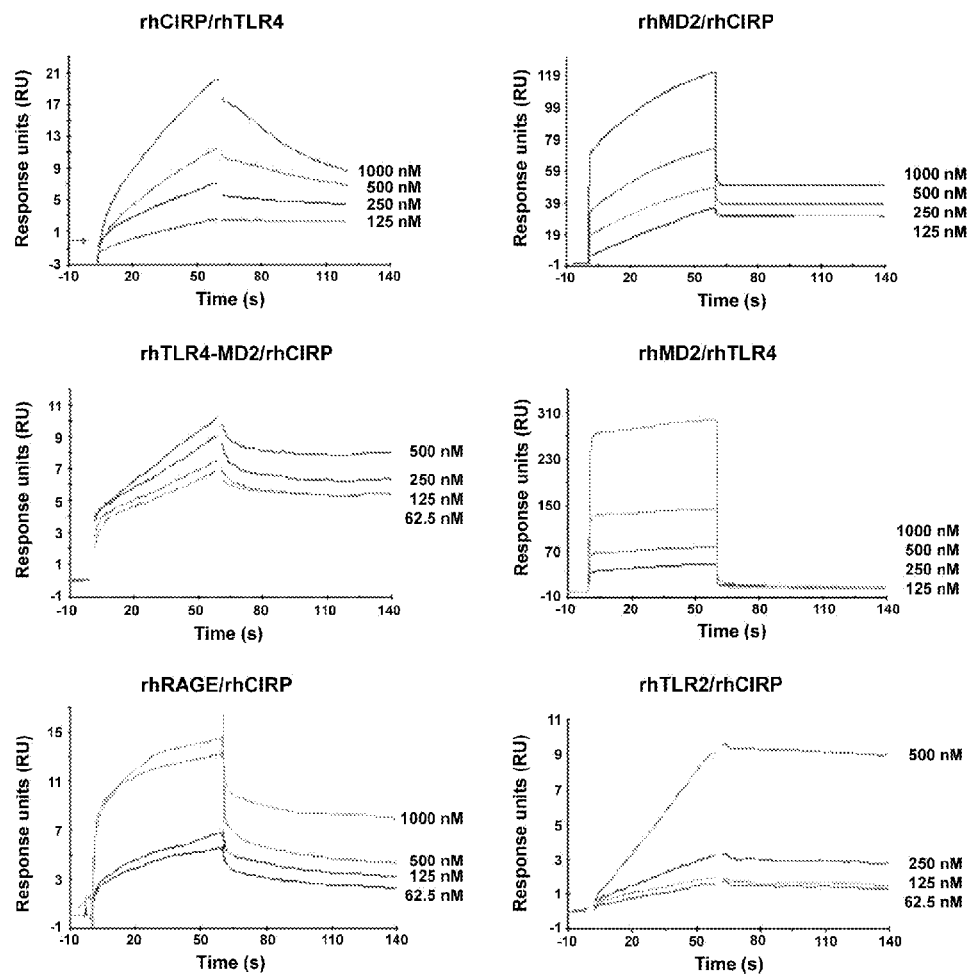
FIG. 18 illustrates the binding kinetics of rhCIRP with the pattern-recognition receptors measured by surface plasmon resonance (SPR) analysis.
Figure 19:
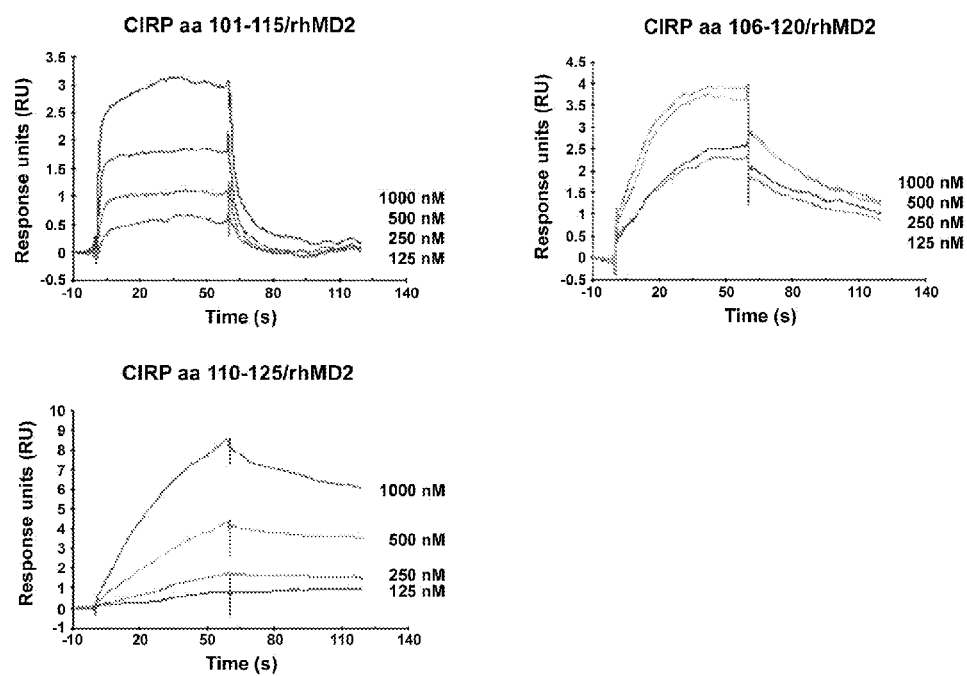
FIG. 19 illustrates the binding kinetics of 15-mer oligopeptides derived from human CIRP with rhMD2 by surface plasmon resonance (SPR) analysis.

CIRP Directly Bound to the TLR4/MD2 Complex:
Surface plasmon resonance (SPR) analysis was utilized to determine the physical interaction and binding affinity between rhCIRP and pattern-recognition receptors and MD2. TLR4 often accompanies MD2, as a co-receptor, to form the TLR4/MD2 complex (Nagai, Y., et al. Essential role of MD-2 in LPS responsiveness and TLR4 distribution. *Nat. Immunol.* 3, 667-672 (2002). All the recombinant proteins were derived from human coding sequence for SPR analysis. The apparent $K_D$ was determined by a kinetic analysis with a series of concentrations of analyte. rhCIRP bound to rhTLR4, rhMD2, and the rhTLR4/MD2 complex with an apparent $K_D$ of $6.17 \times 10^{-7}$, $3.02 \times 10^{-7}$, and $2.39 \times 10^{-7}$ M, respectively (FIG. 13d and FIG. 18). Representative sensorgrams of the analyte analysis are shown in FIG. 18 from two to three independent experiments. The sensorgrams show association and dissociation of analyte at the indicated concentration passed over to the immobilized ligand on the sensor chip, indicated as analyte/ligand on top of each diagram. The binding of rhMD2 to rhTLR4 was examined as a positive control and obtained an apparent $K_D$ of $5.37 \times 10^{-8}$ M, which is very close to the previously reported $K_D$ of $6.29 \times 10^{-8}$ M, (Hyakushima, N., et al. Interaction of soluble form of recombinant extracellular TLR4 domain with MD-2 enables lipopolysaccharide binding and attenuates TLR4-mediated signaling. *J. Immunol.* 173, 6949-6954 (2004)). Intriguingly, rhCIRP had a $K_D$ in the nM range with RAGE and TLR2 (FIG. 13D and FIG. 18); however, the biological significance of these bindings remains to be determined. These SPR results clearly indicated that CIRP was capable of interacting with different types of proteins, which fits its character as a chaperone protein. The region of CIRP that binds to MD2 was determined via the synthesis of 32 oligopeptides (15-mer) covering the entire human CIRP sequence. The oligopeptides were passed over immobilized rhMD2 on the BIAcore instrument, followed by subsequent performance of a series of SPR analyses. Three oligopeptides with high binding affinity were indicated. Representative sensorgrams, from two independent experiments, of the oligopeptide analysis are shown in FIG. 19, demonstrating association and dissociation of analyte at the indicated concentration passed over to the immobilized rhMD2 on the sensor chip, indicated as analyte/rhMD2 on the top of each diagram. Three oligopeptides, aa 101-115, 106-120 (C22), and 111-125 (C23) bound to rhMD2 with high affinity (FIG. 14 and FIG. 19).

Example 10: Oligopeptides C22 and C23 Inhibit rmCIRP-Induced Production of TNF-α in Cell Lines Materials and Methods Synthesis of Oligopeptides:

A panel of 32 15-mer oligopeptides was synthesized and purified by high performance liquid chromatography at Genscript (Piscataway, N.J.). Each 15-mer oligopeptide sequence (SEQ ID NOs: 13-44) is derived from hCIRP (FIG. 1).

Cell Culture:

Human monocytic THP-1 cells (American Type Culture Collection, Manassas, Va.), were seeded in suspension into T75 tissue culture flask at a density of $1.5 \times 10^6$ cells and cultured with RPMI-1640 medium supplemented with 10% heat-inactivated fetal bovine serum, 1% penicillin/streptomycin, 2 mM glutamine and additional 0.05 mM β-mercaptoethanol at 37° C. in a humidified incubator with 5% $CO_2$.

Differentiation and Treatment of Cells:

Cells were plated at a density of $5 \times 10^4$ per well in 96-well tissue culture plate and incubated with phorbol 12-myristate 13-acetate (20 ng/ml) for 48 h to become differentiated macrophages-like cells before experiment. Cells were used between passages 5 and 12. Cells were pretreated with indicated concentrations of CIRP-derived peptides C22 (SEQ ID NO: 13) or C23 (SEQ ID NO: 12) for 1 h, and then incubated in the absence or presence rmCIRP or LPS (from E. coli O111:B4, Sigma St. Louis, Mo.) with Opti-MEM-medium for 6 h. The cell-free supernatants were assayed for TNF-α by ELISA.

Cytokine Assay:

Supernatants were measured for TNF-α levels using a commercially available enzyme-linked immunosorbent assay (ELISA) kits-human TNF-α set (BioSource International, Camarillo, Calif.) according to the manufacturer's instruction.

Results

Figure 20:
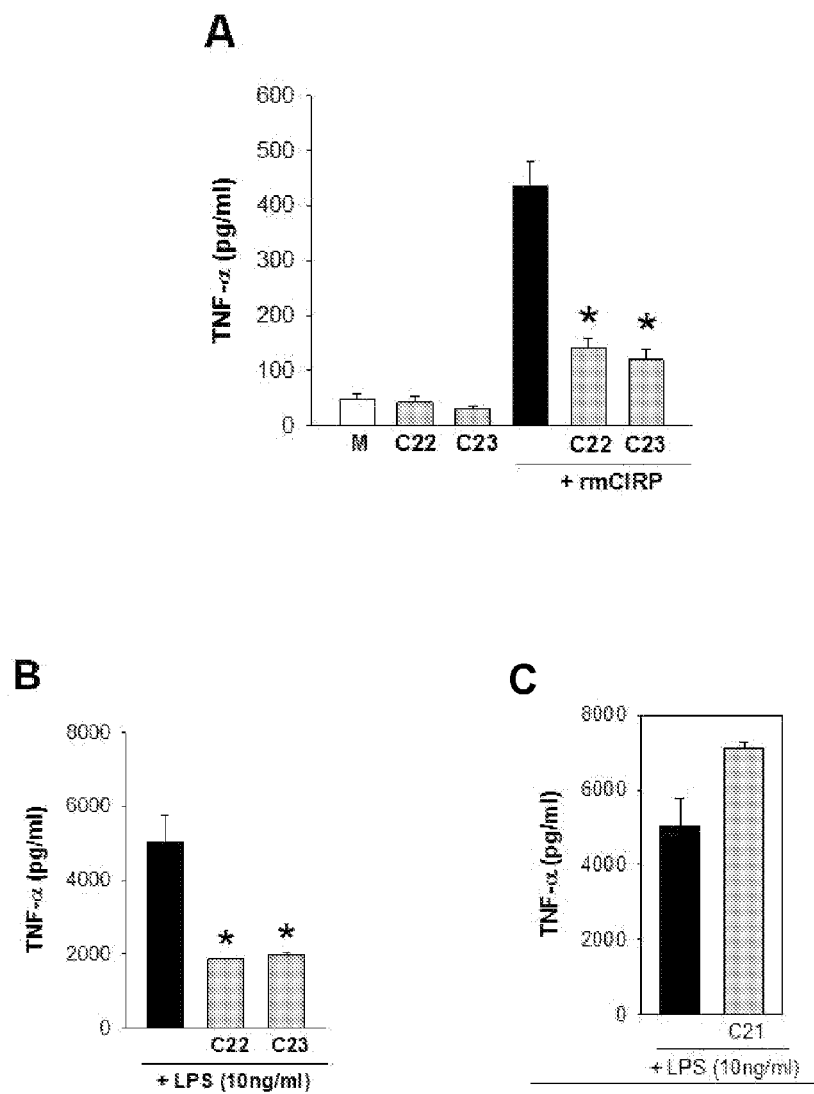
FIGS. 20A through 20C illustrates the inhibitory effects of oligopeptides C22 and C23 (but not C21) on the production of TNF-α by human THP-1 cells.

Effect of C22 and C23 on rmCIRP-Induced TNF-α Production in Differentiated THP-1 Cells:

As shown in FIG. 20A, CIRP-peptides alone did not affect TNF-α production, detectable amounts similar to medium. However, pretreatment with the C22 (SEQ ID NO: 13) or C23 (SEQ ID NO: 14) at dose 50 ng/ml significantly attenuated rmCIRP 300 ng/ml-induced TNF-α production. The inhibition levels range at 67-72%. To consider the size difference between two molecules, peptides dose 2-fold higher than rmCIRP were used if covert to molar concentration.

Effect of C22 and C23 on LPS-Induced TNF-α Production in Differentiated THP-1 Cells:

The CIRP-derived peptides were also found to modulate LPS-induced TNF-α release in differentiated THP-1 cells. As shown in FIG. 20B, C22 (SEQ ID NO: 13) or C23 (SEQ ID NO: 14) suppressed LPS-induced TNF release by 61-63%. The doses of C22 or C23 at 2 ng/ml, equivalent to 1.3 pmol/ml and LPS at 10 ng/ml, equivalent to 0.67 pmol/ml, peptides and LPS molar ratios at 2:1 were used to treat cells.

Example 11: Oligopeptides C1-C21 and C24-C32 Show Little to No Inhibitory Effect on rCIRP-Induced Production of TNF-α in Cell Lines The results below demonstrate the surprising inhibitory effect of peptides C22 and C23 on rCIRP-induced secretion of TNF-α.

Materials and Methods

The experimental protocols for the synthesis of oligopeptides C1-C21 and C24-C32, cell culture using THP-1 cells, treatment of cells, and cytokine assay are described in Example 10. The cells were treated with CIRP (1000 ng/ml) for stimulation. The peptides were incubated with 10× molar concentration of CIRP for 1 hour prior to stimulation. TNF-α levels were assayed in the culture medium 4 hours after stimulation by ELISA.

The following peptides were assayed for their inhibitory activity on rmCIRP-induced TNF-α production in differentiated THP-1 cells:

| | | |
|---|---|---|
| C1: | MASDEGKLFVGGLSF; | (SEQ ID NO: 15) |
| C2: | GKLFVGGLSFDTNEQ; | (SEQ ID NO: 16) |
| C3: | GGLSFDTNEQSLEQV; | (SEQ ID NO: 17) |
| C4: | DTNEQSLEQVFSKYG; | (SEQ ID NO: 18) |
| C5: | SLEQVFSKYGQISEV; | (SEQ ID NO: 19) |
| C6: | FSKYGQISEVVVVKD; | (SEQ ID NO: 20) |
| C7: | QISEVVVVKDRETQR; | (SEQ ID NO: 21) |
| C8: | VVVKDRETQRSRGFGF; | (SEQ ID NO: 22) |
| C9: | RETQRSRGFGFVTFE; | (SEQ ID NO: 23) |
| C10: | SRGFGFVTFENIDDA; | (SEQ ID NO: 24) |
| C11: | FVTFENIDDAKDAMM; | (SEQ ID NO: 25) |
| C12: | NIDDAKDAMMAMNGK; | (SEQ ID NO: 26) |
| C13: | KDAMMAMNGKSVDGR; | (SEQ ID NO: 27) |
| C14: | AMNGKSVDGRQIRVD; | (SEQ ID NO: 28) |
| C15: | SVDGRQIRVDQAGKS; | (SEQ ID NO: 29) |
| C16: | QIRVDQAGKSSDNRS; | (SEQ ID NO: 30) |
| C17: | QAGKSSDNRSRGYRG; | (SEQ ID NO: 31) |
| C18: | SDNRSRGYRGGSAGG; | (SEQ ID NO: 32) |
| C19: | RGYRGGSAGGRGFFR; | (SEQ ID NO: 33) |
| C20: | GSAGGRGFFRGGRGR; | (SEQ ID NO: 34) |
| C21: | RGFFRGGRGRGRGFS; | (SEQ ID NO: 35) |
| C22: | GGRGRGRGFSRGGGD; | (SEQ ID NO: 13) |

-continued

```
C23:        GRGFSRGGGDRGYGG;              (SEQ ID NO: 14)

C24:        RGGGDRGYGGNRFES;              (SEQ ID NO: 36)

C25:        RGYGGNRFESRSGGY;              (SEQ ID NO: 37)

C26:        NRFESRSGGYGGSRD;              (SEQ ID NO: 38)

C27:        RSGGYGGSRDYYSSR;              (SEQ ID NO: 39)

C28:        GGSRDYYSSRSQSGG;              (SEQ ID NO: 40)

C29:        YYSSRSQSGGYSDRS;              (SEQ ID NO: 41)

C30:        SQSGGYSDRSSGGSY;              (SEQ ID NO: 42)

C31:        YSDRSSGGSYRDSYD;              (SEQ ID NO: 43)

C32:        SGGSYRDSYDSYATH.              (SEQ ID NO: 44)
```

Figure 22:
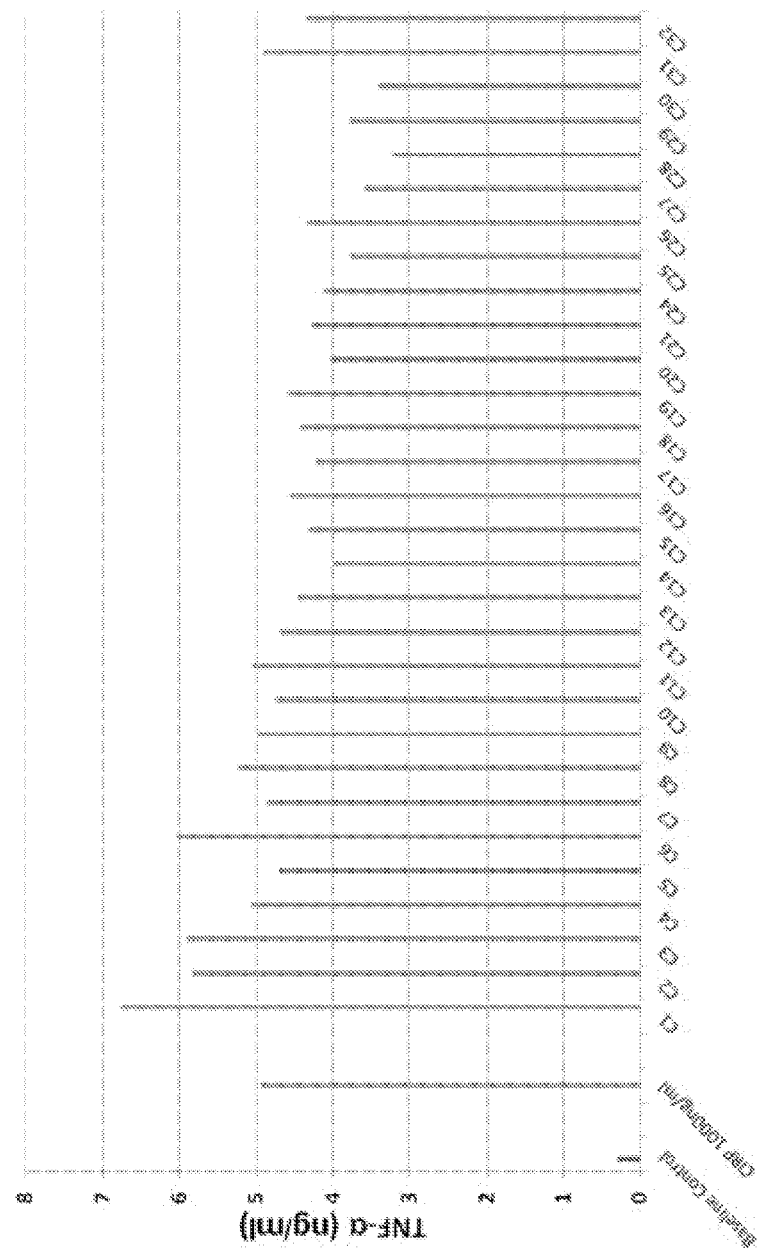
FIG. 22 is a bar graph demonstrating the effect of multiple CIRP-derived peptides on TNA-α secretion by THP-1 cells after CIRP stimulation.

Effect of CIRP-Derived Peptides C1-C21 and C24-C32 on rmCIRP-Induced TNF-α Production in Differentiated THP-1 Cells:

As shown in FIG. 22, CIRP-derived peptides C1-C21 and C24-C32 did not significantly attenuate rmCIRP-induced TNF-α secretion by THP-1 cells.

Effect of C21 on LPS-Induced TNF-α Production in Differentiated THP-1 Cells:

CIRP-derived peptides C22 and C23 inhibit LPS-induced TNF-α release in differentiated THP-1 cells, as demonstrated in Example 10, and illustrated in FIG. 20B. However, as shown in FIG. 20C, peptide C21 does not suppress LPS-induced TNF-α release in THP-1 cells.

Example 12: CIRP-Null Mice have a Faster Wound Closure Rate than Wild Type Mice

To identify the involvement of CIRP in wound healing, an animal model of cutaneous wound was used to compare the rate of wound closure between wild-type (WT) and CIRP-null mice. The detail procedure and measurements were as follows. Full-thickness 2.0-cm diameter circular excision wounds were surgically created on the dorsum of both 3 month-old male CIRP-null and WT mice. The size of the wound was measured until day 14 post wounding and quantified by NIH ImageJ software. Another two sets of animals were euthanized at days 3 and 7 and full thickness skin samples were collected for histological evaluation and measurements of the expression of various genes by real time RT-PCR.

Figure 21:
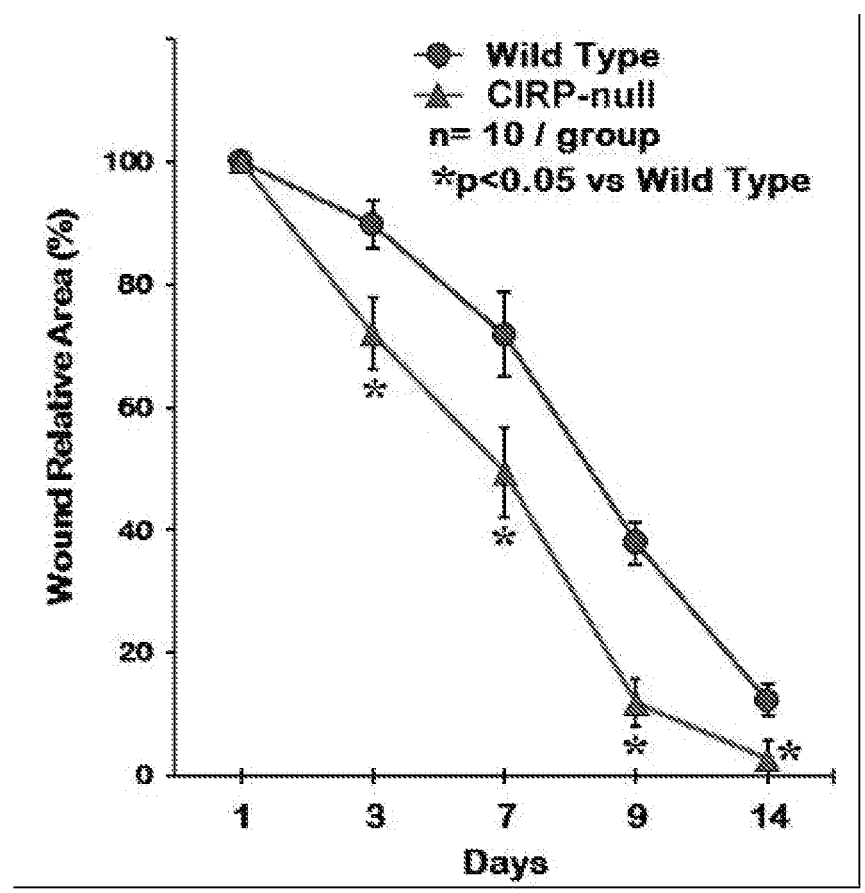
FIG. 21 is a plot showing smaller relative area of a cutaneous wound in CIRP-null mice versus wild-type mice as a function of the number of days of healing.

As shown in FIG. 21, the healing rate of cutaneous wounds in CIRP-null mice was significantly faster than that in WT mice over the 14-day time course.

Histological analyses with H&E and Masson-Trichrome staining indicated that CIRP-null wounds had a better quality of wound closure and collagen deposition than WT ones. At the early wound healing, cells staining positive with the cell proliferation maker Ki67 in the CIRP-null wounds outnumbered those in WT. The inflammatory mediators TNF-alpha and IL-6 in CIRP-null wounds were 2.6- and 2.8-fold higher, respectively, than those in WT ones at day 3, while their levels in CIRP-null wounds became 60% and 68% lower, respectively, than in WT ones at day 7. Correspondingly, the number of cells positive for myeloperoxidase staining, indicating neutrophil infiltration, was higher in CIRP-null than WT wounds. There was no difference in VEGF expression and PECAM-1/CD31 staining between CIRP-null and WT wounds at days 3 and 7. The MMP-9 mRNA levels in CIRP-null wounds were 2.2-fold higher than WT ones at day 3.

These results indicate that CIRP-null mice exhibited faster healing of a cutaneous wound. This accelerated healing was associated with promotion of cell proliferation, earlier activation and resolution of inflammation, and acceleration of matrix remodeling. These results show that CIRP expression may hinder the healing process, and that inhibition of CIRP in the setting of a cutaneous wound will improve the rate and quality of wound closure and healing.

Example 13: Oligopeptide C23 Abrogates CIRP-Induced Activation of Endothelial Cells In Vivo and In Vitro Oligopeptide C23 was identified as the oligopeptide with the highest affinity for TLR4 co-receptor MD2. (See, FIG. 14, listing comparative data for $K_D$ of selected fragments.)

In the experiments described below, C23 was shown to prevent induction of expression of ICAM-1 (Intercellular Adhesion Molecule 1) in mouse lung vascular endothelial cells (MLVECs) stimulated with rmCIRP, as well as prevention of release of IL-1beta, a pro-inflammatory cytokine, from MLVEC.

Figure 23A:
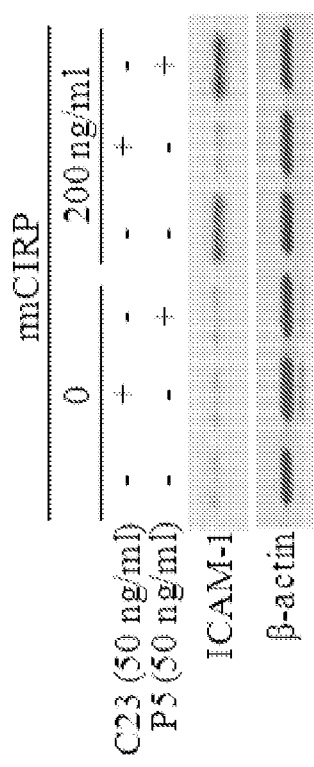
FIG. 23A is a photograph of a Western blot illustrating the effect of oligopeptide C23 on the level of expression of ICAM-1 in MLVEC after CIRP stimulation.

FIG. 23A is a photograph of an SDS-PAGE/Western blot demonstrating the expression levels of ICAM-1. MLVEC were treated with rmCIRP in the presence of C23 or non-specific oligopeptide P5 (negative control) for 4 hours. Cells were harvested, lysed and the cell lysate analyzed by SDS-PAGE and Western blotting (immunodetection). Referring to FIG. 23A, ICAM-1 expression is abrogated in the presence of 200 ng/ml of the oligopeptide C23.

Figure 23B:
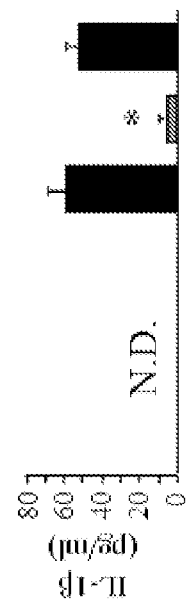
FIG. 23B is a bar plot illustrating the effect of oligopeptide C23 on the level of secretion of IL-1beta from MLVEC after CIRP stimulation.

Similarly, the release of IL-1beta by MLVEC stimulated by rmCIRP was blocked (as determined by ELISA) when 200 ng/ml of the oligopeptide C23 was added to the media, as shown in FIG. 23B. (For FIGS. 23A and 23B: Mean+/−SD, n=3, *P<0.05 vs. groups without C23.)

Figures 24A, 24B, 24C:
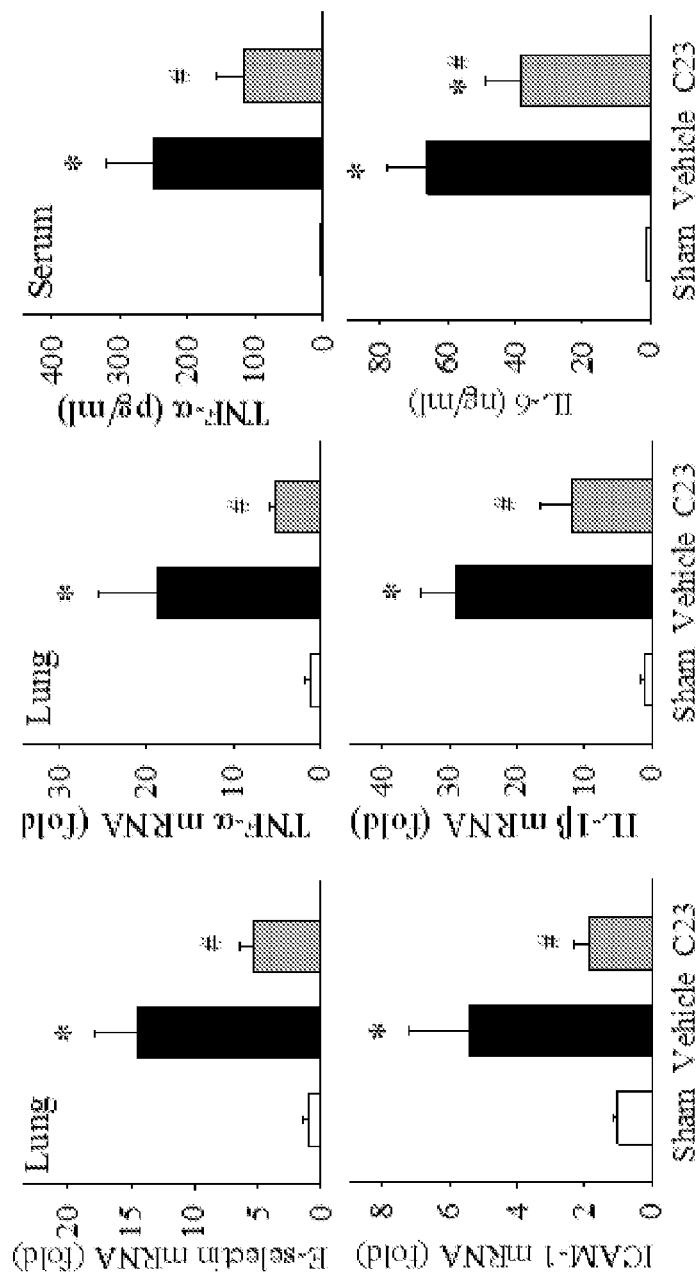
FIG. 24A is a bar plot illustrating the effect of oligopeptide C23 on the levels of expression of E-selectin (top) and ICAM-1 (bottom) in the lungs of septic mice.
FIG. 24B is a bar plot illustrating the effect of oligopeptide C23 on the levels of expression of TNF-alpha (top) and IL-1beta (bottom) in the lungs of septic mice.
FIG. 24C is a bar plot illustrating the effect of oligopeptide C23 on the levels of expression of TNF-alpha (top) and IL-1beta (bottom) in the blood serum of septic mice.

In a further experiment, the oligopeptide C23 was demonstrated to decrease cecal ligation and puncture (CLP)-induced expression of endothelial cell activation markers and pro-inflammatory cytokines in the lungs. Mice subjected to CLP were treated 2 hours later with the oligopeptide C23 (8 mg/kg) or saline. A significant decrease in the expression of endothelial cell activation markers E-selectin and ICAM-1 in the lungs and of pro-inflammatory cytokines TNF-α and IL-1β, also in the lungs, was observed 24 hours post-CLP. The results are shown in FIG. 24A and FIG. 24B. These results indicate that C23 is able to block CIRP activity.

Finally, as shown in FIG. 23C, mice treated with C23 also had lower serum levels of TNF-α and IL-6, which are indicators of severity and of prognosis in sepsis. C23 suppression of CIRP's deleterious effects—not only in the lungs but also systemically—suggests that C23 has the potential to be developed into a novel treatment for sepsis via attenuation of endothelial cell damage.

In FIGS. 23A through 23C: Mean+/−SD; n=4-8/group; *P<0.05 vs. sham, #P<0.05 vs. vehicle, one-way ANOVA. mRNA amounts are measured by qPCR; protein levels are measured by ELISA.

Example 14: Treatment with Oligopeptide C23 Prolongs the Survival of Septic Mice The following experiment provides the results of a survival study of septic mice, demonstrating overall beneficial effect the oligopeptide C23.

Figures 25A, 25B:
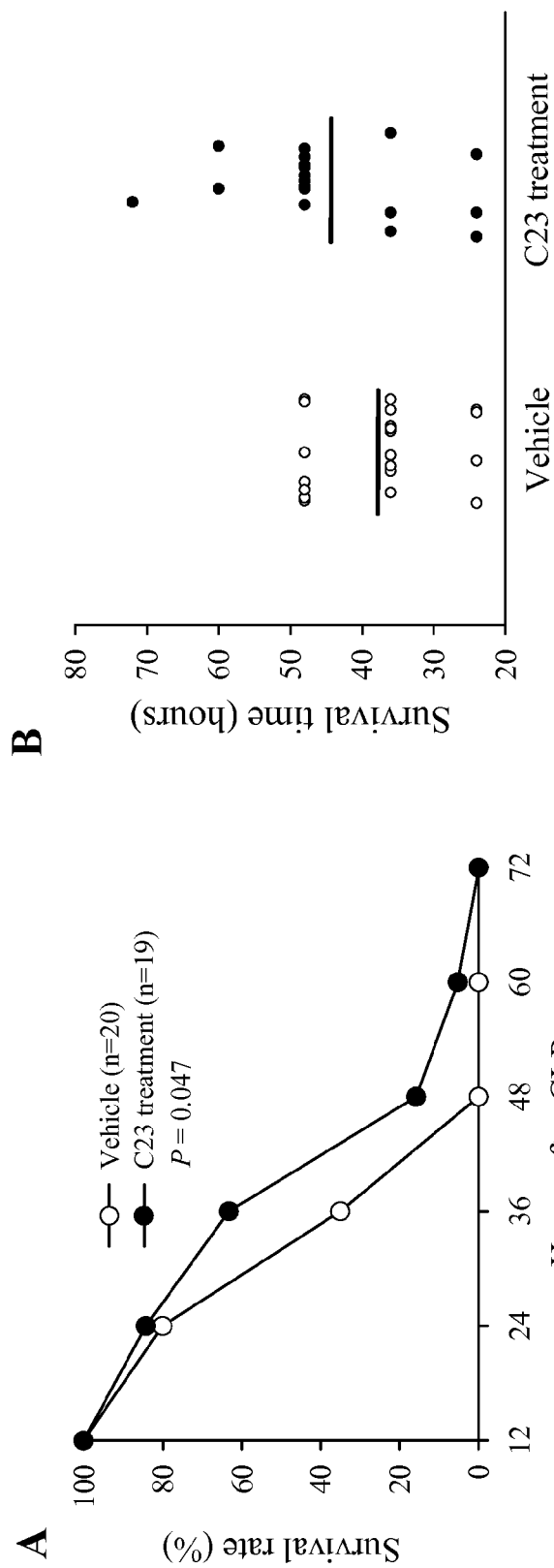
FIG. 25A is a plot of survival rate of septic mice as a function hours after CLP procedure, demonstrating the effect of oligopeptide C23.
FIG. 25B is a scatter plot demonstrating the effect of oligopeptide C23 on the survival rate of septic mice.

Mice were subjected to CLP and treated immediately after operation with the antibiotic imipenem (0.5 µg/kg BW) and resuscitative fluid. At 2 hours after CLP, mice were administered C23 (8 mg/kg BW) or an equivalent volume of normal saline (vehicle) via the internal jugular vein. Survival was then assessed every 12 hours. In this model of severe sepsis, all vehicle mice died within 48 hours post-CLP, while some of C23-treated mice lived longer (FIG. 25A, $P<0.05$, survival rates were analyzed by the Kaplan-Meier estimator using a log-rank test). The average survival time was 37.8 hours in the vehicle group and 44.2 hours in the C23-treated mice (FIG. 25B, individual survival times and average survival time (horizontal line) for each group). These results indicate C23 is beneficial and extends the survival time of severe septic mice.

While this invention has been particularly shown and described with references to example embodiments thereof, it will be understood by those skilled in the art that various changes in form and details may be made therein without departing from the scope of the invention encompassed by the appended claims.

All references cited in this specification are hereby incorporated by reference.

---

What is claimed is:

1. A synthetic peptide fragment of Cold-Inducible RNA-Binding Protein (CIRP), selected from the group consisting of:
- a synthetic peptide consisting of the amino acid residue sequence Gly-Arg-Gly-Phe-Ser-Arg-Gly-Gly-Gly-Asp (SEQ ID NO: 12), wherein at least one amino acid is a D-amino acid,
- a synthetic peptide consisting of the amino acid residue sequence Gly-Gly-Arg-Gly-Arg-Gly-Arg-Gly-Phe-Ser-Arg-Gly-Gly-Gly-Asp (SEQ ID NO: 13), wherein at least one amino acid is a D-amino acid, and
- a synthetic peptide consisting of the amino acid residue sequence Gly-Arg-Gly-Phe-Ser-Arg-Gly-Gly-Gly-Asp-Arg-Gly-Tyr-Gly-Gly (SEQ ID NO: 14), wherein at least one amino acid is a D-amino acid, or a pharmaceutically acceptable salt thereof; and wherein the synthetic peptide fragment improves wound healing in contrast to naturally occurring CIRP.

2. A synthetic peptide fragment of Cold-Inducible RNA-Binding Protein (CIRP), selected from the group consisting of:
- a synthetic peptide consisting of the amino acid residue sequence Gly-Arg-Gly-Phe-Ser-Arg-Gly-Gly-Gly-Asp (SEQ ID NO: 12), wherein each amino acid is a D-amino acid,
- a synthetic peptide consisting of the amino acid residue sequence Gly-Gly-Arg-Gly-Arg-Gly-Arg-Gly-Phe-Ser-Arg-Gly-Gly-Gly-Asp (SEQ ID NO: 13), wherein each amino acid is a D-amino acid, and
- a synthetic peptide consisting of the amino acid residue sequence Gly-Arg-Gly-Phe-Ser-Arg-Gly-Gly- Asp-Arg-Gly-Tyr-Gly-Gly (SEQ ID NO: 14), wherein each amino acid is a D-amino acid, or a pharmaceutically acceptable salt thereof; and wherein the synthetic peptide fragment improves wound healing in contrast to naturally occurring CIRP.

3. A synthetic peptide fragment of Cold-Inducible RNA-Binding Protein (CIRP), selected from the group consisting of:

a synthetic peptide consisting of the amino acid residue sequence Gly-Arg-Gly-Phe-Ser-Arg-Gly-Gly-Gly-Asp (SEQ ID NO: 12), wherein the amino terminal is acetylated and the carboxy terminal is amidated, a synthetic peptide consisting of the amino acid residue sequence Gly-Gly-Arg-Gly-Arg-Gly-Arg-Gly-Phe-Ser-Arg-Gly-Gly-Gly-Asp (SEQ ID NO: 13), wherein the amino terminal is acetylated and the carboxy terminal is amidated, and a synthetic peptide consisting of the amino acid residue sequence Gly-Arg-Gly-Phe-Ser-Arg-Gly-Gly-Gly-Asp-Arg-Gly-Tyr-Gly-Gly (SEQ ID NO: 14), wherein the amino terminal is acetylated and the carboxy terminal is amidated, or a pharmaceutically acceptable salt thereof; and wherein the synthetic peptide fragment improves wound healing in contrast to naturally occurring CIRP.

4. A synthetic peptide fragment of Cold-Inducible RNA-Binding Protein (CIRP), selected from the group consisting of:

a synthetic peptide consisting of the amino acid residue sequence Gly-Arg-Gly-Phe-Ser-Arg-Gly-Gly-Gly-Asp (SEQ ID NO: 12), wherein the amino terminal is acetylated or the carboxy terminal is amidated, a synthetic peptide consisting of the amino acid residue sequence Gly-Gly-Arg-Gly-Arg-Gly-Arg-Gly-Phe-Ser-Arg-Gly-Gly-Gly-Asp (SEQ ID NO: 13), wherein the amino terminal is acetylated or the carboxy terminal is amidated, and a synthetic peptide consisting of the amino acid residue sequence Gly-Arg-Gly-Phe-Ser-Arg-Gly-Gly-Gly-Asp-Arg-Gly-Tyr-Gly-Gly (SEQ ID NO: 14), wherein the amino terminal is acetylated or the carboxy terminal is amidated, or a pharmaceutically acceptable salt thereof; and wherein the synthetic peptide fragment improves wound healing in contrast to naturally occurring CIRP.

\* \* \* \* \*